(12) United States Patent
Grifantini et al.

(10) Patent No.: US 9,182,404 B2
(45) Date of Patent: Nov. 10, 2015

(54) TUMOR MARKERS AND METHODS OF USE THEREOF

(75) Inventors: Renata Grifantini, Siena (IT); Piero Pileri, Siena (IT); Susanna Campagnoli, Siena (IT); Andrea Pierleoni, Siena (IT); Renzo Nogarotto, Siena (IT)

(73) Assignee: EXTERNAUTICS S.P.A., Siena (IT)

( * ) Notice: Subject to any disclaimer, the term of this patent is extended or adjusted under 35 U.S.C. 154(b) by 258 days.

(21) Appl. No.: 13/146,524

(22) PCT Filed: Jan. 27, 2010

(86) PCT No.: PCT/EP2010/000502
§ 371 (c)(1), (2), (4) Date: Oct. 17, 2011

(87) PCT Pub. No.: WO2010/086162
PCT Pub. Date: Aug. 5, 2010

(65) Prior Publication Data
US 2012/0045439 A1    Feb. 23, 2012

(30) Foreign Application Priority Data
Jan. 28, 2009 (EP) .................................... 09151559

(51) Int. Cl.
*G01N 33/574* (2006.01)
*C07K 16/30* (2006.01)

(52) U.S. Cl.
CPC .......... *G01N 33/57423* (2013.01); *C07K 16/30* (2013.01); *G01N 33/57415* (2013.01); *G01N 33/57419* (2013.01); *G01N 33/57434* (2013.01); *G01N 33/57449* (2013.01)

(58) Field of Classification Search
None
See application file for complete search history.

(56) References Cited

U.S. PATENT DOCUMENTS

| 2003/0219741 A1* | 11/2003 | Isogai et al. ............. 435/6 |
| 2004/0076955 A1* | 4/2004 | Mack et al. ............. 435/6 |
| 2006/0019256 A1* | 1/2006 | Clarke et al. ............. 435/6 |

FOREIGN PATENT DOCUMENTS

WO    02/059377 A    8/2002

OTHER PUBLICATIONS

Reiter et al. (Genes and Development, 20:22-27, 2006).*
Exhibit A from PhosphoSite Plus, Jul. 2013.*
Exhibit B from Expression Atlas, Jul. 2013.*
Lamerz, R., et al., "Tumour markers," Deutsche Medizinische Wochenschrift (1946) Dec. 10, 2004, vol. 129, No. 50, pp. 2722-2730, XP002519691, ISSN: 0012-0472.
Database Uniprot [online], Apr. 4, 2006, "RecName: Full=Tectonic-1; Flags: Precursor;" XP002519692, retrieved from EBI accession No. UNIPROT:Q2MV58, Database accession No. Q2MV58.
Database Uniprot [online], Dec. 4, 2007, "SubName: Full=Putative uncharacterized protein TCTN1;" XP002519693, retrieved from EBI accession No. UNIPROT:A8MW34, Database accession No. A8MW34.
Database Uniprot [online], Dec. 4, 2007, "SubName: Full=Putative uncharacterized protein TCTN1;" XP002519694, retrieved from EBI accession No. UNIPROT:A8MX11, Database accession No. A8MX11.
International Search Report and Written Opinion of the International Searching Authority issued in International Application No. PCT/EP2010/00502.

* cited by examiner

*Primary Examiner* — Brad Duffy
*Assistant Examiner* — Nelson B Moseley, II
(74) *Attorney, Agent, or Firm* — Silvia Salvadori, P.C.; Silvia Salvadori

(57) ABSTRACT

The invention provides newly identified proteins as markers for the detection of tumors, or as targets for their treatment, particularly of tumors affecting lung, colon, breast, ovary; affinity ligands capable of selectively interacting with the newly identified markers; methods of screening a tissue sample for malignancy, for determining the presence of a tumor in a subject and for screening a test compound as an antitumor candidate; a diagnostic kit.

6 Claims, 20 Drawing Sheets

TUMOR MARKERS AND METHODS OF USE THEREOF

This application is a U.S. national stage of PCT/EP2010/000502 filed on Jan. 27, 2010 which claims priority to and the benefit of European Application No. 09151559.3 filed on Jan. 28, 2009, the contents of which are incorporated herein by reference.

The present invention relates to newly identified proteins as markers for the detection of tumors, or as targets for their treatment, particularly of tumors affecting lung, colon, breast and ovary. Also provided are affinity ligands capable of selectively interacting with the newly identified markers, as well as methods for tumor diagnosis and therapy using such ligands.

BACKGROUND OF THE INVENTION

Tumor Markers (or Biomarkers)

Tumor markers are substances that can be produced by tumor cells or by other cells of the body in response to cancer. In particular, a protein biomarker is either a single protein or a panel of different proteins that could be used to unambiguously distinguish a disease state. Ideally, a biomarker would have both a high specificity and sensitivity, being represented in a significant percentage of the cases of given disease and not in healthy state.

Biomarkers can be identified in different biological samples, like tissue biopsies or preferably biological fluids (saliva, urine, blood-derivatives and other body fluids), whose collection does not necessitate invasive treatments. Tumor marker levels may be categorized in three major classes on the basis of their clinical use. Diagnostic markers can be used in the detection and diagnosis of cancer. Prognostics markers are indicative of specific outcomes of the disease and can be used to define predictive models that allow the clinicians to predict the likely prognosis of the disease at time of diagnosis. Moreover, prognosis markers are helpful to monitor the patient response to a drug therapy and facilitate a more personalized patient management. A decrease or return to a normal level may indicate that the cancer is responding to therapy, whereas an increase may indicate that the cancer is not responding. After treatment has ended, tumor marker levels may be used to check for recurrence of the tumor. Finally, therapeutic markers can be used to develop tumor-specific drugs or affinity ligand (i.e. antibodies) for a tumor treatment.

Currently, although an abnormal tumor marker level may suggest cancer, this alone is usually not enough to accurately diagnose cancer and their measurement in body fluids is frequently combined with other tests, such as a biopsy and radioscopic examination. Frequently, tumor marker levels are not altered in all of people with a certain cancer disease, especially if the cancer is at early stage. Some tumor marker levels can also be altered in patients with noncancerous conditions. Most biomarkers commonly used in clinical practice do not reach a sufficiently high level of specificity and sensitivity to unambiguously distinguish a tumor from a normal state.

To date the number of markers that are expressed abnormally is limited to certain types/subtypes of cancer, some of which are also found in other diseases. (http://www.cancer.gov/cancertopics/factsheet).

For example, prostate-specific antigen (PSA) levels are often used to screen men for prostate cancer, but this is controversial since elevated PSA levels can be caused by both prostate cancer or benign conditions, and most men with elevated PSA levels turn out not to have prostate cancer.

Another tumor marker, Cancer Antigen 125, (CA 125), is sometimes used to screen women who have an increased risk for ovarian cancer. Scientists are studying whether measurement of CA 125, along with other tests and exams, is useful to find ovarian cancer before symptoms develop. So far, CA 125 measurement is not sensitive or specific enough to be used to screen all women for ovarian cancer. Mostly, CA 125 is used to monitor response to treatment and check for recurrence in women with ovarian cancer. Finally, human epidermal growth factor receptor (HER2) is a marker protein overproduced in about 20% of breast cancers, whose expression is typically associated with a more aggressive and recurrent tumors of this class.

Routine Screening Test for Tumor Diagnosis

Screening tests are a way of detecting cancer early, before there are any symptoms. For a screening test to be helpful, it should have high sensitivity and specificity. Sensitivity refers to the test's ability to identify people who have the disease. Specificity refers to the test's ability to identify people who do not have the disease. Different molecular biology approaches such as analysis of DNA sequencing, small nucleotide polymorphyms, in situ hybridization and whole transcriptional profile analysis have done remarkable progresses to discriminate a tumor state from a normal state and are accelerating the knowledge process in the tumor field. However so far different reasons are delaying their use in the common clinical practice, including the higher analysis complexity and their expensiveness. Other diagnosis tools whose application is increasing in clinics include in situ hybridization and gene sequencing.

Currently, Immuno-HistoChemistry (IHC), a technique that allows the detection of proteins expressed in tissues and cells using specific antibodies, is the most commonly used method for the clinical diagnosis of tumor samples. This technique enables the analysis of cell morphology and the classification of tissue samples on the basis of their immunoreactivity. However, at present, IHC can be used in clinical practice to detect cancerous cells of tumor types for which protein markers and specific antibodies are available. In this context, the identification of a large panel of markers for the most frequent cancer classes would have a great impact in the clinical diagnosis of the disease.

Anti-Cancer Therapies

In the last decades, an overwhelming number of studies remarkably contributed to the comprehension of the molecular mechanisms leading to cancer. However, this scientific progress in the molecular oncology field has not been paralleled by a comparable progress in cancer diagnosis and therapy. Surgery and/or radiotherapy are the still the main modality of local treatment of cancer in the majority of patients. However, these treatments are effective only at initial phases of the disease and in particular for solid tumors of epithelial origin, as is the case of colon, lung, breast, ovary, prostate and others, while they are not effective for distant recurrence of the disease. In some tumor classes, chemotherapeutic treatments have been developed, which generally relies on drugs, hormones and antibodies, targeting specific biological processes used by cancers to grow and spread. However, so far many cancer therapies had limited efficacy due to severity of side effects and overall toxicity. Indeed, a major effort in cancer therapy is the development of treatments able to target specifically tumor cells causing limited damages to surrounding normal cells thereby decreasing adverse side effects. Recent developments in cancer therapy in this direction are encouraging, indicating that in some cases a cancer specific therapy is feasible. In particular, the development and commercialization of humanized monoclonal antibodies that recognize specifically tumor-associated markers and promote the elimination of cancer is one of the most promising solution that appears to be an extremely favorable market opportunity for pharmaceutical companies. However, at present the number of therapeutic antibodies available on the market or under clinical studies is very limited and restricted to specific cancer classes. So far licensed monoclonal antibodies currently used in clinics for the therapy of specific tumor classes show only a partial efficacy and are frequently associated with chemotherapies to increase their therapeutic effect. Administration of Trastuzumab (Herceptin), a commercial monoclonal antibody targeting HER2 in conjunction with Taxol adjuvant chemotherapy induces tumor remission in about 42% of the cases (1). Bevacizumab (Avastin) and Cetuximab (Erbitux) are two monoclonal antibodies recently licensed for use in humans, targeting the endothelial and epithelial growth factors respectively that, combined with adjuvant chemotherapy, proved to be effective against different tumor diseases. Bevacizumab proved to be effective in prolonging the life of patients with metastatic colorectal, breast and lung cancers. Cetuximab demonstrated efficacy in patients with tumor types refractory to standard chemotherapeutic treatments (1).

In summary, available screening tests for tumor diagnosis are uncomfortable or invasive and this sometimes limits their applications. Moreover tumor markers available today have a limited utility in clinics due to either their incapability to detect all tumor subtypes of the defined cancers types and/or to distinguish unambiguously tumor vs. normal tissues. Similarly, licensed monoclonal antibodies combined with standard chemotherapies are not effective against the majority of cases. Therefore, there is a great demand for new tools to advance the diagnosis and treatment of cancer.

Experimental Approaches Commonly Used to Identify Tumor Markers

Most popular approaches used to discover new tumor markers are based on genome-wide transcription profile or total protein content analyses of tumor. These studies usually lead to the identification of groups of mRNAs and proteins which are differentially expressed in tumors. Validation experiments then follow to eventually single out, among the hundreds of RNAs/proteins identified, the very few that have the potential to become useful markers. Although often successful, these approaches have several limitations and often, do not provide firm indications on the association of protein markers with tumor. A first limitation is that, since frequently mRNA levels not always correlate with corresponding protein abundance (approx. 50% correlation), studies based on transcription profile do not provide solid information regarding the expression of protein markers in tumor (2, 3, 4, 5).

A second limitation is that neither transcription profiles nor analysis of total protein content discriminate post-translation modifications, which often occur during oncogenesis. These modifications, including phosphorylations, acetylations, and glycosylations, or protein cleavages influence significantly protein stability, localization, interactions, and functions (6).

As a consequence, large scale studies generally result in long lists of differentially expressed genes that would require complex experimental paths in order to validate the potential markers. However, large scale genomic/proteomic studies reporting novel tumor markers frequently lack of confirmation data on the reported potential novel markers and thus do not provide solid demonstration on the association of the described protein markers with tumor.

Approach Used to Identify the Protein Markers Included in the Present Invention

The approach that we used to identify protein markers is based on an innovative immuno-proteomic technology. In essence, a library of recombinant human proteins has been produced from *E. coli* and is being used to generate polyclonal antibodies against each of the recombinant proteins.

The screening of the antibodies library on Tissue microarrays (TMAs) carrying clinical samples from different patients affected by the tumor under investigation leads to the identification of specific tumor marker proteins. Therefore, by screening TMAs with the antibody library, the tumor markers are visualized by IHC, the classical technology applied in all clinical pathology laboratories. Since TMAs also include healthy tissues, the specificity of the antibodies for the tumors can be immediately appreciated and information on the relative level of expression and cellular localization of the markers could be obtained. In our approach the markers are subjected to a validation process consisting in a molecular and cellular characterization.

Altogether, the detection the marker proteins disclosed in the present invention selectively in tumor samples and the subsequent validation experiments lead to an unambiguous confirmation of the marker identity and confirm its association with defined tumor classes. Moreover this experimental process provides an indication of the possible use of the proteins as tools for diagnostic or therapeutic intervention. For instance, proteins showing a cell surface localization could be both diagnostic and therapeutic markers, against which both chemical and antibody therapies can be developed. Differently, markers showing a cytoplasmic localization could be more likely considered for the development of tumor diagnostic tests and chemotherapy/small molecules treatments.

SUMMARY OF THE INVENTION

The present invention provides new means for the detection and treatment of tumors, in particular colo-rectal, lung, ovary and breast cancers, based on the identification of protein markers specific for these tumor types, namely: a) Tectonic-1 (TCTN1), Tectonic-2 (TCTN2) and Tectonic-3 (TCTN3) proteins, b) HIGD2A and HIGD2B proteins, c) chromosome 4 open reading frame 32 (C4orf32) protein and d) FAM62A protein. In preferred embodiments, the invention provides the use of a) TCTN1, TCTN2 and TCTN3 proteins, as marker or target for colon, lung and ovary tumors, b) Hypoxia induced proteins A and B (HIGD2A and HIGD2B) as markers or targets for colon and ovary tumors, c) C4orf32 proteins as markers or targets for breast and lung tumors and d) FAM62A as marker or target for breast, colon, lung and ovary tumors.

The invention also provides a method for the diagnosis of these cancer types, comprising a step of detecting the above-identified markers in a biological sample, e.g. in a tissue sample of a subject suspected of having or at risk of developing malignancies or susceptible to cancer recurrences. In particular, the protein markers of the invention allow to specifically detect lung, colon, breast and ovary cancers, according to their tumor-specificity, namely: a) TCTN1, TCTN2 and TCTN3 proteins for colon, lung and ovary tumors; b) Hypoxia induced proteins A and B (HIGD2A and HIGD2B) for colon and ovary tumors; c) chromosome 4 open reading frame 32 proteins for breast and lung tumors; d) FAM62A protein for breast, colon, lung and ovary tumors.

In addition, the tumor markers identify novel targets for affinity ligands which can be used for therapeutic applications, especially in the treatment of colo-rectal, lung, ovary and breast proliferative diseases. Also provided are affinity ligands, particularly antibodies, capable of selectively interacting with the newly identified protein markers.

DETAILED DISCLOSURE OF THE INVENTION

The present invention is based on the surprising finding of antibodies that are able to specifically bind tumor tissues from patients, while negative or very poor binding is observed in normal tissues from the same patients. These antibodies have been found to specifically bind proteins for which no previous association with tumor has been reported. Hence, in a first aspect, the invention provides a tumor marker which is selected from the group consisting of:
  a) Tectonic-1 (TCTN1) protein, in one of its isoforms SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a different isoform having sequence identity of at least 80%, preferably at least 90%, more preferably at least 95% to SEQ ID NO:1, SEQ ID NO:2, SEQ ID NO:3, SEQ ID NO:4, SEQ ID NO:5, SEQ ID NO:6, SEQ ID NO:7 or SEQ ID NO:8; or a nucleic acid molecule containing a sequence coding for a TCTN1 protein, said encoding sequence being preferably selected from SEQ ID NO:20, SEQ ID NO:21, SEQ ID NO:22, SEQ ID NO:23, SEQ ID NO:24, SEQ ID NO:25, SEQ ID NO:26 and SEQ ID NO:27;
  b) Tectonic-2 (TCTN2) protein, SEQ ID NO:9 or an isoform thereof having sequence identity of at least 80%, preferably at least 90%, more preferably at least 95% to SEQ ID NO:9; or a nucleic acid molecule containing a sequence coding for a TCTN2 protein, said encoding sequence being preferably SEQ ID NO: 28;
  c) Tectonic-3 (TCTN3) protein in one of its isoforms SEQ ID NO:10, SEQ ID NO:11, SEQ ID NO:12 or SEQ ID NO:13, or a different isoform having sequence identity of at least 80%, preferably at least 90%, more preferably at least 95% to SEQ ID NO:10, SEQ ID NO:11, SEQ ID NO:12 or SEQ ID NO:13; or a nucleic acid molecule containing a sequence coding for a TCTN3 protein, said encoding sequence being preferably selected from SEQ ID NO:29, SEQ ID NO:30, SEQ ID NO:31 and SEQ ID NO:32;
  d) Hypoxia induced protein A (HIGD2A), SEQ ID NO:14 or an isoform thereof having sequence identity of at least 80%, preferably at least 90%, more preferably at least 95% to SEQ ID NO:14; or a nucleic acid molecule containing a sequence coding for a HIGD2A protein, said encoding sequence being preferably SEQ ID NO:33;
  e) Hypoxia induced protein B (HIGD2B), SEQ ID NO:15 or an isoform thereof having sequence identity of at least 80%, preferably at least 90%, more preferably at least 95% to SEQ ID NO:15; or a nucleic acid molecule containing a sequence coding for a HIGD2B protein, said encoding sequence being preferably SEQ ID NO:34;
  f) C4orf32 protein, SEQ ID NO:16, or an isoform thereof having sequence identity of at least 80%, preferably at least 90%, more preferably at least 95% to SEQ ID NO:16; or a nucleic acid molecule containing a sequence coding for a C4orf32 protein, said encoding sequence being preferably SEQ ID NO:35;
  g) FAM62A protein, in one of its variant isoforms SEQ ID NO:17, SEQ ID NO:18 or SEQ ID NO:19, or a different isoform having sequence identity of at least 80%, preferably at least 90%, more preferably at least 95% to any of SEQ ID NO:17, SEQ ID NO:18 or SEQ ID NO:19; or a nucleic acid molecule containing a sequence coding for a FAM62A protein, said encoding sequence being preferably selected from SEQ ID NO: 36, SEQ ID NO: 37 and SEQ ID NO: 38.

TCTN1 (Gene name: TCTN1; Gene ID: ENSG00000204852, Protein names: Tectonic-1, TCT1, TCTN1. Eight variants identified:

| Protein ID | Transcript ID |
| --- | --- |
| ENSP00000366882 | ENST00000377654 |
| ENSP00000380771 | ENST00000397650 |
| ENSP00000380772 | ENST00000397652 |
| ENSP00000380774 | ENST00000397654 |
| ENSP00000380775 | ENST00000397655 |
| ENSP00000380776 | ENST00000397656 |
| ENSP00000380777 | ENST00000397657 |
| ENSP00000380779 | ENST00000397659), |

TCTN2 (Gene names: TCTN2, C12orf38, TECT2 Gene ID: ENSG00000168778; Transcript ID: ENST00000303372; Protein Names: Tectonic-2, TCTN2; Protein ID: ENSP00000304941;), and TCTN3 (Gene names: TCTN3, C10orf61, TECT3; Gene ID: ENSG00000119977; protein names: Tectonic-3, TCT3, TCTN3. Four variants identified:

| Protein ID | Transcript ID |
| --- | --- |
| ENSP00000265993 | ENST00000265993 |
| ENSP00000345815 | ENST00000343162 |
| ENSP00000360253 | ENST00000371209 |
| ENSP00000360261 | ENST00000371217) | are proteins without previous known association in any cancer disease and are preferably used as markers for colon-, lung- and ovary-type tumors. Antibodies generated against the TCTN2 protein show a selective immunoreactivity in histological preparation of colo-rectal cancer tissues, lung cancer tissues, ovary cancer tissues, which indicates the presence of TCTN2 in these cancer samples. The most striking finding is the marker positivity in colo-rectal carcinomas, with 100% positive samples, which makes TCTN2 protein and its antibody particularly convenient tools for distinguishing a colo-rectal cancer from a normal state.

As described in detail in the Examples, TCTN1, TCTN2 and TCTN3 proteins share a large common domain showing short highly conserved internal sequences and thereby, polyclonal antibodies generated against TCTN2 protein are capable to recognize also the related proteins TCTN1 and TCTN3.

HIGD2A (HIG1 domain family member 2A, Protein ID: ENSP00000274787; Gene name: HIGD2A, Gene ID: ENSG00000146066; Transcript ID: ENST00000274787) and its homologous protein HIGD2BP (HIG1 domain family member 2B, Protein ID: ENSP00000307951; Gene name: HIGD2BP, Gene ID: ENSG00000175202; Transcript ID: ENST00000311755) are proteins without previous known association in any cancer disease and are preferably used as markers for colon- and ovary-type tumors. Antibodies generated to a fragment of HIGD2A show a selective immunoreactivity in histological preparation of colo-rectal cancer tissues and ovary cancer tissues, which indicates the presence of this protein in these cancer samples. As described in detail in the Examples, antibodies generated against HIGD2A protein are capable to recognize also its homologous protein HIGD2B and viceversa, indicating that both proteins can be stained by the same antibody.

C4orf32 (Protein ID: ENSP00000310182; Gene ID: ENSG00000174749, Gene Name: C4orf32; Transcript ID: ENST00000309733) is a protein without previous known association in any cancer disease and is preferably used as a marker for breast- and lung-type cancers. Antibodies generated to a fragment of C4orf32 show selective immunoreactivity in histological preparation of breast cancer tissues and lung cancer tissues, which indicates the presence this protein in these cancer samples.

FAM62A (Gene names: FAM62A, ESYT1, KIAA0747, MBC2; Gene ID: ENSG00000139641, Protein names: E-Syt1, Extended-synaptotagmin-1; Membrane-bound C2 domain-containing protein, Protein FAM62A. Three variants identified:

| Protein ID | Transcript ID |
|---|---|
| ENSP00000386045 | ENST00000402331 |
| ENSP00000377612 | ENST00000394048 |
| ENSP00000267113 | ENST00000267113) | is a protein without previous known association with any tumor class, although the corresponding genomic sequence can be isolated from pancreas tumor tissue along with a large number of different sequences (WO9955858).

Antibodies against a fragment of FAM62A showed a selective immunoreactivity in histological preparation of tumor tissue samples from breast, colon, lung and ovary.

A further aspect of this invention is a method of screening a tissue sample for malignancy, which comprises determining the presence in said sample of at least one of the above-mentioned tumor markers. This method includes detecting either the marker protein, e.g. by means of labeled monoclonal or polyclonal antibodies that specifically bind to the target protein, or the respective mRNA, e.g. by means of polymerase chain reaction techniques such as RT-PCR. The methods for detecting proteins in a tissue sample are known to one skilled in the art and include immunoradiometric, immunoenzymatic or immunohistochemical techniques, such as radioimmunoassays, immunofluorescent assays or enzyme-linked immunoassays. Other known protein analysis techniques, such as polyacrylamide gel electrophoresis (PAGE), Western blot or Dot blot are suitable as well. Preferably, the detection of the protein marker is carried out with the immune-hystochemistry technology, particularly by means of High Through-Put methods that allow the analyses of the antibody immune-reactivity simultaneously on different tissue samples immobilized on a microscope slide. Briefly, each Tissue Micro Array (TMA) slide includes tissue samples suspected of malignancy taken from different patients, and an equal number of normal tissue samples from the same patients as controls. The direct comparison of samples by qualitative or quantitative measurement, e.g. by enzimatic or colorimetric reactions, allows the identification of tumors.

In one embodiment, the invention provides a method of screening a sample of colon or colo-rectal tissue for malignancy, which comprises determining the presence in said sample of a tumor marker selected from TCTN1, TCTN2, TCTN3, HIGD2A, HIGD2B and FAM62A, variants or isoforms or combinations thereof as described above. In another embodiment, the invention provides a method of screening a sample of lung tissue for malignancy, which comprises determining the presence in said sample of a tumor marker selected from TCTN1, TCTN2, TCTN3, C4orf32 and FAM62A, variants or isoforms or combinations thereof as described above. In a further embodiment, the invention provides a method of screening a sample of ovarian tissue for malignancy, which comprises determining the presence in said sample of a tumor marker selected from TCTN1, TCTN2, TCTN3, HIGD2A, HIGD2B and FAM62A, variants or isoforms or combinations thereof as described above. In a yet further embodiment, the invention provides a method of screening a sample of breast tissue for malignancy, which comprises determining the presence in said sample of a tumor marker selected from C4orf32 and FAM62A, variants or isoforms or combinations thereof as described above.

A further aspect of the invention is a method in vitro for determining the presence of a tumor in a subject, which comprises the steps of:
  (1) providing a sample of the tissue suspected of containing tumor cells;
  (2) determining the presence of a tumor marker as above defined, or a combination thereof in said tissue sample by detecting the expression of the marker protein or the presence of the respective mRNA transcript;
wherein the detection of one or more tumor markers in the tissue sample is indicative of the presence of tumor in said subject.

The methods and techniques for carrying out the assay are known to one skilled in the art and are preferably based on immunoreactions for detecting proteins and on PCR methods for the detection of mRNAs. The same methods for detecting proteins or mRNAs from a tissue sample as disclosed above can be applied.

A further aspect of this invention is the use of the tumor markers herein provided as targets for the identification of candidate antitumor agents. Accordingly, the invention provides a method for screening a test compound which comprises contacting the cells expressing a tumor-associated protein selected from TCTN1, TCTN2, TCTN3, HIGD2A and HIGD2B, C4orf32 and FAM62A with the test compound, and determining the binding of said compound to said cells. In addition, the ability of the test compound to modulate the activity of each target molecule can be assayed.

A further aspect of the invention is a method of suppressing the function or expression of a tumor-associated protein herein provided. This includes inhibiting or blocking the protein, e.g. by means of antibodies, or silencing the gene encoding therefor, e.g. by RNA interference or RNA antisense technologies. As shown in the experimental section, marker expression confers a malignant phenotype to cells, making them able to grow and proliferate in an anchorage-independent fashion in an in vitro assay.

In one embodiment, the invention provides an antibody or a fragment thereof which is able to specifically recognize and bind to one of the tumor-associated proteins described above. The term "antibody" as used herein refers to all types of immunoglobulins, including IgG, IgM, IgA, IgD and IgE. Such antibodies may include polyclonal, monoclonal, chimeric, single chain, antibodies or fragments such as Fab or scFv. The antibodies may be of various origin, including human, mouse, rat, rabbit and horse, or chimeric antibodies. The production of antibodies is well known in the art. For the production of antibodies in experimental animals, various hosts including goats, rabbits, rats, mice, and others, may be immunized by injection with polypeptides of the present invention or any fragment or oligopeptide or derivative thereof which has immunogenic properties or forms a suitable epitope. Monoclonal antibodies may be produced following the procedures described in Kohler and Milstein, Nature 265:495 (1975) or other techniques known in the art.

The antibodies to the tumor markers of the invention can be used to detect the presence of the marker in histologic preparations or to distinguish tumor cells from normal cells. To that purpose, the antibodies may be labeled with radiocative, fluorescent or enzyme labels.

In addition, the antibodies can be used for treating proliferative diseases by modulating, e.g. inhibiting or abolishing the activity of a target protein according to the invention. Therefore, in a further aspect the invention provides the use of antibodies to a tumor-associated protein selected from TCTN1, TCTN2, TCTN3, HIGD2A and HIGD2B, C4orf32 and FAM62A, for the preparation of a therapeutic agent for the treatment of proliferative diseases. For use in therapy, the antibodies can be formulated with suitable carriers and excipients, optionally with the addition of adjuvants to enhance their effects.

In a further embodiment, the invention provides a small interfering RNA (siRNAs) complementary to a sequence selected from the group consisting of SEQ ID NO:39 through SEQ ID NO:55, for use in tumor-gene silencing.

A further aspect of the invention relates to a diagnostic kit containing suitable means for detection, in particular the polypeptides or polynucleotides, antibodies or fragments or derivatives thereof described above, reagents, buffers, solutions and materials needed for setting up and carrying out the immunoassays, nucleic acid hybridization or PCR assays as described above. Parts of the kit of the invention can be packaged individually in vials or bottles or in combination in containers or multicontainer units.

stained with anti-C4orf32 antibodies. The antibody-stains specifically tumor cells (in dark grey); negative or poor staining is visible in normal cells.

Figure 12:
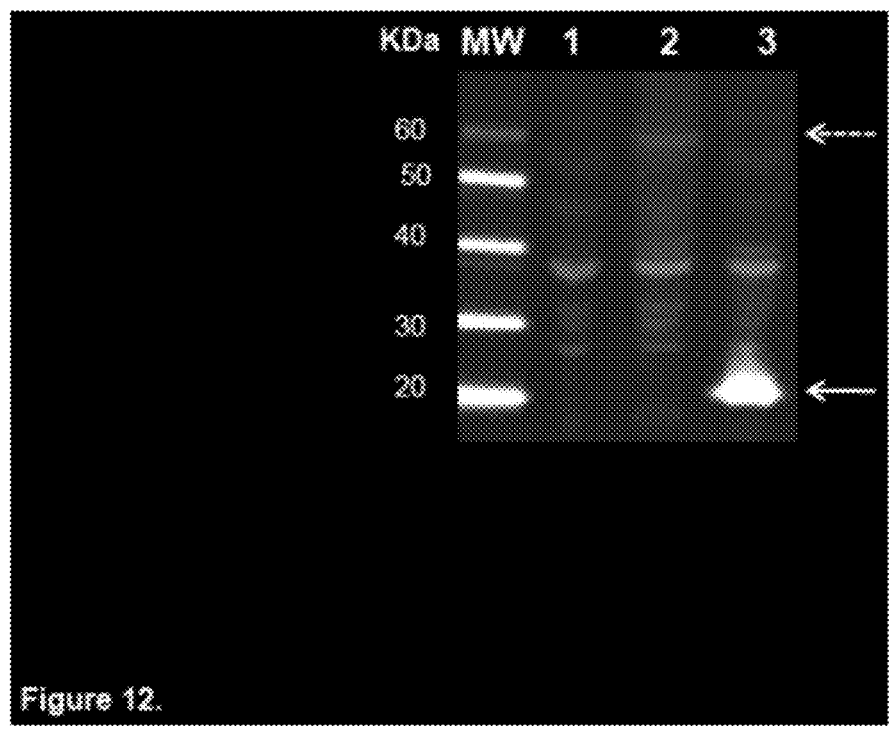

FIG. 12. C4orf32 expression in transiently transfected HeLa cells. Western blot analysis of C4orf32 expression in total protein extracts from HeLa cells (corresponding to $1 \times 10^6$ cells) transfected with the empty vector pcDNA3 (lane 1) or with the plasmid encoding C4orf32 either in the untagged native (lane 2) or the V5-fusion forms (lane 3) stained with anti-C4orf32 antibodies. A solid arrow marks the expected C4orf32 band in cells expressing the V5-fusion form (lane 3). A dashed arrow indicates the high molecular weight band in cells expressing native C4orf32 (lane 2), likely corresponding to an aggregated form of the protein. Molecular weight markers are reported on the left.

Figure 13:
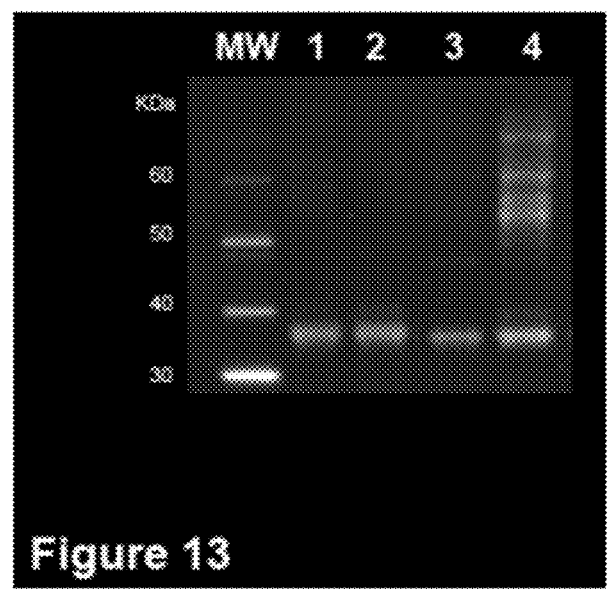

FIG. 13. Detection of C4orf32 in breast tumor tissue homogenates. Examples of tumor (lanes 3, 4) and normal samples (lanes 1, 2) stained with anti-C4orf32 antibodies. Molecular weight markers are reported on the left.

Figure 14:
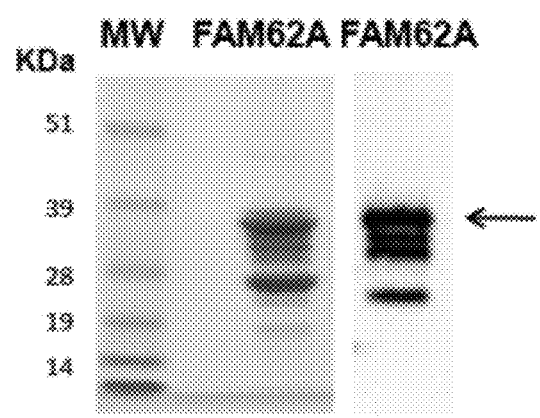

FIG. 14. Analysis of purified recombinant protein FAM62A expressed in E. coli. Left panel: Comassie staining of the purified-FAM62A protein fused to GST expressed in E. coli and separated by SDS-PAGE; Right panel: WB on the purified recombinant FAM62A protein stained with anti-FAM62A antibody. Arrow marks the protein band of the expected size. Low molecular weight bands visible on the gel correspond to degradation products of the FAM62A fusion band, as determined by mass spectrometry analysis. Molecular weight markers are reported on the left.

Figure 15:
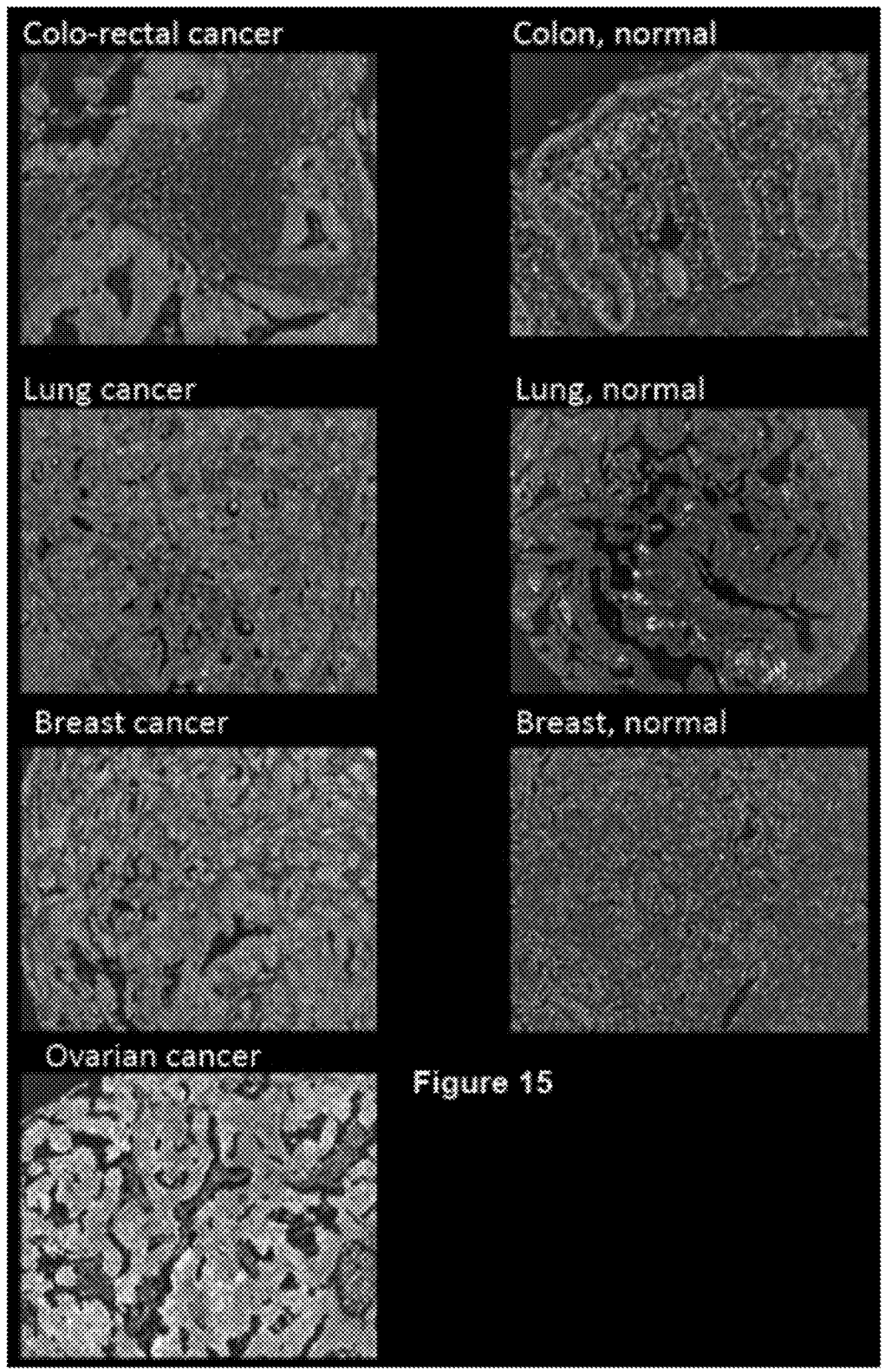

FIG. 15. Examples of immuno-histochemistry analysis of tumor (left panels) and normal tissue samples (right panels) stained with anti-FAM62A antibodies. The antibody-stains specifically tumor cells (in dark grey); negative or poor staining is visible in normal cells. In the case of the ovarian cancer, the normal tissue surrounds the tumor.

Figure 16:
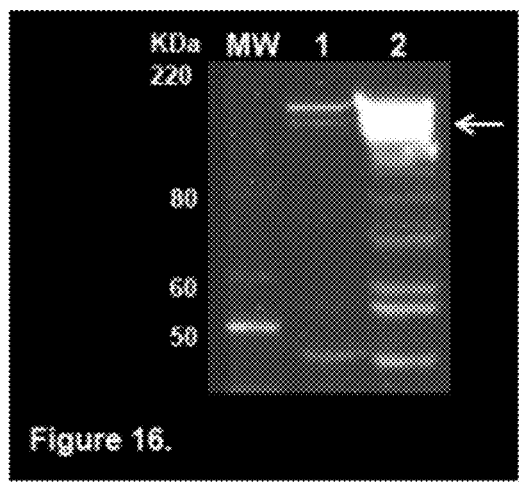

FIG. 16. FAM62A expression in transiently transfected HeLa cells. Western blot analysis of FAM62A expression in total protein extracts from HeLa cells transfected with the empty vector pcDNA3 (lane 1) or with the plasmid construct encoding the FAM62A gene (lane 2) stained with anti-FAM62A antibody. Arrow marks the expected FAM62A band. Different protein species are visible on the transfected cell extract, likely corresponding to FAM62A degradation products. Molecular weight markers are reported on the left.

Figure 17:
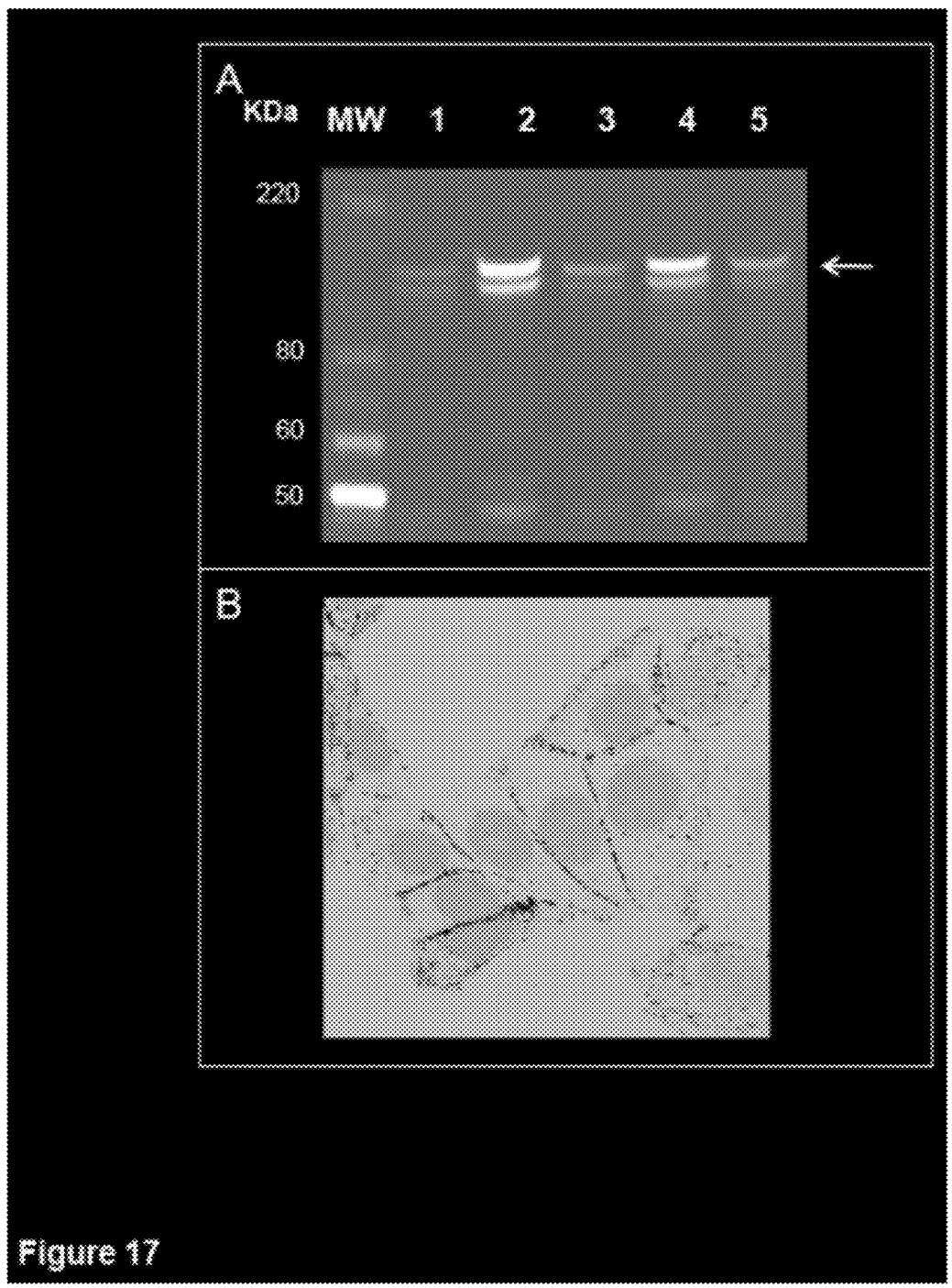

FIG. 17. FAM62A expression in tumor cell lines. Panel A) Western blot analysis. Total protein extracts from the human lung tumor cell line H-226 (lane 1), the ovarian carcinoma OVCAR-3, (lane2), the breast tumor cell lines T47D and MCF7 (lanes 3, 4) and the colon carcinoma cell line HCT-15 (lane 5), were separated by SDS-PAGE, transferred onto nitrocellulose membranes and probed with anti-FAM62A antibodies. Arrow marks the expected FAM62A band. Molecular weight markers are reported on the left. Panel B) Localization analysis. Confocal microscopy analysis of the HCT15 cell line stained with anti-FAM62A antibodies and DAPI to visualize the nuclei. The FAM62A specific staining accumulates at the plasma membrane.

Figure 18:
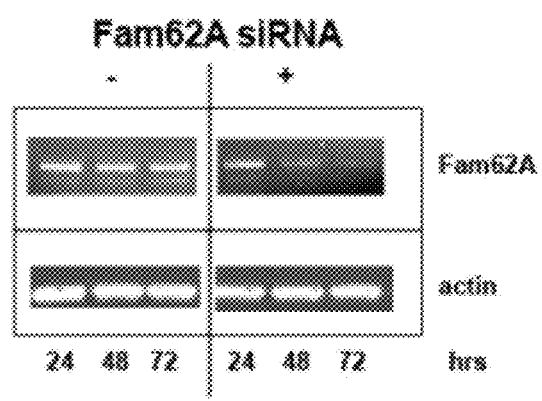

FIG. 18. Confirmation of FAM62A antibody specificity upon gene specific silencing. At different time point, total protein extracts (corresponding to $1 \times 10^6$ cells) from the breast tumor cell line MCF-7 untreated (left panel), or transfected with a FAM62A-specific siRNA (right panel), were separated by SDS-PAGE, transferred onto nitrocellulose membranes and probed with anti-actin (normalization control) or anti-FAM62A antibodies.

Figure 19:
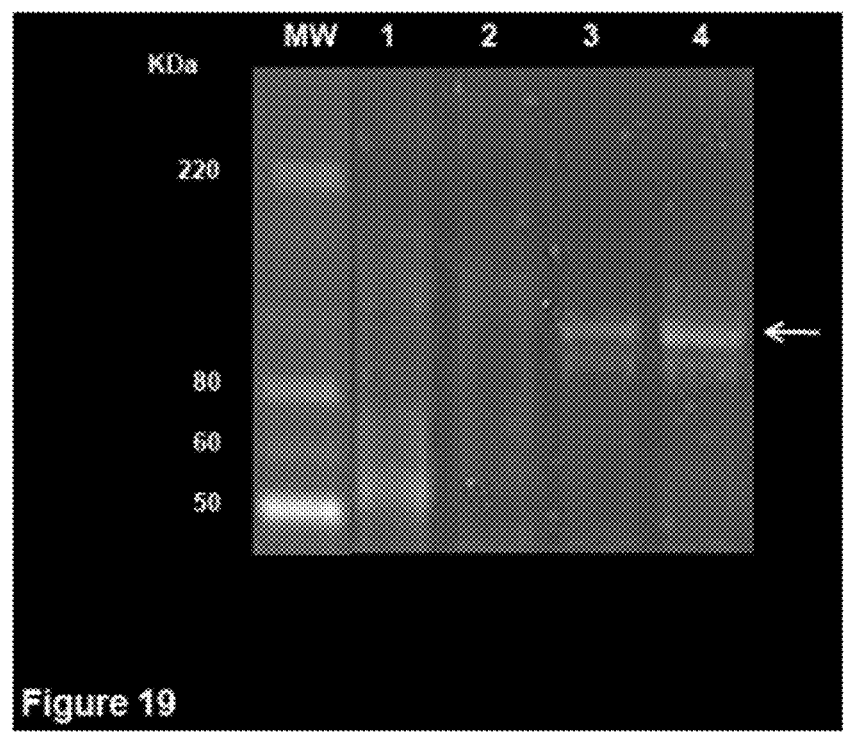

FIG. 19. Detection of FAM62A in breast tumor tissue homogenates. Examples of tumor (lanes 3, 4) and normal samples (lanes 1, 2) stained with anti-FAM62A antibodies. Molecular weight markers are reported on the left. Arrow marks the FAM62A band of expected size.

Figure 20:
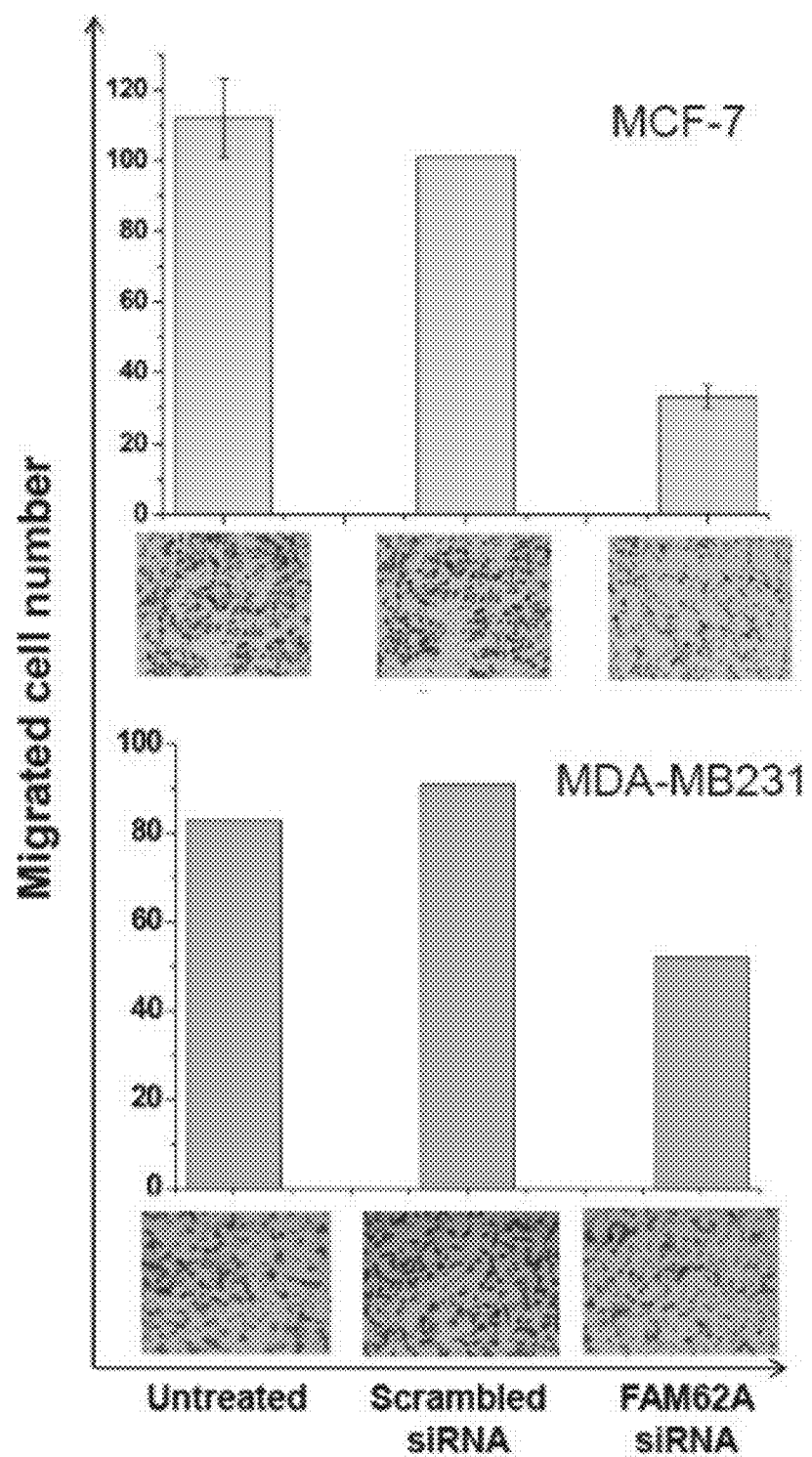

FIG. 20. FAM62A confers an invasive phenotype to breast tumor cell lines. The graphs report the effect of the siRNA-mediated inhibition of FAM62A expression on the migration activity of the MCF7 (upper graph) and the MDA-MB231 (lower graph) breast tumor cell lines, measured with the Boyden assay. As controls, cells either untreated or transfected with a scrambled siRNA were used. Small boxes under the columns show the visual counting of the migrated cells.

The following examples further illustrate the invention.

EXAMPLES

Example 1

Generation of Recombinant Human Protein Antigens and Antibodies to Identify Tumor Markers Methods The entire coding region or suitable fragments of the genes encoding the target proteins, were designed for cloning and expression using bioinformatic tools with the human genome sequence as template (Lindskog M et al (2005). Where present, the leader sequence for secretion was replaced with the ATG codon to drive the expression of the recombinant proteins in the cytoplasm of E. coli. For cloning, genes were PCR-amplified from cDNA derived from Mammalian Gene Collection (http://mgc.nci.nih.gov/) clones using specific primers so as to fuse a 6 histidine tag sequence at the 3' end, annealed to in house developed vectors, derivatives of vector pSP73 (Promega) or pGEX6PI (GE Healthcare) adapted for the T4 ligation independent cloning method (Nucleic Acids Res. 1990 Oct. 25; 18(20): 6069-6074) and used to transform E. coli NovaBlue cells recipient strain. E. coli transformants were plated onto selective LB plates containing 100 µg/ml ampicillin (LB Amp) and positive E. coli clones were identified by restriction enzyme analysis of purified plasmid followed by DNA sequence analysis. For expression, plasmids were used to transform BL21-(DE3) E. coli cells and BL21-(DE3) E. coli cells harbouring the plasmid were inoculated in ZYP-5052 growth medium (Studier, 2005) and grown at 37° C. for 24 hours. Afterwards, bacteria were collected by centrifugation, lysed into B-Per Reagent containing 1 mM MgCl2, 100 units DNAse I (Sigma), and 1 mg/ml lysozime (Sigma). After 30 min at room temperature under gentle shaking, the lysate was clarified by centrifugation at 30.000 g for 40 min at 4° C. With the exception of Fam62, all proteins were purified from the inclusion bodies by resuspending the pellet coming from lysate centrifugation in 40 mM TRIS-HCl, 1 mM TCEP {Tris(2-carboxyethyl)-phosphine hydrochloride, Pierce} and 6M guanidine hydrochloride, pH 8 and performing an IMAC in denaturing conditions. Briefly, the resuspended material was clarified by centrifugation at 30.000 g for 30 min and the supernatant was loaded on 0.5 ml columns of Ni-activated Chelating Sepharose Fast Flow (Pharmacia). The column was washed with 50 mM TRIS-HCl buffer, 1 mM TCEP, 6M urea, 60 mM imidazole, 0.5M NaCl, pH 8. Recombinant proteins were eluted with the same buffer containing 500 mM imidazole. Fam62A protein was purified as soluble GST-fusion by subjecting the B-PER soluble lysate to glutathione affinity purification using 0.5 ml mini-columns of Glutathione-Sepharose 4B resin (GE-Healthcare) equilibrated with 10 ml PBS, pH 7.4. After column washing with equilibrium buffer the proteins were eluted with 50 mM TRIS buffer, 10 mM reduced glutathione, pH 8.0. Proteins were analysed by SDS-Page and their concentration was determined by Bradford assay using the BIORAD reagent (BIO-RAD) with a bovine serum albumin standard according to the manufacturer's recommendations.

The identity of recombinant affinity purified proteins was further confirmed by tandem mass spectrometry (MS/MS), using standard procedures. This analysis also confirmed that lower mass protein species sometimes visible on the gels corresponded to truncated forms of the proteins.

To generate antisera, the purified proteins were used to immunize CD1 mice (6 week-old females, Charles River laboratories, 5 mice per group) intraperitoneally, with 3 protein doses of 20 micrograms each, at 2 week-interval. Freund's complete adjuvant was used for the first immunization, while Freund's incomplete adjuvant was used for the two booster doses. Two weeks after the last immunization animals were bleeded and sera collected from each animal was pooled.

Results

Gene fragments of the expected size were successfully isolated by PCR from specific clones of the Mammalian Gene Collection using primers specific for each gene. In particular, for the TCTN2 gene, a fragment corresponding to nucleotides 637-1458 of the transcript (SEQ ID 28) of and encoding an amino acid region from 171 to 444 (SEQ ID 9) was obtained. For the TCTN1 gene, a fragment corresponding to nucleotides 134 to 1789 of the transcript (SEQ ID NO 23, corresponding to ENST00000397655) of and encoding an amino acid region from 22 to 573 (SEQ ID NO 5, corresponding to ENSP00000380775) was obtained. For the TCTN3 gene, a fragment corresponding to nucleotides 311 to 2065 of the transcript (SEQ ID NO 32, corresponding to ENST00000371217) of and encoding an amino acid region from 23 to 607 (SEQ ID NO 13, corresponding to ENSP00000360261) was obtained.

For the HIGD2A gene, a fragment corresponding to nucleotides 49-366 of the transcript (SEQ ID 9) of and encoding an amino acid region from 1 to 106 (SEQ ID 2) was obtained. For HIGD2B gene, a fragment corresponding to nucleotides 525-852 of the transcript (SEQ ID 10) of and encoding an amino acid region from 1 to 106 (SEQ ID 3) was obtained.

For the C4orf32, a fragment corresponding to nucleotides 60-374 of the transcript (SEQ ID 11) of and encoding an amino acid region from 1 to 105 (SEQ ID 4) was obtained.

For the FAM62A, a fragment corresponding to nucleotides 53-257 of the transcript SEQ IDs 12) and encoding an amino acid region from 1 to 68 (SEQ IDs 5) was obtained. This fragment is identical in all available FAM62A isoforms (protein SEQ IDs 5, 6, 7; Transcript SEQ IDs: 12, 13, 14).

A clone encoding the correct amino acid sequence was identified for each gene/gene fragment and, upon expression in *E. coli*, a protein of the correct size was produced and subsequently purified using affinity chromatography (FIGS. 1, 5, 10, 14, left panel). In the case of TCTN3, different truncated forms of the protein were obtained after purification, among which a protein product of approximately 38 KDa was the major form recognized by the antibodies (FIG. 1B). Antibodies generated by immunization specifically recognized their target proteins in Western blot (WB) (FIGS. 1, 5, 10, 14 right panel). Moreover, antibodies raised against TCTN2—also recognized TCTN1 and TCTN3. Similarly, antibodies raised against HIGD2A and HIGD2B were able to recognize HIGD2A in the assay.

Example 2

Tissue Profiling by Immune-Hystochemistry

Methods

The analysis of the antibodies capability to recognize their target proteins in tumor samples was carried out by Tissue Micro Array (TMA), a miniaturized immuno-histochemistry technology suitable for HTP analysis that allows to analyse the antibody immuno-reactivity simultaneously on different tissue samples immobilized on a microscope slide.

A tissue microarray was prepared containing 100 formalin-fixed paraffin-embedded cores of human tissues from patients affected by colorectal cancer, ovarian cancer, breast cancer, lung cancer, prostate cancer and corresponding normal tissues and analyzed using the specific antibody sample. Briefly, each TMA slide included tumor tissue samples representative of different well pedigreed patients, representing the 5 cancer types, and an equal number of normal tissue samples from the same patients as controls. In total, the TMA design consisted in 10 tumor samples per each tumor class and 10 normal tissue from 5 well pedigreed patients (equal to two tumor samples and 2 normal tissues from each patient) to identify promising target molecules differentially expressed in cancer and normal tissues. The direct comparison between tumor and normal tissues of each patient allowed the identification of antibodies that stain tumor cells and provide indication of target expression in the tumor under investigation.

All formalin fixed, paraffin embedded tissues used as donor blocks for TMA production were selected from the archives at the TEO (European Institute of Oncology, Milan). Corresponding whole tissue sections were examined to confirm diagnosis and tumour classification, and to select representative areas in donor blocks. Normal tissues were defined as microscopically normal (non-neoplastic) and were generally selected from specimens collected from the vicinity of surgically removed tumors. The TMA production was performed essentially as previously described (7, 8). Briefly, a hole was made in the recipient TMA block. A cylindrical core tissue sample (1 mm in diameter) from the donor block was acquired and deposited in the recipient TMA block. This was repeated in an automated tissue arrayer "Galileo TMA CK 3500" (BioRep—Milan) until a complete TMA design was produced. TMA recipient blocks were baked at 42° C. for 2 h prior to sectioning. The TMA blocks were sectioned with 2-3 μm thickness using a waterfall microtome (Leica), and placed onto poli-L-lysinated glass slides for immunohistochemical analysis. Automated immunohistochemistry was performed as previously described (Kampf C. et al. 2004 Clin. Proteomics 1: 285-300). In brief, the glass slides were incubated for 30' min in 60° C., de-paraffinized in xylene (2×15 min) using the Bio-Clear solution (Midway. Scientific, Melbourne, Australia), and re-hydrated in graded alcohols. For antigen retrieval, slides were immersed 0.01 M Na-citrate buffer, pH 6.0 at 99° C. for 30 min Slides were placed in the Autostainer® (DakoCytomation) and endogenous peroxidase was initially blocked with 3% H2O2, for 5 min. Slides were then blocked in Dako Cytomation Wash Buffer containing 5% Bovine serum albumin (BSA) and subsequently incubated with mouse antibodies for 30' (dilution 1:200 in Dako Real™ dilution buffer). After washing with DakoCytomation wash buffer, slides were incubated with the goat anti-mouse peroxidase conjugated Envision® for 30 min each at room temperature (DakoCytomation). Finally, diaminobenzidine (DakoCytomation) was used as chromogen and Harris hematoxylin (Sigma-Aldrich) was used for counterstaining. The slides were mounted with Pertex® (Histolab).

The staining results have been evaluated by a trained pathologist at the light microscope, and scored according to both the percentage of immunostained cells and the intensity of staining. The individual values and the combined score (from 0 to 300) were recorded in a custom-tailored database. Digital images of the immunocytochemical findings have been taken at a Leica DM LB light microscope, equipped with a Leica DFC289 color camera.

Results

A TMA design was obtained, representing tumor tissue samples from 5 tumor classes (lung, ovary, prostate, breast and colon) and normal tissues, derived from 5 patients for each tumor type. The results from tissue profiling showed that the antibodies specific for the recombinant proteins (see Example 2) are strongly immunoreactive on several cancer tissues, indicating the presence of the target proteins in tumors tissues, while no or poor reactivity was detected in normal tissues. Based on this finding, the detection of target proteins in tissue samples can be associated with the specific tumor/s.

The capability of target-specific antibodies to stain different tumor tissues is summarized in Table 1. Representative examples of microscopic enlargements of tissue samples stained by each antibody are reported within FIGS. 2, 6, 11, 15.

The capability of marker-specific antibodies to stain different tumor tissues is summarized in Table 2, which reports the percentage of positive tumor tissue samples derived from the 50 patients

TABLE 2

| Target protein | Percentage of tumor tissues showing positive immuno-istochemistry staining | | | | |
|---|---|---|---|---|---|
| | Breast | Colon | Lung | Ovary | Prostate |
| Tectonic 2 | na | 90 | 75 | 25 | na |
| HIGD2A | na | 40 | na | 45 | na |
| C4orf32 | 52 | na | 82 | na | na |
| FAM62A | 86 | 74 | 96 | 75 | na | na: not applicable

Example 4

Expression and Localization of the Target Proteins in Transfected Mammalian Cells Methods The specificity of the antibodies for each target proteins was assessed by Western blot analysis on total protein extracts

TABLE 1

TUMOR MARKERS IDENTIFIED BY TMA

| | POSITIVE TUMOR TISSUES OF PATIENTS TESTED BY TMA | | | | | |
|---|---|---|---|---|---|---|
| TARGET PROTEIN | BREAST | COLON | LUNG | OVARY | PROSTATE | BIOLOGICAL INFORMATION |
| TECTONIC-2 | 0/5 | 5/5 | 3/5 | 2/5 | 0/5 | FUNCTION: UNKNOWN FUNCTION LOCATION: MEMBRANE |
| HIGD2A | 0/5 | 2/5 | 0/5 | 3/5 | 0/5 | FUNCTION: HYPOXIA INDUCED PROTEIN LOCATION: MEMBRANE |
| CHR 4 ORF 32 | 2/5 | 0/5 | 2/5 | 0/5 | 0/5 | FUNCTION: UNKNOWN FUNCTION LOCATION: MEMBRANE |
| FAM 62A | 3/5 | 3/5 | 1/5 | 4/5 | 0/5 | FUNCTION: RHODOPSIN-LIKE RECEPTOR ACTIVITY, G-PROTEIN COUPLED RECEPTOR LOCATION: PLASMATIC MEMBRANE |

Example 3

Confirmation of the Marker Association with the Tumor/s by Expanded TMA Analysis Method The association of each protein with the indicated tumors was further confirmed on a larger collection of clinical samples. To this aim, a tissue microarray was prepared for each of the five tumor classes containing 100 formalin-fixed paraffin-embedded cores of human tissues from 50 patients (equal to two tissue samples from each patient). The TMAs were stained with the marker specific antibodies, using the previously reported procedure. The staining results were evaluated, as above described, by a trained pathologist at the light microscope.

Results

Five TMA designs were obtained, for each of the five tumors, representing tissue samples from 50 patients. The results from tissue analysis showed that the antibodies specific for each of the four proteins (see Example 1) are strongly immune-reactive on a large percentage of tumor tissues, indicating that the corresponding proteins are selectively detected in the tumor/s. This finding confirms a strong association of the markers with the specific tumor/s.

from eukaryotic cells transiently transfected with plasmid constructs containing the complete sequences of the genes encoding the target proteins.

To this aim, cDNA were generated from pools of total RNA derived from human testis, human placenta, human bone marrow, human fetal brain, in reverse transcription reactions and the entire coding regions were PCR-amplified with specific primers pairs. PCR products were cloned into plasmid pcDNA3 (Invitrogen). In the case of C4Orf32, the PCR product was also cloned into plasmid pcDNA3.1D (Invitrogen) to express a tagged form of the protein fused to a V5 epitope sequence at the carboxy-terminus. HeLa cells were grown in DMEM-10% FCS supplemented with 1 mM Glutamine were transiently transfected with preparation of the resulting plasmids and with the empty vector as negative control using the Lipofectamine-2000 transfection reagent (Invitrogen). After 48 hours, cells were collected, lysed with PBS buffer containing 1% Triton X100 and expression of target proteins was assessed by Western blot analysis on total cell extracts (corresponding to $1 \times 10^6$ cells) using antibodies specific for TCTN2, C4orf32, FAM62A, HIGD2A, and its homologous HIGD2B protein. When the C4orf32 tagged construct was used for transfection, blots were analysed with a tag-specific antibody (anti-V5 antibody). Western blot was performed by separation of the protein extracts on pre-cast SDS-PAGE gradient gels (NuPage 4-12% Bis-Tris gel, Invitrogen) under reducing conditions, followed by electro-transfer to nitrocellulose membranes (Invitrogen) according to the manufacturer's recommendations. The membranes were blocked in blocking buffer composed of 1×PBS-0.1% Tween 20 (PBST) added with 10% dry milk, for 1 h at room temperature, incubated with the antibody diluted 1:2500 in blocking buffer containing 1% dry milk and washed in PBST-1%. The secondary HRP-conjugated antibody (goat anti-mouse immunoglobulin/HRP, Perkin Elmer) was diluted 1:5000 in blocking buffer and chemiluminescence detection was carried out using a Chemidoc-IT UVP CCD camera (UVP) and the Western Lightning™ cheminulescence Reagent Plus (Perkin Elmer), according to the manufacturer's protocol.

Surface localization of target proteins was assessed in HeLa transfected cells by cell surface staining and Flow Cytometry (FACS) analysis. HeLa cells transfected with each construct or with the empty vector ($2 \times 10^4$ per well) were pelletted in 96 U-bottom microplates by centrifugation at 200×g for 5 min at 4° C. and incubated for 1 hour at 4° C. with the appropriate dilutions of marker-specific antibodies. The cells were washed twice in PBS-5% FCS and incubated for 20 min with the appropriate dilution of R-Phycoerythrin (PE)-conjugated secondary antibodies (Jackson Immuno Research, PA, USA) at 4° C. After washing, bacteria were analysed by a FACS Canto II flow cytometer (Becton Dickinson). Data were analyzed with FlowJo 8.3.3 program.

Results

To confirm the antibody specificity, the complete coding sequence/s for each target protein were cloned in a eukaryotic expression vector and used for transient transfection of HeLa cells.

Expression of each protein was detected by Western blot in total protein extracts from HeLa cells transfected with the different constructs encoding for the target proteins using their specific antibodies. As far as TCTN2, HIGD2A and FAM62A are concerned, a band of the expected size was visible in HeLa cells transfected with the corresponding plasmids while the same band was either not visible or very faintly detected in HeLa cells transfected with the empty pcDNA3 plasmid. Each antibody recognized specifically its target protein, since almost a unique single protein band was detected. Results are reported in FIGS. 3A, 7 and 16.

Figure 7:
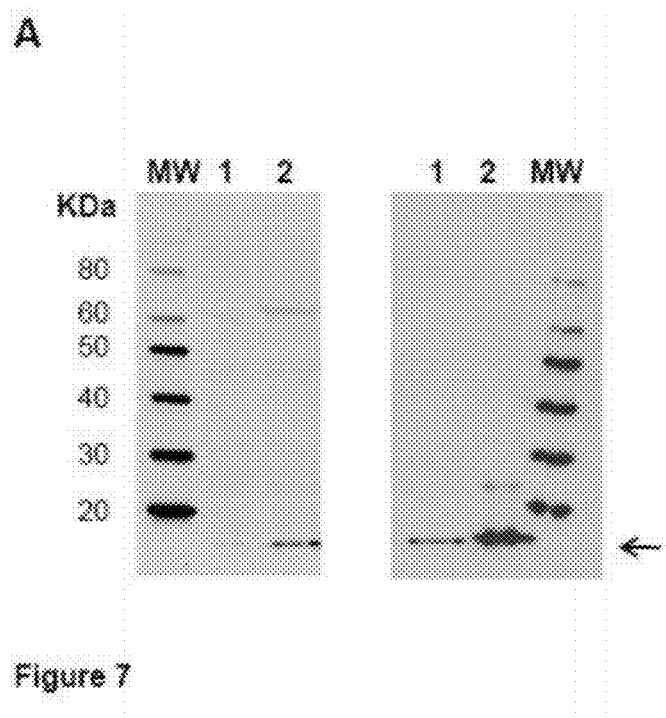
FIG. 7. HIGD2A expression in transiently transfected HeLa cells. Western blot analysis of HIGD2A expression in total protein extracts from HeLa cells transfected with the empty vector pcDNA3 (lane 1) or with the plasmid construct encoding the HIGD2A gene (lane 2) stained with anti-HIGD2A (right panel) and anti-HIGD2B (left panel) antibodies. Arrow marks the expected HIGD2A band. Molecular weight markers are reported on both sides.

HeLa cells transfected with the HIGD2A construct were also tested with the antibody specific for the HIGD2B homolog. Results show that the anti-HIGD2B antibody was capable of detecting HIGD2A protein in transfected cells. (FIG. 7).

As regards C4orf32, HeLa were transfected with the C4orf32 untagged and tagged constructs and tested with the C4orf32- and the anti-V5 antibodies. A protein of expected size was detected in HeLa cells transfected with the tagged construct using both antibodies. A protein band of higher mass was detected in cells transfected with the untagged construct using the C4orf32-specific antibody. This indicates that the native C4orf32 protein forms highly stable aggregates that are detected by the antibody in immunoblot. The presence of the fusion tag at the C4orf32 carboxy-terminus appears to prevent the C4orf32 aggregation and allows the detection of the protein species with the expected mass. Results of immunoblot analysed with the C4orf32 antibody is reported in FIG. 12. Data obtained with the anti-V5 antibody are not shown.

Figure 1:
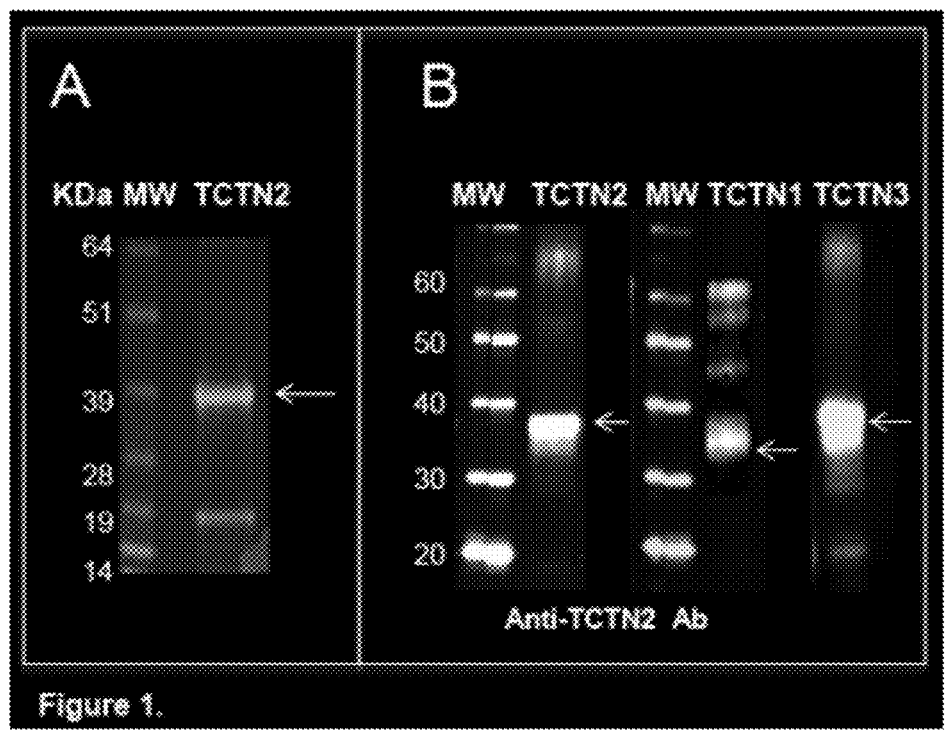
FIG. 1. Analysis of purified recombinant Tectonic family proteins with specific antibodies. Panel A: Comassie staining of recombinant purified His-tag TCTN2 fusion proteins after separation by SDS-PAGE; Panel B: WB on the purified recombinant TCTN2, TCTN1 or TCTN3 proteins stained with anti-TCTN2 antibodies. Arrows mark the protein bands of the expected size. Molecular weight markers are reported on the left of each panel.
Figure 2:
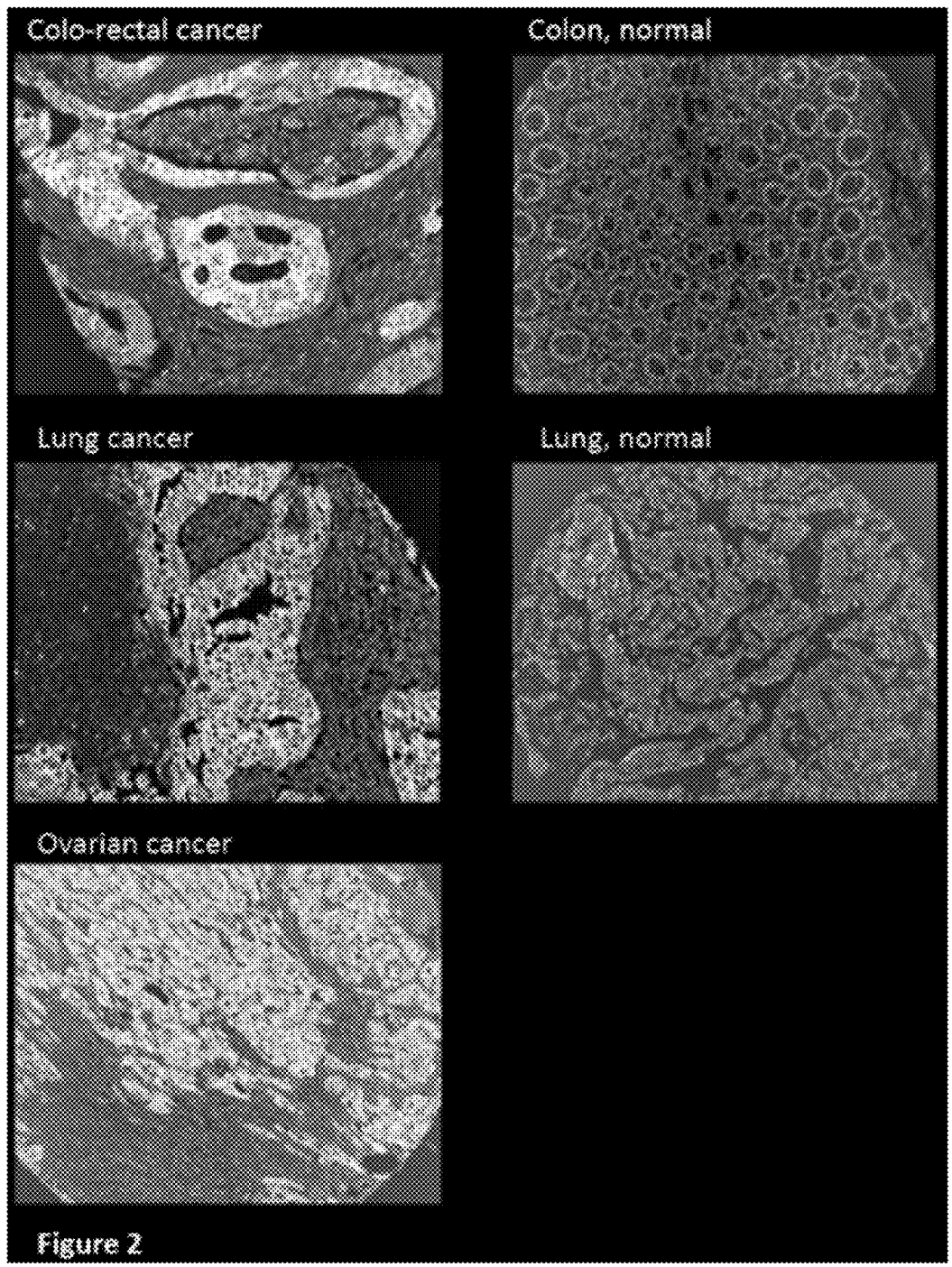
FIG. 2. Examples of immuno-histochemistry analysis of tumor (left panels) and normal tissue samples (right panels) stained with anti-TCTN2 antibodies. In the case of the ovarian cancer, the normal tissue surrounds the tumor. The antibody-stains specifically tumor cells (in dark grey); negative or poor staining is visible in normal cells.
Figure 3:
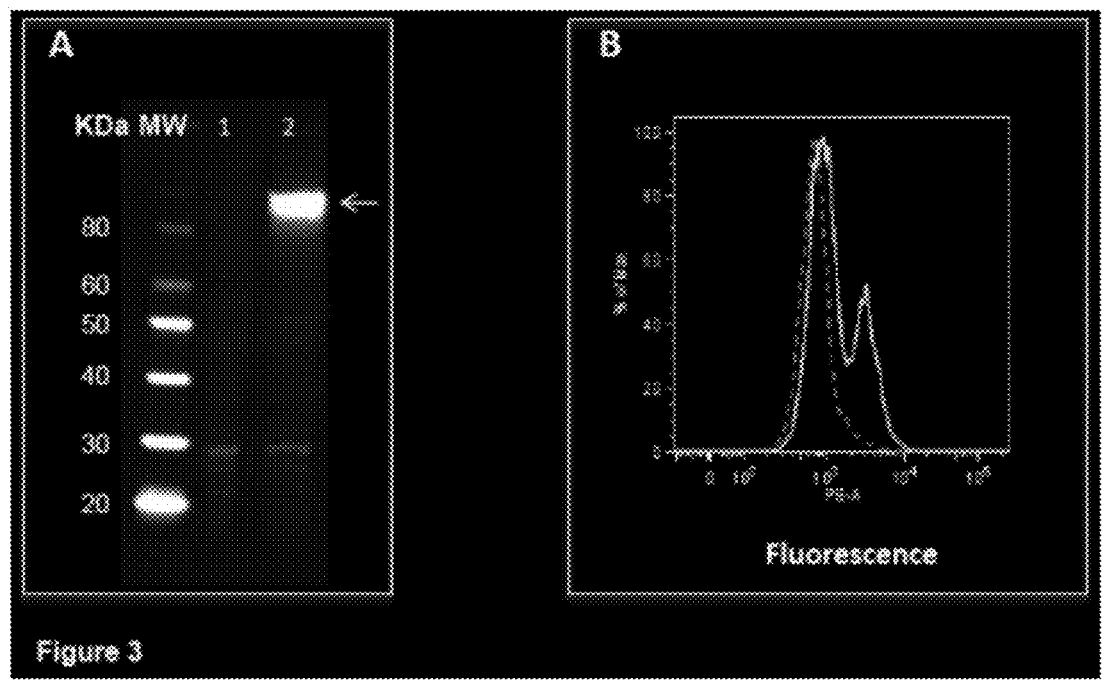
FIG. 3. TCTN2 expression in transiently transfected HeLa cells. Panel A) Western blot analysis of TCTN2 expression in total protein extracts from HeLa cells transfected with the empty vector pcDNA3 (lane 1) or with the plasmid encoding the TCTN2 gene (lane 2) stained with anti-TCTN2 antibody. Arrow marks the expected TCTN2 band. Molecular weight markers are reported on the left. Panel B) Flow cytometry analysis of TCTN2 surface localization in HeLa cells transfected with the empty vector pcDNA3 (dashed peak) or with the plasmid construct encoding the TCTN2 gene (solid peak). X axys, Fluorescence scale; Y axys, Cells (expressed as % relatively to major peaks).

Surface localization of target proteins was addressed by FACS analysis of transiently transfected cells stained with the specific antibodies. Data are reported for cells transfected with the construct encoding TCTN2. In this experiment the TCTN2-antibody was capable of binding the surface of transfected cells, while no binding was observed on cells transfected with the empty pcDNA3 vector (FIG. 3B). This indicates that this target protein is localized on the cell surface and are accessible to the external environment. This finding reinforces the relevance of TCTN2 protein for future development as either diagnostic marker or therapeutic targets.

Example 5

Expression of Target Proteins in Tumor Cell Lines

Expression of target proteins showing positivity by TMA was also assessed by WB on total extracts from a panel of human epithelial cell lines derived from the same tumor types. In each analysis, cells were cultured in under ATCC recommended conditions, and sub-confluent cell mono-layers were detached with PBS-0.5 mM EDTA and lysed by several freeze-thaw passages in PBS-1% Triton. Total protein extracts were loaded on SDS-PAGE ($2 \times 10^5$ cells/lane), and subjected to WB with specific antibodies as described above.

The marker cellular localization was assessed by confocal microscopy analysis. Cells were plated on glass cover slips and after 48 h were washed with PBS and fixed with 3% formaldehyde solution in PBS for 20 min at RT. Then, after extensive washing in PBS, the cells were permeabilized with 0.01% BriJ96® (Fluka), and incubated overnight at 4° C. with polyclonal antibodies (1:200). Cells were then stained with Alexafluor 488-labeled goat anti-mouse antibodies (Molecular Probes). DAPI (Molecular Probes) was used to visualize nuclei. The cells were mounted with glycerol plastine and observed under a laser-scanning confocal microscope (LeicaSP5).

Results

Expression analysis of the target proteins was confirmed in tumor cell lines. Example data are shown for HIGD2A and FAM62A.

In particular, HIGD2A expression is reported for a panel of the tumor cell lines including Ovcar 3 (ovary adenocarcinoma), and HCT-15 and Colo205 (colon tumor cell lines) and MDA-MB231 (breast adenocarcinoma). FAM62A expression analysis is reported for the tumor cell lines H226, Ovcar 3, MCF7 and T47D (breast adenocarcinoma).

HIGD2A and FAM62A protein bands of the expected sizes were detected in total protein extracts of all tested tumor cell lines by immunoblot, confirming their expression in tumor cells derived from the different tumor types.

Figure 8:
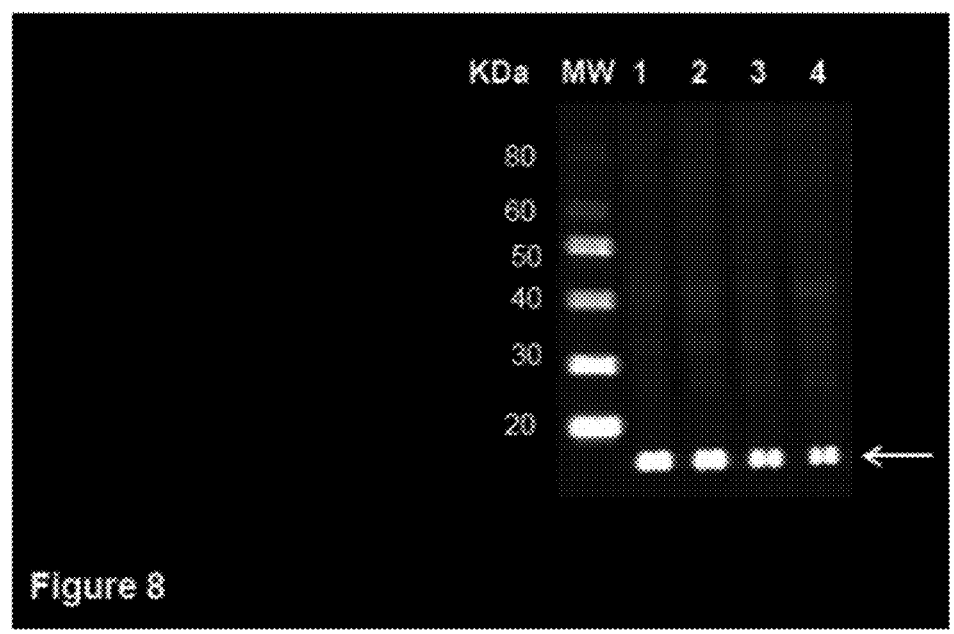
FIG. 8. HIGD2A expression in tumor cell lines by Western blot. Total protein extracts from the human colon carcinoma tumor cell lines Colo205 (lane 1) and HCT-15 (lane 2), the ovarian carcinoma OVCAR-3 (lane 3) and the breast tumor cell line MDA-MB231 (lane 4) were separated by SDS-PAGE, transferred onto nitrocellulose membranes and probed with anti-HIGD2A antibodies. Arrow marks the expected HIGD2A band. Molecular weight markers are reported on the left FIG. 9. Confirmation of HIGD2A antibody specificity upon gene specific silencing. At different time points, total protein extracts (corresponding to $1\times10^6$ cells) from the breast tumor cell line MDA-MB231 either untreated (left panel) or transfected with a HIGD2A-siRNA (right panel) were separated by SDS-PAGE, transferred onto nitrocellulose membranes and probed with anti-HIGD2A antibodies. As normalization control, membranes were also probed with an anti-actin antibody.

Results are reported in FIGS. 8, 17A.

Confocal microscopy analysis of the HCT-15 cell with anti-FAM62A antibody shows that the protein is localized at the plasma membrane (FIG. 17B). This suggests that the protein is accessible to the external environment and reinforces its relevance for future development as either diagnostic marker or therapeutic targets.

Example 6

Confirmation of the Specificity the Tumor-Reactive Antibodies by Gene Silencing Experiments Methods The specificity of the polyclonal antibodies for their targets was also confirmed by transient RNA-interference experiments, measuring the loss of detection of the expected protein bands in cell lines upon silencing. For each gene, a set of small interfering RNAs (siRNAs) and controls were obtained from QIAGEN, whose target sequence is reported in Table 3.

TABLE 3

| NCBI gene | mRNA Accessions | siRNA Target Sequence |
|---|---|---|
| TCTN1 | NM_001082537<br>NM_001082538<br>NM_024549 | TTGAACTTGTTGACCAGATTA<br>TTGCGTGAATGTTGTTCTTGA |
| TCTN2 | NM_024809 | TGCATCCGTCCAGTTTATTAA<br>AAGCCTATAGTTAGACAACCA<br>TGGCTCGAAATAATACGTGTA<br>TTGGAACTATACCAAGAACGA |
| TCTN3 | NM_001013840<br>NM_015631 | TTGGCTCTGACTGATGATATA<br>AACCCGCAAGCTCATGTATCA<br>CAGGATTCTCAGCAAGTTACA |
| HIGD2A | NM_138820 | CACGGCGGCCGCCCTCACCTA<br>CTCCGCAGAAATGATTCCAAA<br>ATCCTAGATGCTGTTGTTTGA |
| C4orf32 | NM_152400 | TTGGACCTAGACCTACTTTAA<br>CCCAGCCTAAACTAAGGTAAA<br>AACGAATAGTGGAACCAGTAA |
| FAM62A | NM_015292 | GTGGGAGATAGTTCTCATAAA<br>ACGCCCGACCCTAGACATCAA |

The expression of marker genes was knocked down in a panel of epithelial tumor cell lines using marker-specific siRNAs with the HiPerfect transfection reagent (QIAGEN) following the manufacturer's protocol. As control, cells treated with irrelevant siRNA (scrambled siRNA) were analysed in parallel. At different time points (ranging from 24 to 72 hours) post transfection, we first assessed the reduction of gene transcription by quantitative RT-PCR (QRT-PCR) on total RNA, by evaluating the relative marker transcript level, using the beta-actin, GAPDH or MAPK genes as internal normalization control. Afterwards, the loss of protein expression was also confirmed by immunoblot on total protein extracts prepared from the siRNA-treated cell lines, using the same antibodies giving positive immune-staining on tumor tissues. Blots were also probed with an anti-actin antibody as internal normalization control.

Results

Figure 9:
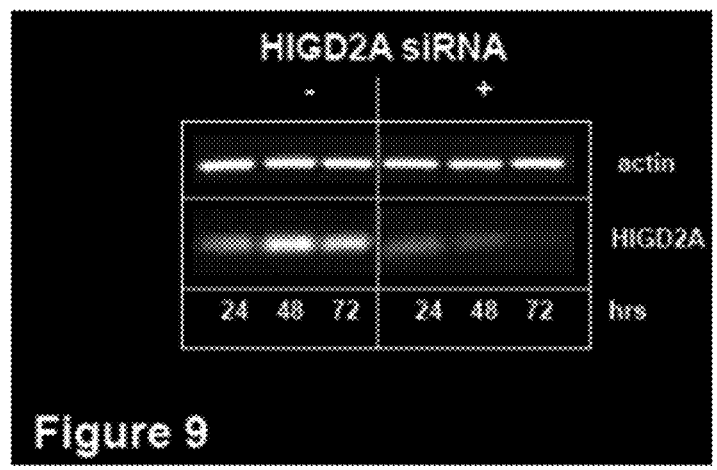
Figure 10:
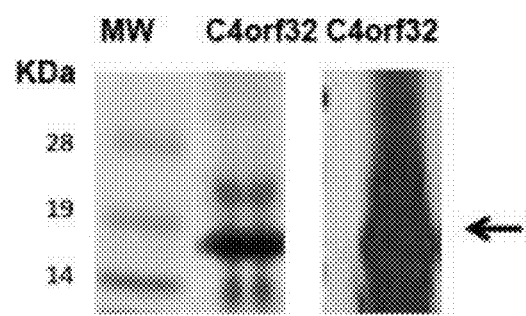
FIG. 10. Analysis of purified C4orf32 recombinant protein expressed in *E. coli*. Left panel: Comassie staining of purified His-tag C4orf32 fusion protein expressed in *E. coli* separated by SDS-PAGE; Right panel: WB on the purified recombinant C4orf32 protein stained with anti-C4orf32 antibody. Arrow marks the protein band of the expected size. Molecular weight markers are reported on the left.
Figure 11:
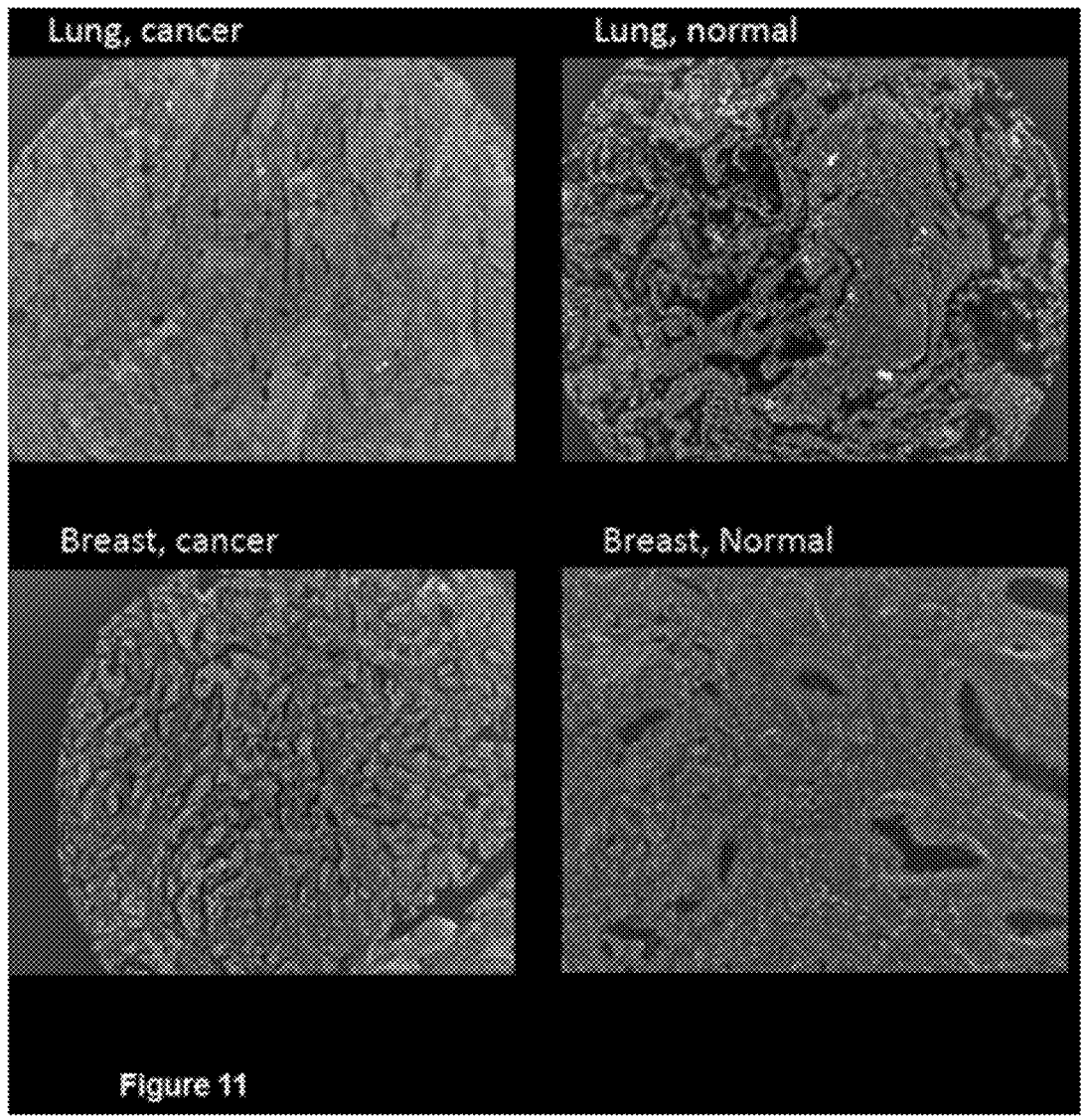
FIG. 11. Examples of immuno-histochemistry analysis of tumor (left panels) and normal tissue samples (right panels)

Gene silencing experiments with marker-specific siRNA reduced the marker transcripts (approximately 30-40 fold reduction), as determined by Q-RT-PCR. Under this condition, immunoblot analysis with marker-specific antibodies revealed that expression of protein bands of expected size were clearly detected in untreated cell lines while they were significantly reduced upon si-RNA treatment. Examples of this analysis are reported for HIGD2A and FAM62A in FIGS. 9 and 18, respectively.

Examples 7

The Tumor-Reactive Antibodies are Able to Recognize Proteins of Expected Size in Tumor Tissue Homogenates The presence of protein bands corresponding to the marker proteins was also investigated in tissue homogenates of tumor biopsies from patients affected by tumor (selected from the 5 tumor classes). In these assay, tumor and normal tissues from the same patients were analysed in parallel. Homogenates were prepared by mechanic tissue disruption in buffer containing 40 mM TRIS-HCl, 1 mM TCEP {Tris(2-carboxyethyl)-phosphine hydrochloride, Pierce} and 6M guanidine hydrochloride, pH 8. Western blot was performed by separation of the total protein extracts (20 µg/lane) proteins were detected by specific antibodies.

Results

All tested antibodies specifically recognized protein species on tumor tissues, while the same bands were not or faintly visible on normal tissues. Example data are represented for proteins FAM62A and C4orf32 on breast tissue homogenates. As shown in FIG. 19, in the case of FAM62A a band of expected size was detected in breast tumor tissues, while no bands were detected in normal tissue homogenates, confirming the presence of the marker proteins in the tumor. As far as C4orf32 is concerned, different protein species with higher mass (50-60 KDa) were detected by the antibody specifically in tumor samples (FIG. 13). This is in line with previous evidences indicating the tendency of the C4orf32 protein to form stable aggregates (see Example 4).

Example 8

The Marker Proteins are Involved in Cell Malignant Phenotypes

To verify that the proteins included in the present invention can be exploited as targets for therapeutic applications, the effect of alteration of marker expression, either depletion or over-expression (obtained upon transfection with specific siRNAs or expression plasmids, respectively), was evaluated in in vitro studies generally used to define the role of newly discovered proteins in tumorigenesis or tumor progression. Marker-specific knock-down or transfected tumor cell lines and their respective controls were analysed for their migration property and the ability to proliferate in an anchorage-independent fashion using the Boyden in vitro invasion and the soft agar assays, respectively. A brief description of these assays is provided below.

The Boyden chamber assay is based on a chamber of two medium-filled compartments separated by a microporous membrane. Cells are placed in the upper compartment and are allowed to migrate through the pores of the membrane into the lower compartment, in which chemotactic agents are present. After an appropriate incubation time, the membrane between the two compartments is fixed and stained, and the number of cells that have migrated to the lower side of the membrane is determined. Therefore, the Boyden chamber-based cell migration assay has also been called filter membrane migration assay, trans-well migration assay, or chemotaxis assay.

The Soft Agar Assay for Colony Formation is an anchorage independent growth assay in soft agar, which is considered the most stringent assay for detecting malignant transformation of cells. Many primary cell lines must attach to a solid surface before they can divide and proliferate, while they fail to grow when suspended in a viscous fluid or gel (e.g. agar or agarose). However, when these cell lines are transformed, they are able to grow in a viscous fluid or gel and become anchorage-independent. The process, by which these phenotypic changes occur, is assumed to be closely related to the process of in vivo carcinogenesis. Thereby, the acquisition of an anchorage independent growth style on soft agar is viewed as indicative of in vivo carcinogenesis. For this assay, cells are cultured with appropriate controls in soft agar medium for 21-28 days. Following this incubation period, formed colonies can either be analyzed morphologically using cell stain and quantifying the number of colonies formed per well.

Method

When the effect of marker depletion was analysed, tumor cell lines previously shown to express the proteins were treated with any of the marker specific siRNA molecules proved to inhibit marker expression (see Table 3 in the Example 6) and then tested in the Boyden invasion and the anchorage independent soft agar assays, as compared to control cell lines treated with a scramble siRNA. When the effect of marker overexpression was assessed, tumor cell lines showing a low endogenous marker expression were transfected with corresponding pcDNA3-derived plasmids and then tested in the Boyden and the soft agar assays.

For the Boyden in vitro invasion assay, a transwell system, equipped with 8-μm pore polyvinylpyrrolidone-free polycarbonate filters, was used. The upper sides of the porous polycarbonate filters were coated with 50 μg/cm$^2$ of reconstituted Matrigel basement membrane and placed into six-well culture dishes containing complete growth medium. Cells ($1 \times 10^4$ cells/well) were loaded into the upper compartment in serum-free growth medium. After 16 h of incubation at 37° C., non invading cells were removed mechanically using cotton swabs, and the microporous membrane was stained with Diff-Quick solution. Chemotaxis was evaluated by counting the cells migrated to the lower surface of the polycarbonate filters (six randomly chosen fields, mean±SD).

For the anchorage independent soft agar assay, cells were suspended in growth medium containing 10% FBS and 0.3% agar, seeded onto a solidified base of growth medium containing 0.6% agar, and overlaid with growth medium. Cell growth was monitored for 2 weeks by scoring the formation of colonies (all values were determined in triplicate). Photographs were taken with a phase-contrast microscope.

Results

Figure 4:
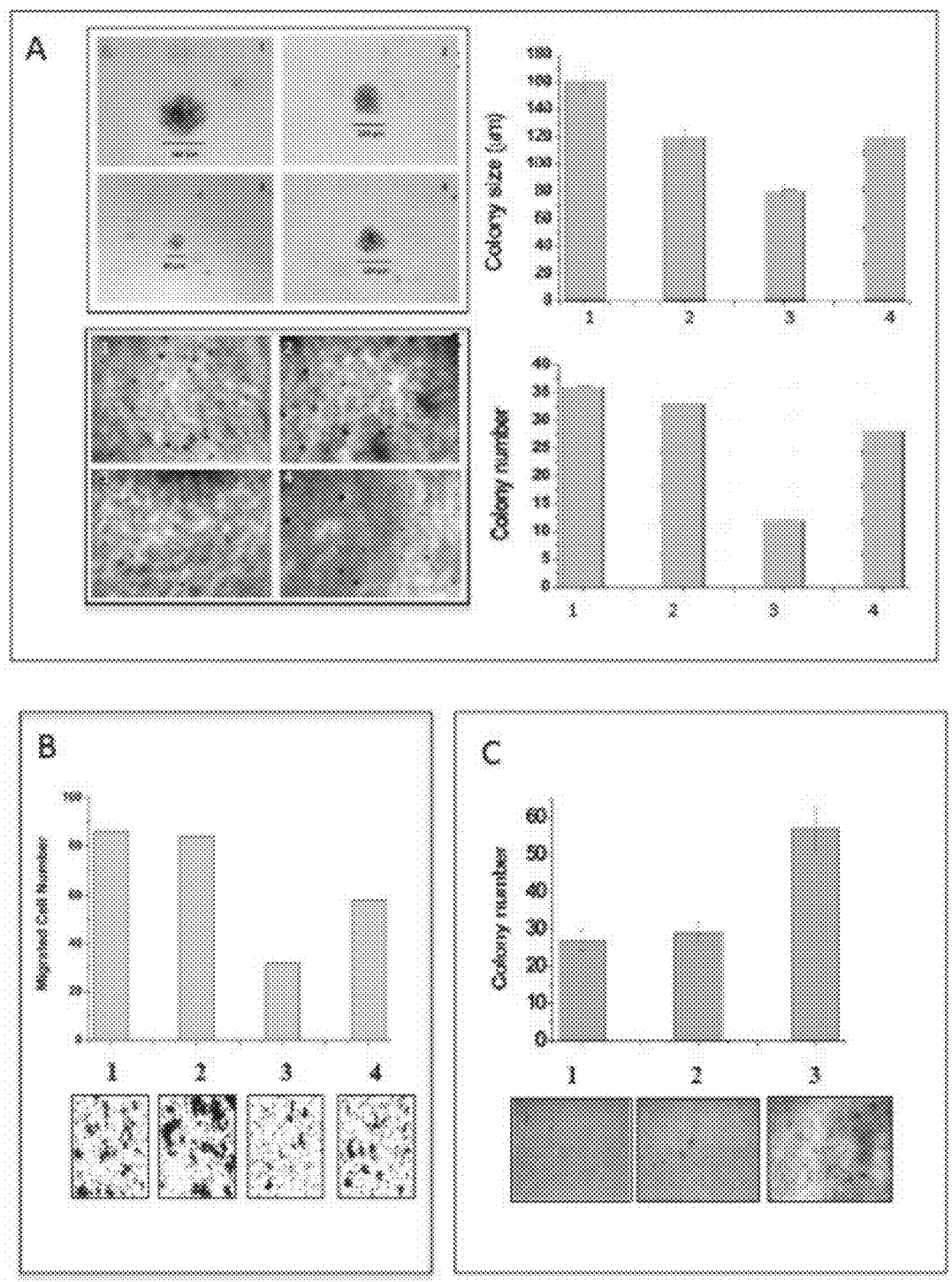
FIG. 4. TCTN1, TCTN2 and TCTN3 confer malignant cell phenotypes Panel A. Silencing of either TCTN1 or TCTN3 impairs the clonogenic phenotype of the cell line HCT15 grown on soft agar. The graphs show the reduction of the size (upper panels) and number (lower panels) of colonies formed by HCT15 cells upon transfection with either TCTN1-siRNA (3) or TCTN3-siRNAs (4) compared to cells transfected with a scrambled siRNA (2) or untreated cells (1). A picture of the colonies formed under each condition are reported on the left of the graphs. Panel B. Silencing of either TCTN1 or TCTN3 reduces the invasive phenotype of the HCT15 colon cell line. The graph reports the effect of the siRNA mediated inhibition of TCTN1 or TCTN3 expression on the migration activity of the HCT-15 colon tumor cell line, measured with the Boyden assay. As controls, untransfected cells or cells transfected with a scrambled siRNA were used. Small boxes under the columns show the visual counting of the migrated cells. Panel C. TCTN2 over-expression increases the cell clonogenic phenotype. The graph reports the effect of the TCTN2 over-expression on the number of colonies formed by the HCT15 cell line on soft agar upon transfection with the TCTN2-encoding plasmid (3). Cells either untreated (1) or transfected with the empty plasmid pcDNA3 (2) were used as controls. Images of the cell colonies formed under each tested condition are reported below each histogram.
Figure 5:
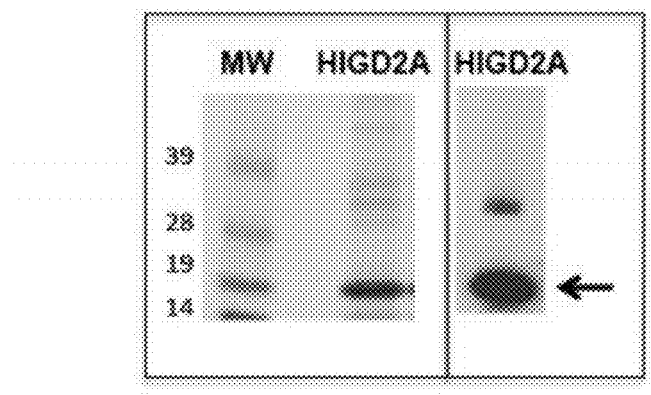
FIG. 5. Analysis of purified HIGD2A recombinant protein expressed in *E. coli*. Left panel: Comassie staining of purified His-tag HIGD2A fusion protein expressed in *E. coli* separated by SDS-PAGE; Right panel: WB on the purified recombinant HIGD2A protein stained with anti-HIGD2A antibody. Arrow marks the protein band of the expected size. Molecular weight markers are reported on the left.
Figure 6:
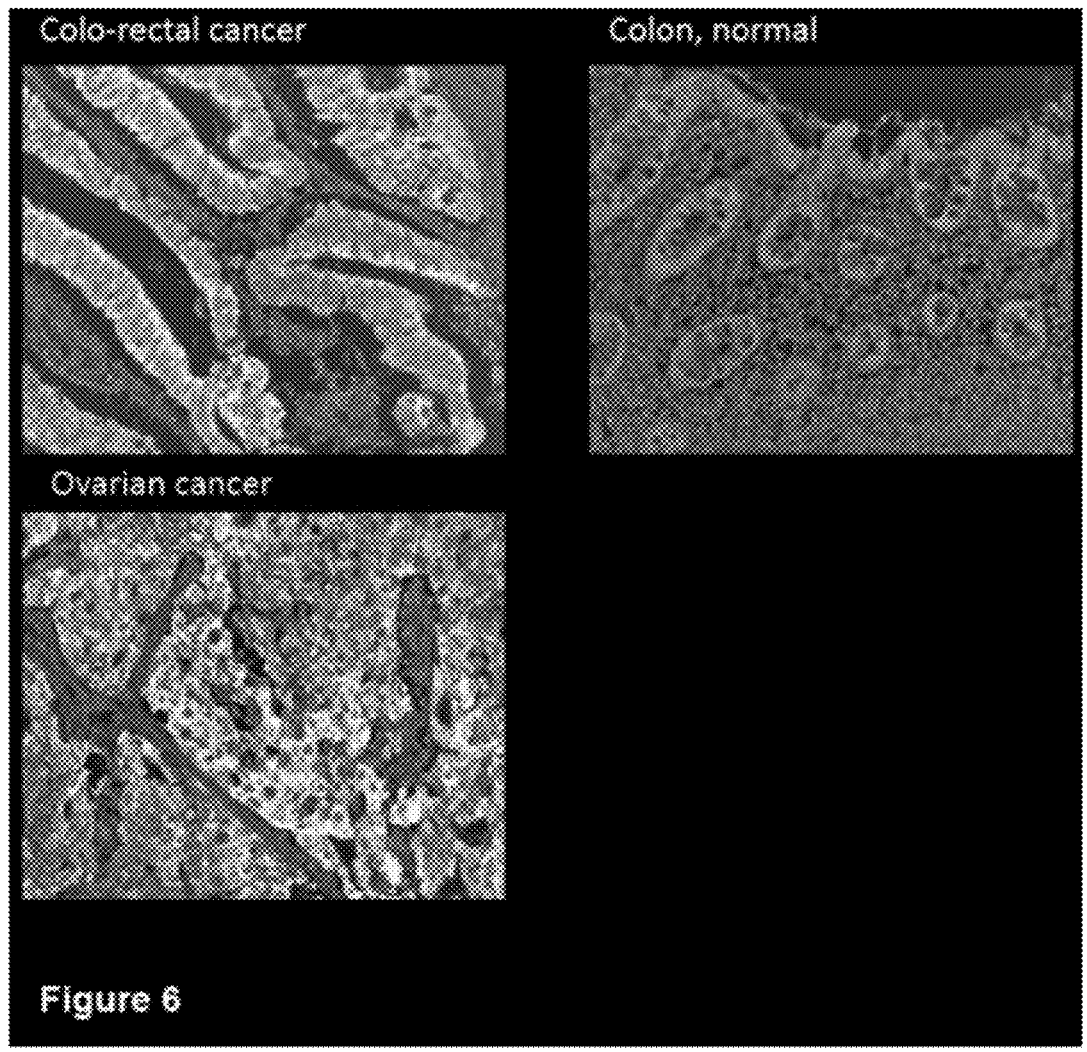
FIG. 6. Examples of immuno-histochemistry analysis of tumor (left panels) and normal tissue samples (right panels) stained with anti-HID2A antibodies. In the case of the ovarian cancer, the normal tissue surrounds the tumor. The antibody-stains specifically tumor cells (in dark grey); negative or poor staining is visible in normal cells.

Examples of the phenotypic changes induced by reducing the marker expression with specific siRNA are shown for FAM62A, TCTN1 and TCTN3. Inhibition of either TCTN1 or TCTN3 expression reduces the capability of the HCT15 tumor cell line to grow on soft agar, as shown by the lower number and size of colonies formed by cells treated with TCTN1- and TCTN3-siRNAs (FIG. 4A). Inhibition of TCTN1 and TCTN3 also impairs the invasive phenotype of the HCT15 cell line (FIG. 4B). Similarly, inhibition of FAM62A expression significantly impairs the invasive phenotype of the MCF7 and MDA-MB231 tumor cell lines (FIG. 20).

Examples of the phenotypic changes induced by an increased marker expression in cell transfected with the marker-encoding plasmids are reported for TCTN2. TCTN2 over-expression increases the capability of the HCT15 cell line to proliferate on soft agar, as shown by the higher number of colonies formed by TCTN2-transfected cells (FIG. 4C). Altogether, the results indicate that the proteins are involved in tumorigenesis and/or tumor progression.

REFERENCES

1. Adams G. P. and Weiner L. M. (2005) Monoclonal antibody therapy cancer. Nat Biotechnol. 23:1147-57;
2. Anderson, L., and Seilhamer, J. (1997). A comparison of selected mRNA and protein abundances in human liver. Electrophoresis 18, 533-537;
3. Chen, G., Gharib, T. G., Wang, H., Huang, C. C., Kuick, R., Thomas, D. G., Shedden, K. A., Misek, D. E., Taylor, J. M., Giordano, T. J., Kardia, S. L., Iannettoni, M. D., Yee, J., Hogg, P. J., Orringer, M. B., Hanash, S. M., and Beer, D. G. (2003) Protein profiles associated with survival in lung adenocarcinoma. Proc. Natl. Acad. Sci. U.S.A 100, 13537-13542;
4. Ginestier, C., Charafe-Jauffret, E., Bertucci, F., Eisinger, F., Geneix, J., Bechlian, D., Conte, N., Adelaide, J., Toiron, Y., Nguyen, C., Viens, P., Mozziconacci, M. J., Houlgatte, R., Birnbaum, D., and Jacquemier, J. (2002) Distinct and complementary information provided by use of tissue and DNA microarrays in the study of breast tumor markers. Am. J. Pathol. 161, 1223-1233;
5. Gygi, S. P., Rochon, Y., Franza, B. R., and Aebersold, R. (1999) Correlation between protein and mRNA abundance in yeast. Mol. Cell. Biol. 19, 1720-1730; Nishizuka, S., Charboneau, L., Young, L., Major, S., Reinhold, W. C., Waltham, M., Kouros-Mehr, H., Bussey, K. J., Lee, J. K., Espina, V., Munson, P. J., Petricoin, E., III, Liotta, L. A., and Weinstein, J. N. (2003) Proteomic profiling of the NCI-60 cancer cell lines using new high-density reverse-phase lysate microarrays. Proc. Natl. Acad. Sci. U.S.A 100, 14229-14234;
6. Tyers, M., and Mann, M. (2003) From genomics to proteomics. Nature 422, 193-197;
7. Kononen J et al (1998) Nature Med. 4:844-847;
8. Kallioniemi O P et al (2001) Hum. Mol. Genet. 10:657-662.

The invention claimed is:

1. A method of treating a patient having an ovary, colon, colorectal or lung malignancy comprising:
   screening an ovary, colon, colorectal or lung tissue sample of said patient for said malignancy with a polyclonal antibody to fragment 171-444 of TCTN2 SEQ ID NO: 9,
   determining with immunoradiometric, immunoenzymatic or immunohistochemical techniques the presence in said tissue sample of the tumor marker
   Tectonic-2 (TCTN2) protein, SEQ ID NO:9 or an isoform thereof having sequence identity of at least 90% to SEQ ID NO:9;
   wherein said tumor marker is expressed on tumor tissues but not on normal tissues; and
   treating said patient if said polyclonal antibody detects the presence of the tumor marker in said tissue sample.

2. A method according to claim 1, wherein the tissue sample is a sample of colon or colo-rectal tissue, said method comprising determining the presence in said sample of the tumor marker TCTN2.

3. A method according to claim 1, wherein the tissue sample is a sample of ovary tissue, said method comprising determining the presence in said sample of the tumor marker TCTN2.

4. An in vitro method for determining the presence of a tumor in a subject and treating said subject, the method comprising:
   (1) obtaining a sample of an ovary, colon, colorectal or lung tissue sample from said subject;
   (2) incubating said tissue sample with a polyclonal antibody to fragment 171-444 of TCTN2 SEQ ID NO:9 capable of binding
   Tectonic-2 (TCTN2) protein, SEQ ID NO:9 or an isoform thereof having sequence identity of at least 90% to SEQ ID NO:9;
   3) detecting whether a binding between said polyclonal antibody and the tumor marker protein occurs in said tissue sample using immunoradiometric, immunoenzymatic or immunohistochemical techniques, wherein said tumor marker protein is expressed on tumor tissues but not on normal tissues; and
   treating the subject.

5. A method according to claim 1, wherein
said isoform of said TCTN2 protein has a sequence identity of at least 95% to SEQ ID NO:9.

6. The method of claim 4, wherein
said isoform of said TCTN2 protein has a sequence identity of at least 95% to SEQ ID NO:9.

* * * * *

SEQUENCE LISTING

```
<160> NUMBER OF SEQ ID NOS: 55

<210> SEQ ID NO 1
<211> LENGTH: 260
<212> TYPE: PRT
<213> ORGANISM: Homo sapiens

<400> SEQUENCE: 1

Met Lys Thr Ser Asp Gly Phe Thr Leu Asn Ala Glu Ser Tyr Val Ser
1               5                   10                  15

Phe Thr Thr Lys Leu Asp Ile Pro Thr Ala Ala Lys Tyr Glu Tyr Gly
            20                  25                  30

Val Pro Leu Gln Thr Ser Asp Ser Phe Leu Arg Phe Pro Ser Ser Leu
        35                  40                  45

Thr Ser Ser Leu Cys Thr Asp Asn Asn Pro Ala Ala Phe Leu Val Asn
    50                  55                  60
```

Gln Ala Val Lys Cys Thr Arg Lys Ile Asn Leu Glu Gln Cys Glu Glu
 65                  70                  75                  80

Ile Glu Ala Leu Ser Met Ala Phe Tyr Ser Ser Pro Glu Ile Leu Arg
                 85                  90                  95

Val Pro Asp Ser Arg Lys Lys Val Pro Ile Thr Val Gln Ser Ile Val
            100                 105                 110

Ile Gln Ser Leu Asn Lys Thr Leu Thr Arg Arg Glu Asp Thr Asp Val
        115                 120                 125

Leu Gln Pro Thr Leu Val Asn Ala Gly His Phe Ser Leu Cys Val Asn
    130                 135                 140

Val Val Leu Glu Val Lys Tyr Ser Leu Thr Tyr Thr Asp Ala Gly Glu
145                 150                 155                 160

Val Thr Lys Ala Asp Leu Ser Phe Val Leu Gly Thr Val Ser Ser Val
                165                 170                 175

Val Val Pro Leu Gln Gln Lys Phe Glu Ile His Phe Leu Gln Thr Asp
            180                 185                 190

Trp Ser Ser Pro Val Ser Ala Arg Ser Thr Glu Gly Glu Glu Pro Ala
        195                 200                 205

Val Gly Pro Gly Leu Pro Arg Leu Arg Gly Pro Phe Trp Lys Phe Pro
210                 215                 220

Gly Pro Gly His Ala Gly Leu Gly Ala His Pro Leu His His Pro Val
225                 230                 235                 240

Ile Gln Gln Glu Gly Phe Leu Pro Ala Pro Arg Gly Phe Gly Tyr Arg
                245                 250                 255

Ser Glu Val Asp
            260

<210> SEQ ID NO 2
<211> LENGTH: 483
<212> TYPE: PRT
<213> ORGANISM: Homo sapiens

<400> SEQUENCE: 2

Met Ile Thr Ala His Cys Ser Leu Asp Leu Leu Gly Ser Val Ala Val
1               5                   10                  15

Leu Cys Val Cys Asp Leu Ser Pro Ala Gln Cys Asp Ile Asn Cys Cys
                20                  25                  30

Cys Asp Pro Asp Cys Ser Ser Val Asp Phe Ser Val Phe Ser Ala Cys
            35                  40                  45

Ser Val Pro Val Val Thr Gly Asp Ser Gln Phe Cys Ser Gln Lys Ala
        50                  55                  60

Val Ile Tyr Ser Leu Asn Phe Thr Ala Asn Pro Pro Gln Arg Val Phe
65                  70                  75                  80

Glu Leu Val Asp Gln Ile Asn Pro Ser Ile Phe Cys Ile His Ile Thr
                85                  90                  95

Asn Tyr Lys Pro Ala Leu Ser Phe Ile Asn Pro Glu Val Pro Asp Glu
            100                 105                 110

Asn Asn Phe Asp Thr Leu Met Lys Thr Ser Asp Gly Phe Thr Leu Asn
        115                 120                 125

Ala Glu Ser Tyr Val Ser Phe Thr Thr Lys Leu Asp Ile Pro Thr Ala
    130                 135                 140

Ala Lys Tyr Glu Tyr Gly Val Pro Leu Gln Thr Ser Asp Ser Phe Leu
145                 150                 155                 160

Arg Phe Pro Ser Ser Leu Thr Ser Ser Leu Cys Thr Asp Asn Asn Pro
                165                 170                 175

```
Ala Ala Phe Leu Val Asn Gln Ala Val Lys Cys Thr Arg Lys Ile Asn
            180                 185                 190
Leu Glu Gln Cys Glu Glu Ile Glu Ala Leu Ser Met Ala Phe Tyr Ser
        195                 200                 205
Ser Pro Glu Ile Leu Arg Val Pro Asp Ser Arg Lys Lys Val Pro Ile
210                 215                 220
Thr Val Gln Ser Ile Val Ile Gln Ser Leu Asn Lys Thr Leu Thr Arg
225                 230                 235                 240
Arg Glu Asp Thr Asp Val Leu Gln Pro Thr Leu Val Asn Ala Gly His
            245                 250                 255
Phe Ser Leu Cys Val Asn Val Val Leu Glu Val Lys Tyr Ser Leu Thr
        260                 265                 270
Tyr Thr Asp Ala Gly Glu Val Thr Lys Ala Asp Leu Ser Phe Val Leu
    275                 280                 285
Gly Thr Val Ser Ser Val Val Pro Leu Gln Gln Lys Phe Glu Ile
290                 295                 300
His Phe Leu Gln Glu Asn Thr Gln Pro Val Pro Leu Ser Gly Asn Pro
305                 310                 315                 320
Gly Tyr Val Val Gly Leu Pro Leu Ala Ala Gly Phe Gln Pro His Lys
            325                 330                 335
Thr Gly Ala Leu Pro Cys Gln Leu Val Ala Gln Lys Val Lys Ser Leu
        340                 345                 350
Leu Trp Gly Gln Gly Phe Pro Asp Tyr Val Ala Pro Phe Gly Asn Ser
    355                 360                 365
Gln Ala Gln Asp Met Leu Asp Trp Val Pro Ile His Phe Ile Thr Gln
370                 375                 380
Ser Phe Asn Arg Lys His Phe Val Leu Gln Asp Ser Cys Gln Leu Pro
385                 390                 395                 400
Gly Ala Leu Val Ile Glu Val Lys Trp Thr Lys Tyr Gly Ser Leu Leu
            405                 410                 415
Asn Pro Gln Ala Lys Ile Val Asn Val Thr Ala Asn Leu Ile Ser Ser
        420                 425                 430
Ser Phe Pro Glu Ala Asn Ser Gly Asn Glu Arg Thr Ile Leu Ile Ser
    435                 440                 445
Thr Ala Val Thr Phe Val Asp Val Ser Ala Pro Ala Glu Ala Gly Phe
450                 455                 460
Arg Ala Pro Pro Ala Ile Asn Ala Arg Leu Pro Phe Asn Phe Phe Phe
465                 470                 475                 480
Pro Phe Val

<210> SEQ ID NO 3
<211> LENGTH: 531
<212> TYPE: PRT
<213> ORGANISM: Homo sapiens

<400> SEQUENCE: 3

Met Cys Gln Leu Leu Glu Ser Thr Val Ile Gln Pro Gln Gly Asp Ser
1               5                   10                  15
Pro Val Ala Val Leu Cys Val Cys Asp Leu Ser Pro Ala Gln Cys Asp
            20                  25                  30
Ile Asn Cys Cys Cys Asp Pro Asp Cys Ser Ser Val Asp Phe Ser Val
        35                  40                  45
Phe Ser Ala Cys Ser Val Pro Val Val Thr Gly Asp Ser Gln Phe Cys
    50                  55                  60
```

```
Ser Gln Lys Ala Val Ile Tyr Ser Leu Asn Phe Thr Ala Asn Pro Pro
 65                  70                  75                  80

Gln Arg Val Phe Glu Leu Val Asp Gln Ile Asn Pro Ser Ile Phe Cys
                 85                  90                  95

Ile His Ile Thr Asn Tyr Lys Pro Ala Leu Ser Phe Ile Asn Pro Glu
            100                 105                 110

Val Pro Asp Glu Asn Asn Phe Asp Thr Leu Met Lys Thr Ser Asp Gly
        115                 120                 125

Phe Thr Leu Asn Ala Glu Ser Tyr Val Ser Phe Thr Thr Lys Leu Asp
    130                 135                 140

Ile Pro Thr Ala Ala Lys Tyr Glu Tyr Gly Val Pro Leu Gln Thr Ser
145                 150                 155                 160

Asp Ser Phe Leu Arg Phe Pro Ser Ser Leu Thr Ser Ser Leu Cys Thr
                165                 170                 175

Asp Asn Asn Pro Ala Ala Phe Leu Val Asn Gln Ala Val Lys Cys Thr
            180                 185                 190

Arg Lys Ile Asn Leu Glu Gln Cys Glu Glu Ile Glu Ala Leu Ser Met
        195                 200                 205

Ala Phe Tyr Ser Ser Pro Glu Ile Leu Arg Val Pro Asp Ser Arg Lys
    210                 215                 220

Lys Val Pro Ile Thr Val Gln Ser Ile Val Ile Gln Ser Leu Asn Lys
225                 230                 235                 240

Thr Leu Thr Arg Arg Glu Asp Thr Asp Val Leu Gln Pro Thr Leu Val
                245                 250                 255

Asn Ala Gly His Phe Ser Leu Cys Val Asn Val Val Leu Glu Val Lys
            260                 265                 270

Tyr Ser Leu Thr Tyr Thr Asp Ala Gly Glu Val Thr Lys Ala Asp Leu
        275                 280                 285

Ser Phe Val Leu Gly Thr Val Ser Ser Val Val Pro Leu Gln Gln
    290                 295                 300

Lys Phe Glu Ile His Phe Leu Gln Glu Asn Thr Gln Pro Val Pro Leu
305                 310                 315                 320

Ser Gly Asn Pro Gly Tyr Val Val Gly Leu Pro Leu Ala Ala Gly Phe
                325                 330                 335

Gln Pro His Lys Met Ser Gly Ile Ile Gln Thr Thr Asn Arg Tyr Gly
            340                 345                 350

Gln Leu Thr Ile Leu His Ser Thr Thr Glu Gln Asp Cys Leu Ala Leu
        355                 360                 365

Glu Gly Val Arg Thr Pro Val Leu Phe Gly Tyr Thr Met Gln Ser Gly
    370                 375                 380

Cys Lys Leu Arg Leu Thr Gly Ala Leu Pro Cys Gln Leu Val Ala Gln
385                 390                 395                 400

Lys Val Lys Ser Leu Leu Trp Gly Gln Gly Phe Pro Asp Tyr Val Ala
                405                 410                 415

Pro Phe Gly Asn Ser Gln Ala Gln Asp Met Leu Asp Trp Val Pro Ile
            420                 425                 430

His Phe Ile Thr Gln Ser Phe Asn Arg Lys Asp Ser Cys Gln Leu Pro
        435                 440                 445

Gly Ala Leu Val Ile Glu Val Lys Trp Thr Lys Tyr Gly Ser Leu Leu
    450                 455                 460

Asn Pro Gln Ala Lys Ile Val Asn Val Thr Ala Asn Leu Ile Ser Ser
465                 470                 475                 480
```

```
Ser Phe Pro Glu Ala Asn Ser Gly Asn Glu Arg Thr Ile Leu Ile Ser
                485                 490                 495

Thr Ala Val Thr Phe Val Asp Val Ser Ala Pro Ala Glu Ala Gly Phe
            500                 505                 510

Arg Ala Pro Pro Ala Ile Asn Ala Arg Leu Pro Phe Asn Phe Phe Phe
            515                 520                 525

Pro Phe Val
        530

<210> SEQ ID NO 4
<211> LENGTH: 592
<212> TYPE: PRT
<213> ORGANISM: Homo sapiens

<400> SEQUENCE: 4

Met Arg Pro Arg Gly Leu Pro Pro Leu Leu Val Val Leu Leu Gly Cys
1               5                   10                  15

Trp Ala Ser Val Ser Ala Gln Thr Asp Ala Thr Pro Ala Val Thr Thr
            20                  25                  30

Glu Gly Leu Asn Ser Thr Glu Ala Ala Leu Ala Thr Phe Gly Thr Phe
        35                  40                  45

Pro Ser Thr Arg Pro Pro Gly Thr Pro Arg Ala Pro Gly Pro Ser Ser
50                  55                  60

Gly Pro Arg Pro Thr Pro Val Thr Asp Val Ala Val Leu Cys Val Cys
65                  70                  75                  80

Asp Leu Ser Pro Ala Gln Cys Asp Ile Asn Cys Cys Cys Asp Pro Asp
                85                  90                  95

Cys Ser Ser Val Asp Phe Ser Val Phe Ser Ala Cys Ser Val Pro Val
            100                 105                 110

Val Thr Gly Asp Ser Gln Phe Cys Ser Gln Lys Ala Val Ile Tyr Ser
            115                 120                 125

Leu Asn Phe Thr Ala Asn Pro Pro Gln Arg Val Phe Glu Leu Val Asp
        130                 135                 140

Gln Ile Asn Pro Ser Ile Phe Cys Ile His Ile Thr Asn Tyr Lys Pro
145                 150                 155                 160

Ala Leu Ser Phe Ile Asn Pro Glu Val Pro Asp Glu Asn Asn Phe Asp
                165                 170                 175

Thr Leu Met Lys Thr Ser Asp Gly Phe Thr Leu Asn Ala Glu Ser Tyr
            180                 185                 190

Val Ser Phe Thr Thr Lys Leu Asp Ile Pro Thr Ala Ala Lys Tyr Glu
        195                 200                 205

Tyr Gly Val Pro Leu Gln Thr Ser Asp Ser Phe Leu Arg Phe Pro Ser
    210                 215                 220

Ser Leu Thr Ser Ser Leu Cys Thr Asp Asn Asn Pro Ala Ala Phe Leu
225                 230                 235                 240

Val Asn Gln Ala Val Lys Cys Thr Arg Lys Ile Asn Leu Glu Gln Cys
                245                 250                 255

Glu Glu Ile Glu Ala Leu Ser Met Ala Phe Tyr Ser Ser Pro Glu Ile
            260                 265                 270

Leu Arg Val Pro Asp Ser Arg Lys Lys Val Pro Ile Thr Val Gln Ser
        275                 280                 285

Ile Val Ile Gln Ser Leu Asn Lys Thr Leu Thr Arg Arg Glu Asp Thr
    290                 295                 300

Asp Val Leu Gln Pro Thr Leu Val Asn Ala Gly His Phe Ser Leu Cys
305                 310                 315                 320
```

```
Val Asn Val Val Leu Glu Val Lys Tyr Ser Leu Thr Tyr Thr Asp Ala
                325                 330                 335

Gly Glu Val Thr Lys Ala Asp Leu Ser Phe Val Leu Gly Thr Val Ser
            340                 345                 350

Ser Val Val Pro Leu Gln Gln Lys Phe Glu Ile His Phe Leu Gln
            355                 360                 365

Glu Asn Thr Gln Pro Val Pro Leu Ser Gly Asn Pro Gly Tyr Val Val
        370                 375                 380

Gly Leu Pro Leu Ala Ala Gly Phe Gln Pro His Lys Gly Ser Gly Ile
385                 390                 395                 400

Ile Gln Thr Thr Asn Arg Tyr Gly Gln Leu Thr Ile Leu His Ser Thr
                405                 410                 415

Thr Glu Gln Asp Cys Leu Ala Leu Glu Gly Val Arg Thr Pro Val Leu
            420                 425                 430

Phe Gly Tyr Thr Met Gln Ser Gly Cys Lys Leu Arg Leu Thr Gly Ala
            435                 440                 445

Leu Pro Cys Gln Leu Val Ala Gln Lys Val Lys Ser Leu Leu Trp Gly
        450                 455                 460

Gln Gly Phe Pro Asp Tyr Val Ala Pro Phe Gly Asn Ser Gln Ala Gln
465                 470                 475                 480

Asp Met Leu Asp Trp Val Pro Ile His Phe Ile Thr Gln Ser Phe Asn
                485                 490                 495

Arg Lys His Phe Val Leu Gln Asp Ser Cys Gln Leu Pro Gly Ala Leu
            500                 505                 510

Val Ile Glu Val Lys Trp Thr Lys Tyr Gly Ser Leu Leu Asn Pro Gln
            515                 520                 525

Ala Lys Ile Val Asn Val Thr Ala Asn Leu Ile Ser Ser Ser Phe Pro
        530                 535                 540

Glu Ala Asn Ser Gly Asn Glu Arg Thr Ile Leu Ile Ser Thr Ala Val
545                 550                 555                 560

Thr Phe Val Asp Val Ser Ala Pro Ala Glu Ala Gly Phe Arg Ala Pro
                565                 570                 575

Pro Ala Ile Asn Ala Arg Leu Pro Phe Asn Phe Phe Pro Phe Val
            580                 585                 590

<210> SEQ ID NO 5
<211> LENGTH: 573
<212> TYPE: PRT
<213> ORGANISM: Homo sapiens

<400> SEQUENCE: 5

Met Arg Pro Arg Gly Leu Pro Pro Leu Leu Val Val Leu Leu Gly Cys
1               5                   10                  15

Trp Ala Ser Val Ser Ala Gln Thr Asp Ala Thr Pro Ala Val Thr Thr
            20                  25                  30

Glu Gly Leu Asn Ser Thr Glu Ala Ala Leu Ala Thr Phe Gly Thr Phe
        35                  40                  45

Pro Ser Thr Arg Pro Pro Gly Thr Pro Arg Ala Pro Gly Pro Ser Ser
    50                  55                  60

Gly Pro Arg Pro Thr Pro Val Thr Asp Val Ala Val Leu Cys Val Cys
65                  70                  75                  80

Asp Leu Ser Pro Ala Gln Cys Asp Ile Asn Cys Cys Cys Asp Pro Asp
                85                  90                  95

Cys Ser Ser Val Asp Phe Ser Val Phe Ser Ala Cys Ser Val Pro Val
```

-continued

```
                100                 105                 110
Val Thr Gly Asp Ser Gln Phe Cys Ser Gln Lys Ala Val Ile Tyr Ser
            115                 120                 125

Leu Asn Phe Thr Ala Asn Pro Pro Gln Arg Val Phe Glu Leu Val Asp
            130                 135                 140

Gln Ile Asn Pro Ser Ile Phe Cys Ile His Ile Thr Asn Tyr Lys Pro
145                 150                 155                 160

Ala Leu Ser Phe Ile Asn Pro Glu Val Pro Asp Glu Asn Asn Phe Asp
            165                 170                 175

Thr Leu Met Lys Thr Ser Asp Gly Phe Thr Leu Asn Ala Glu Ser Tyr
            180                 185                 190

Val Ser Phe Thr Thr Lys Leu Asp Ile Pro Thr Ala Ala Lys Tyr Glu
            195                 200                 205

Tyr Gly Val Pro Leu Gln Thr Ser Asp Ser Phe Leu Arg Phe Pro Ser
            210                 215                 220

Ser Leu Thr Ser Ser Leu Cys Thr Asp Asn Asn Pro Ala Gly Gln Ala
225                 230                 235                 240

Tyr Trp Phe Thr Pro Val Ile Pro Ala Leu Trp Glu Ala Glu Ala Arg
            245                 250                 255

Gly Ser Leu Glu Val Pro Asp Ser Arg Lys Lys Val Pro Ile Thr Val
            260                 265                 270

Gln Ser Ile Val Ile Gln Ser Leu Asn Lys Thr Leu Thr Arg Arg Glu
            275                 280                 285

Asp Thr Asp Val Leu Gln Pro Thr Leu Val Asn Ala Gly His Phe Ser
            290                 295                 300

Leu Cys Val Asn Val Val Leu Glu Val Lys Tyr Ser Leu Thr Tyr Thr
305                 310                 315                 320

Asp Ala Gly Glu Val Thr Lys Ala Asp Leu Ser Phe Val Leu Gly Thr
            325                 330                 335

Val Ser Ser Val Val Pro Leu Gln Gln Lys Phe Glu Ile His Phe
            340                 345                 350

Leu Gln Glu Asn Thr Gln Pro Val Pro Leu Ser Gly Asn Pro Gly Tyr
            355                 360                 365

Val Val Gly Leu Pro Leu Ala Ala Gly Phe Gln Pro His Lys Gly Ser
            370                 375                 380

Gly Ile Ile Gln Thr Thr Asn Arg Tyr Gly Gln Leu Thr Ile Leu His
385                 390                 395                 400

Ser Thr Thr Glu Gln Asp Cys Leu Ala Leu Glu Gly Val Arg Thr Pro
            405                 410                 415

Val Leu Phe Gly Tyr Thr Met Gln Ser Gly Cys Lys Leu Arg Leu Thr
            420                 425                 430

Gly Ala Leu Pro Cys Gln Leu Val Ala Gln Lys Val Lys Ser Leu Leu
            435                 440                 445

Trp Gly Gln Gly Phe Pro Asp Tyr Val Ala Pro Phe Gly Asn Ser Gln
            450                 455                 460

Ala Gln Asp Met Leu Asp Trp Val Pro Ile His Phe Ile Thr Gln Ser
465                 470                 475                 480

Phe Asn Arg Lys Asp Ser Cys Gln Leu Pro Gly Ala Leu Val Ile Glu
            485                 490                 495

Val Lys Trp Thr Lys Tyr Gly Ser Leu Leu Asn Pro Gln Ala Lys Ile
            500                 505                 510

Val Asn Val Thr Ala Asn Leu Ile Ser Ser Ser Phe Pro Glu Ala Asn
            515                 520                 525
```

Ser Gly Asn Glu Arg Thr Ile Leu Ile Ser Thr Ala Val Thr Phe Val
            530                 535                 540

Asp Val Ser Ala Pro Ala Glu Ala Gly Phe Arg Ala Pro Pro Ala Ile
545                 550                 555                 560

Asn Ala Arg Leu Pro Phe Asn Phe Phe Phe Pro Phe Val
                565                 570

<210> SEQ ID NO 6
<211> LENGTH: 587
<212> TYPE: PRT
<213> ORGANISM: Homo sapiens

<400> SEQUENCE: 6

Met Arg Pro Arg Gly Leu Pro Pro Leu Leu Val Val Leu Leu Gly Cys
1               5                   10                  15

Trp Ala Ser Val Ser Ala Gln Thr Asp Ala Thr Pro Ala Val Thr Thr
                20                  25                  30

Glu Gly Leu Asn Ser Thr Glu Ala Ala Leu Ala Thr Phe Gly Thr Phe
            35                  40                  45

Pro Ser Thr Arg Pro Pro Gly Thr Pro Arg Ala Pro Gly Pro Ser Ser
50                  55                  60

Gly Pro Arg Pro Thr Pro Val Thr Asp Val Ala Val Leu Cys Val Cys
65                  70                  75                  80

Asp Leu Ser Pro Ala Gln Cys Asp Ile Asn Cys Cys Cys Asp Pro Asp
                85                  90                  95

Cys Ser Ser Val Asp Phe Ser Val Phe Ser Ala Cys Ser Val Pro Val
            100                 105                 110

Val Thr Gly Asp Ser Gln Phe Cys Ser Gln Lys Ala Val Ile Tyr Ser
            115                 120                 125

Leu Asn Phe Thr Ala Asn Pro Pro Gln Arg Val Phe Glu Leu Val Asp
130                 135                 140

Gln Ile Asn Pro Ser Ile Phe Cys Ile His Ile Thr Asn Tyr Lys Pro
145                 150                 155                 160

Ala Leu Ser Phe Ile Asn Pro Glu Val Pro Asp Glu Asn Asn Phe Asp
                165                 170                 175

Thr Leu Met Lys Thr Ser Asp Gly Phe Thr Leu Asn Ala Glu Ser Tyr
            180                 185                 190

Val Ser Phe Thr Thr Lys Leu Asp Ile Pro Thr Ala Ala Lys Tyr Glu
            195                 200                 205

Tyr Gly Val Pro Leu Gln Thr Ser Asp Ser Phe Leu Arg Phe Pro Ser
210                 215                 220

Ser Leu Thr Ser Ser Leu Cys Thr Asp Asn Asn Pro Ala Ala Phe Leu
225                 230                 235                 240

Val Asn Gln Ala Val Lys Cys Thr Arg Lys Ile Asn Leu Glu Gln Cys
                245                 250                 255

Glu Glu Ile Glu Ala Leu Ser Met Ala Phe Tyr Ser Ser Pro Glu Ile
            260                 265                 270

Leu Arg Val Pro Asp Ser Arg Lys Lys Val Pro Ile Thr Val Gln Ser
            275                 280                 285

Ile Val Ile Gln Ser Leu Asn Lys Thr Leu Thr Arg Arg Glu Asp Thr
290                 295                 300

Asp Val Leu Gln Pro Thr Leu Val Asn Ala Gly His Phe Ser Leu Cys
305                 310                 315                 320

Val Asn Val Val Leu Glu Val Lys Tyr Ser Leu Thr Tyr Thr Asp Ala

```
            325                 330                 335
Gly Glu Val Thr Lys Ala Asp Leu Ser Phe Val Leu Gly Thr Val Ser
                340                 345                 350
Ser Val Val Pro Leu Gln Gln Lys Phe Glu Ile His Phe Leu Gln
            355                 360                 365
Glu Asn Thr Gln Pro Val Pro Leu Ser Gly Asn Pro Gly Tyr Val Val
        370                 375                 380
Gly Leu Pro Leu Ala Ala Gly Phe Gln Pro His Lys Gly Ser Gly Ile
385                 390                 395                 400
Ile Gln Thr Thr Asn Arg Tyr Gly Gln Leu Thr Ile Leu His Ser Thr
                405                 410                 415
Thr Glu Gln Asp Cys Leu Ala Leu Glu Gly Val Arg Thr Pro Val Leu
            420                 425                 430
Phe Gly Tyr Thr Met Gln Ser Gly Cys Lys Leu Arg Leu Thr Gly Ala
        435                 440                 445
Leu Pro Cys Gln Leu Val Ala Gln Lys Val Lys Ser Leu Leu Trp Gly
    450                 455                 460
Gln Gly Phe Pro Asp Tyr Val Ala Pro Phe Gly Asn Ser Gln Ala Gln
465                 470                 475                 480
Asp Met Leu Asp Trp Val Pro Ile His Phe Ile Thr Gln Ser Phe Asn
                485                 490                 495
Arg Lys Asp Ser Cys Gln Leu Pro Gly Ala Leu Val Ile Glu Val Lys
            500                 505                 510
Trp Thr Lys Tyr Gly Ser Leu Leu Asn Pro Gln Ala Lys Ile Val Asn
        515                 520                 525
Val Thr Ala Asn Leu Ile Ser Ser Ser Phe Pro Glu Ala Asn Ser Gly
    530                 535                 540
Asn Glu Arg Thr Ile Leu Ile Ser Thr Ala Val Thr Phe Val Asp Val
545                 550                 555                 560
Ser Ala Pro Ala Glu Ala Gly Phe Arg Ala Pro Pro Ala Ile Asn Ala
                565                 570                 575
Arg Leu Pro Phe Asn Phe Phe Phe Pro Phe Val
            580                 585

<210> SEQ ID NO 7
<211> LENGTH: 573
<212> TYPE: PRT
<213> ORGANISM: Homo sapiens

<400> SEQUENCE: 7

Met Arg Pro Arg Gly Leu Pro Pro Leu Leu Val Val Leu Leu Gly Cys
1               5                   10                  15
Trp Ala Ser Val Ser Ala Gln Thr Asp Ala Thr Pro Ala Val Thr Thr
                20                  25                  30
Glu Gly Leu Asn Ser Thr Glu Ala Ala Leu Ala Thr Phe Gly Thr Phe
            35                  40                  45
Pro Ser Thr Arg Pro Pro Gly Thr Pro Arg Ala Pro Gly Pro Ser Ser
        50                  55                  60
Gly Pro Arg Pro Thr Pro Val Thr Asp Val Ala Val Leu Cys Val Cys
65                  70                  75                  80
Asp Leu Ser Pro Ala Gln Cys Asp Ile Asn Cys Cys Asp Pro Asp Cys
                85                  90                  95
Cys Ser Ser Val Asp Phe Ser Val Phe Ser Ala Cys Ser Val Pro Val
            100                 105                 110
```

```
Val Thr Gly Asp Ser Gln Phe Cys Ser Gln Lys Ala Val Ile Tyr Ser
            115                 120                 125

Leu Asn Phe Thr Ala Asn Pro Pro Gln Arg Val Phe Glu Leu Val Asp
        130                 135                 140

Gln Ile Asn Pro Ser Ile Phe Cys Ile His Ile Thr Asn Tyr Lys Pro
145                 150                 155                 160

Ala Leu Ser Phe Ile Asn Pro Glu Val Pro Asp Glu Asn Asn Phe Asp
                165                 170                 175

Thr Leu Met Lys Thr Ser Asp Gly Phe Thr Leu Asn Ala Glu Ser Tyr
            180                 185                 190

Val Ser Phe Thr Thr Lys Leu Asp Ile Pro Thr Ala Ala Lys Tyr Glu
        195                 200                 205

Tyr Gly Val Pro Leu Gln Thr Ser Asp Ser Phe Leu Arg Phe Pro Ser
210                 215                 220

Ser Leu Thr Ser Ser Leu Cys Thr Asp Asn Asn Pro Ala Gly Gln Ala
225                 230                 235                 240

Tyr Trp Phe Thr Pro Val Ile Pro Ala Leu Trp Glu Ala Glu Ala Arg
                245                 250                 255

Gly Ser Leu Glu Val Pro Asp Ser Arg Lys Lys Val Pro Ile Thr Val
            260                 265                 270

Gln Ser Ile Val Ile Gln Ser Leu Asn Lys Thr Leu Thr Arg Arg Glu
        275                 280                 285

Asp Thr Asp Val Leu Gln Pro Thr Leu Val Asn Ala Gly His Phe Ser
        290                 295                 300

Leu Cys Val Asn Val Val Leu Glu Val Lys Tyr Ser Leu Thr Tyr Thr
305                 310                 315                 320

Asp Ala Gly Glu Val Thr Lys Ala Asp Leu Ser Phe Val Leu Gly Thr
                325                 330                 335

Val Ser Ser Val Val Pro Leu Gln Gln Lys Phe Glu Ile His Phe
            340                 345                 350

Leu Gln Glu Asn Thr Gln Pro Val Pro Leu Ser Gly Asn Pro Gly Tyr
        355                 360                 365

Val Val Gly Leu Pro Leu Ala Ala Gly Phe Gln Pro His Lys Met Ser
370                 375                 380

Gly Ile Ile Gln Thr Thr Asn Arg Tyr Gly Gln Leu Thr Ile Leu His
385                 390                 395                 400

Ser Thr Thr Glu Gln Asp Cys Leu Ala Leu Glu Gly Val Arg Thr Pro
                405                 410                 415

Val Leu Phe Gly Tyr Thr Met Gln Ser Gly Cys Lys Leu Arg Leu Thr
            420                 425                 430

Gly Ala Leu Pro Cys Gln Leu Val Ala Gln Lys Val Lys Ser Leu Leu
        435                 440                 445

Trp Gly Gln Gly Phe Pro Asp Tyr Val Ala Pro Phe Gly Asn Ser Gln
        450                 455                 460

Ala Gln Asp Met Leu Asp Trp Val Pro Ile His Phe Ile Thr Gln Ser
465                 470                 475                 480

Phe Asn Arg Lys Asp Ser Cys Gln Leu Pro Gly Ala Leu Val Ile Glu
                485                 490                 495

Val Lys Trp Thr Lys Tyr Gly Ser Leu Leu Asn Pro Gln Ala Lys Ile
            500                 505                 510

Val Asn Val Thr Ala Asn Leu Ile Ser Ser Ser Phe Pro Glu Ala Asn
        515                 520                 525

Ser Gly Asn Glu Arg Thr Ile Leu Ile Ser Thr Ala Val Thr Phe Val
```

```
            530                 535                 540
Asp Val Ser Ala Pro Ala Glu Ala Gly Phe Arg Ala Pro Pro Ala Ile
545                 550                 555                 560

Asn Ala Arg Leu Pro Phe Asn Phe Phe Pro Phe Val
                565                 570

<210> SEQ ID NO 8
<211> LENGTH: 592
<212> TYPE: PRT
<213> ORGANISM: Homo sapiens

<400> SEQUENCE: 8

Met Arg Pro Arg Gly Leu Pro Pro Leu Leu Val Val Leu Leu Gly Cys
1               5                   10                  15

Trp Ala Ser Val Ser Ala Gln Thr Asp Ala Thr Pro Ala Val Thr Thr
            20                  25                  30

Glu Gly Leu Asn Ser Thr Glu Ala Ala Leu Ala Thr Phe Gly Thr Phe
        35                  40                  45

Pro Ser Thr Arg Pro Pro Gly Thr Pro Arg Ala Pro Gly Pro Ser Ser
    50                  55                  60

Gly Pro Arg Pro Thr Pro Val Thr Asp Val Ala Val Leu Cys Val Cys
65                  70                  75                  80

Asp Leu Ser Pro Ala Gln Cys Asp Ile Asn Cys Cys Cys Asp Pro Asp
                85                  90                  95

Cys Ser Ser Val Asp Phe Ser Val Phe Ser Ala Cys Ser Val Pro Val
            100                 105                 110

Val Thr Gly Asp Ser Gln Phe Cys Ser Gln Lys Ala Val Ile Tyr Ser
        115                 120                 125

Leu Asn Phe Thr Ala Asn Pro Pro Gln Arg Val Phe Glu Leu Val Asp
    130                 135                 140

Gln Ile Asn Pro Ser Ile Phe Cys Ile His Thr Asn Tyr Lys Pro
145                 150                 155                 160

Ala Leu Ser Phe Ile Asn Pro Glu Val Pro Asp Glu Asn Asn Phe Asp
                165                 170                 175

Thr Leu Met Lys Thr Ser Asp Gly Phe Thr Leu Asn Ala Glu Ser Tyr
            180                 185                 190

Val Ser Phe Thr Thr Lys Leu Asp Ile Pro Thr Ala Ala Lys Tyr Glu
        195                 200                 205

Tyr Gly Val Pro Leu Gln Thr Ser Asp Ser Phe Leu Arg Phe Pro Ser
    210                 215                 220

Ser Leu Thr Ser Ser Leu Cys Thr Asp Asn Asn Pro Ala Ala Phe Leu
225                 230                 235                 240

Val Asn Gln Ala Val Lys Cys Thr Arg Lys Ile Asn Leu Glu Gln Cys
                245                 250                 255

Glu Glu Ile Glu Ala Leu Ser Met Ala Phe Tyr Ser Ser Pro Glu Ile
            260                 265                 270

Leu Arg Val Pro Asp Ser Arg Lys Val Pro Ile Thr Val Gln Ser
        275                 280                 285

Ile Val Ile Gln Ser Leu Asn Lys Thr Leu Thr Arg Arg Glu Asp Thr
    290                 295                 300

Asp Val Leu Gln Pro Thr Leu Val Asn Ala Gly His Phe Ser Leu Cys
305                 310                 315                 320

Val Asn Val Val Leu Glu Val Lys Tyr Ser Leu Thr Tyr Thr Asp Ala
                325                 330                 335
```

Gly Glu Val Thr Lys Ala Asp Leu Ser Phe Val Leu Gly Thr Val Ser
                340                 345                 350

Ser Val Val Pro Leu Gln Gln Lys Phe Glu Ile His Phe Leu Gln
            355                 360                 365

Glu Asn Thr Gln Pro Val Pro Leu Ser Gly Asn Pro Gly Tyr Val Val
        370                 375                 380

Gly Leu Pro Leu Ala Ala Gly Phe Gln Pro His Lys Met Ser Gly Ile
385                 390                 395                 400

Ile Gln Thr Thr Asn Arg Tyr Gly Gln Leu Thr Ile Leu His Ser Thr
            405                 410                 415

Thr Glu Gln Asp Cys Leu Ala Leu Glu Gly Val Arg Thr Pro Val Leu
        420                 425                 430

Phe Gly Tyr Thr Met Gln Ser Gly Cys Lys Leu Arg Leu Thr Gly Ala
            435                 440                 445

Leu Pro Cys Gln Leu Val Ala Gln Lys Val Lys Ser Leu Leu Trp Gly
        450                 455                 460

Gln Gly Phe Pro Asp Tyr Val Ala Pro Phe Gly Asn Ser Gln Ala Gln
465                 470                 475                 480

Asp Met Leu Asp Trp Val Pro Ile His Phe Ile Thr Gln Ser Phe Asn
            485                 490                 495

Arg Lys His Phe Val Leu Gln Asp Ser Cys Gln Leu Pro Gly Ala Leu
        500                 505                 510

Val Ile Glu Val Lys Trp Thr Lys Tyr Gly Ser Leu Leu Asn Pro Gln
            515                 520                 525

Ala Lys Ile Val Asn Val Thr Ala Asn Leu Ile Ser Ser Ser Phe Pro
530                 535                 540

Glu Ala Asn Ser Gly Asn Glu Arg Thr Ile Leu Ile Ser Thr Ala Val
545                 550                 555                 560

Thr Phe Val Asp Val Ser Ala Pro Ala Glu Ala Gly Phe Arg Ala Pro
            565                 570                 575

Pro Ala Ile Asn Ala Arg Leu Pro Phe Asn Phe Phe Pro Phe Val
        580                 585                 590

<210> SEQ ID NO 9
<211> LENGTH: 697
<212> TYPE: PRT
<213> ORGANISM: Homo sapiens

<400> SEQUENCE: 9

Met Gly Phe Gln Pro Pro Ala Ala Leu Leu Leu Arg Leu Phe Leu Leu
1               5                   10                  15

Gln Gly Ile Leu Arg Leu Leu Trp Gly Asp Leu Ala Phe Ile Pro Pro
            20                  25                  30

Phe Ile Arg Met Ser Gly Pro Ala Val Ser Ala Ser Leu Val Gly Asp
        35                  40                  45

Thr Glu Gly Val Thr Val Ser Leu Ala Val Leu Gln Asp Glu Ala Gly
    50                  55                  60

Ile Leu Pro Ile Pro Thr Cys Gly Val Leu Asn Asn Glu Thr Glu Asp
65                  70                  75                  80

Trp Ser Val Thr Val Ile Pro Gly Ala Lys Val Leu Glu Val Thr Val
            85                  90                  95

Arg Trp Lys Arg Gly Leu Asp Trp Cys Ser Ser Asn Glu Thr Asp Ser
        100                 105                 110

Phe Ser Glu Ser Pro Cys Ile Leu Gln Thr Leu Leu Val Ser Ala Ser
    115                 120                 125

```
His Asn Ser Ser Cys Ser Ala His Leu Leu Ile Gln Val Glu Ile Tyr
    130                 135                 140
Ala Asn Ser Ser Leu Thr His Asn Ala Ser Glu Asn Val Thr Val Ile
145                 150                 155                 160
Pro Asn Gln Val Tyr Gln Pro Leu Gly Pro Cys Pro Cys Asn Leu Thr
                165                 170                 175
Ala Gly Ala Cys Asp Val Arg Cys Cys Cys Asp Gln Glu Cys Ser Ser
            180                 185                 190
Asn Leu Thr Thr Leu Phe Arg Arg Ser Cys Phe Thr Gly Val Phe Gly
        195                 200                 205
Gly Asp Val Asn Pro Pro Phe Asp Gln Leu Cys Ser Ala Gly Thr Thr
    210                 215                 220
Thr Arg Gly Val Pro Asp Trp Phe Pro Phe Leu Cys Val Gln Ser Pro
225                 230                 235                 240
Leu Ala Asn Thr Pro Phe Leu Gly Tyr Phe Tyr His Gly Ala Val Ser
                245                 250                 255
Pro Lys Gln Asp Ser Ser Phe Glu Val Tyr Val Asp Thr Asp Ala Lys
            260                 265                 270
Asp Phe Ala Asp Phe Gly Tyr Lys Gln Gly Asp Pro Ile Met Thr Val
        275                 280                 285
Lys Lys Ala Tyr Phe Thr Ile Pro Gln Val Ser Leu Ala Gly Gln Cys
    290                 295                 300
Met Gln Asn Ala Pro Val Ala Phe Leu His Asn Phe Asp Val Lys Cys
305                 310                 315                 320
Val Thr Asn Leu Glu Leu Tyr Gln Glu Arg Asp Gly Ile Ile Asn Ala
                325                 330                 335
Lys Ile Lys Asn Val Ala Leu Gly Gly Ile Val Thr Pro Lys Val Ile
            340                 345                 350
Tyr Glu Glu Ala Thr Asp Leu Asp Lys Phe Ile Thr Asn Thr Glu Thr
        355                 360                 365
Pro Leu Asn Asn Gly Ser Thr Pro Arg Ile Val Asn Val Glu Glu His
    370                 375                 380
Tyr Ile Phe Lys Trp Asn Asn Asn Thr Ile Ser Glu Ile Asn Val Lys
385                 390                 395                 400
Ile Phe Arg Ala Glu Ile Asn Ala His Gln Lys Gly Ile Met Thr Gln
                405                 410                 415
Arg Phe Val Val Lys Phe Leu Ser Tyr Asn Ser Gly Asn Glu Glu Glu
            420                 425                 430
Leu Ser Gly Asn Pro Gly Tyr Gln Leu Gly Lys Pro Val Arg Ala Leu
        435                 440                 445
Asn Ile Asn Arg Met Asn Asn Val Thr Thr Leu His Leu Trp Gln Ser
    450                 455                 460
Ala Gly Arg Gly Leu Cys Thr Ser Ala Thr Phe Lys Pro Ile Leu Phe
465                 470                 475                 480
Gly Glu Asn Val Leu Ser Gly Cys Leu Leu Glu Val Gly Ile Asn Glu
                485                 490                 495
Asn Cys Thr Gln Leu Arg Glu Asn Ala Val Glu Arg Leu Asp Ser Leu
            500                 505                 510
Ile Gln Ala Thr His Val Ala Met Arg Gly Asn Ser Asp Tyr Ala Asp
        515                 520                 525
Leu Ser Asp Gly Trp Leu Glu Ile Ile Arg Val Asp Ala Pro Asp Pro
    530                 535                 540
```

```
Gly Ala Asp Pro Leu Ala Ser Ser Val Asn Gly Met Cys Leu Asp Ile
545                 550                 555                 560

Pro Ala His Leu Ser Ile Arg Ile Leu Ile Ser Asp Ala Gly Ala Val
                565                 570                 575

Glu Gly Ile Thr Gln Gln Glu Ile Leu Gly Val Glu Thr Arg Phe Ser
            580                 585                 590

Ser Val Asn Trp Gln Tyr Gln Cys Gly Leu Thr Cys Glu His Lys Ala
        595                 600                 605

Asp Leu Leu Pro Ile Ser Ala Ser Val Gln Phe Lys Ile Pro Ala
    610                 615                 620

Gln Leu Pro His Pro Leu Thr Arg Phe Gln Ile Asn Tyr Thr Glu Tyr
625                 630                 635                 640

Asp Cys Asn Arg Asn Glu Val Cys Trp Pro Gln Leu Leu Tyr Pro Trp
                645                 650                 655

Thr Gln Tyr Tyr Gln Gly Glu Leu His Ser Gln Cys Val Ala Lys Gly
            660                 665                 670

Leu Leu Leu Leu Leu Phe Leu Thr Leu Ala Leu Phe Leu Ser Asn Pro
        675                 680                 685

Trp Thr Arg Ile Cys Lys Ala Tyr Ser
    690                 695

<210> SEQ ID NO 10
<211> LENGTH: 625
<212> TYPE: PRT
<213> ORGANISM: Homo sapiens

<400> SEQUENCE: 10

Met Arg Leu Glu Thr Ala Glu Ala Tyr Val Gly Pro Gly Gly Pro Glu
1               5                   10                  15

Cys Pro Met Arg Thr Pro Gln Leu Ala Leu Leu Gln Val Phe Phe Leu
                20                  25                  30

Val Phe Pro Asp Gly Val Arg Pro Gln Pro Ser Ser Ser Pro Ser Gly
            35                  40                  45

Ala Val Pro Thr Ser Leu Glu Leu Gln Arg Gly Thr Asp Gly Gly Thr
        50                  55                  60

Leu Gln Ser Pro Ser Glu Ala Thr Ala Arg Pro Ala Val Pro Gly
65                  70                  75                  80

Leu Pro Thr Val Val Pro Thr Leu Val Thr Pro Ser Ala Pro Gly Asn
                85                  90                  95

Arg Thr Val Asp Leu Phe Pro Val Leu Pro Ile Cys Val Cys Asp Leu
            100                 105                 110

Thr Pro Gly Ala Cys Asp Ile Asn Cys Cys Cys Asp Arg Asp Cys Tyr
        115                 120                 125

Leu Leu His Pro Arg Thr Val Phe Ser Phe Cys Leu Pro Gly Ser Val
130                 135                 140

Arg Ser Ser Ser Trp Val Cys Val Asp Asn Ser Val Ile Phe Arg Ser
145                 150                 155                 160

Asn Ser Pro Phe Pro Ser Arg Val Phe Met Asp Ser Asn Gly Ile Arg
                165                 170                 175

Gln Phe Cys Val His Val Asn Asn Ser Asn Leu Asn Tyr Phe Gln Lys
            180                 185                 190

Leu Gln Lys Val Asn Ala Thr Asn Phe Gln Ala Leu Ala Ala Glu Phe
        195                 200                 205

Gly Gly Glu Ser Phe Thr Ser Thr Phe Gln Thr Gln Ser Pro Pro Ser
    210                 215                 220
```

```
Phe Tyr Arg Ala Gly Asp Pro Ile Leu Thr Tyr Phe Pro Lys Trp Ser
225                 230                 235                 240

Val Ile Ser Leu Leu Arg Gln Pro Ala Gly Val Gly Ala Gly Gly Leu
                245                 250                 255

Cys Ala Glu Ser Asn Pro Ala Gly Phe Leu Glu Ser Lys Ser Thr Thr
                260                 265                 270

Cys Thr Arg Phe Phe Lys Asn Leu Ala Ser Ser Cys Thr Leu Asp Ser
            275                 280                 285

Ala Leu Asn Ala Ala Ser Tyr Tyr Asn Phe Thr Val Leu Lys Val Pro
        290                 295                 300

Arg Ser Met Thr Asp Pro Gln Asn Met Glu Phe Gln Val Pro Val Ile
305                 310                 315                 320

Leu Thr Ser Gln Ala Asn Ala Pro Leu Leu Ala Gly Asn Thr Cys Gln
                325                 330                 335

Asn Val Val Ser Gln Val Thr Tyr Glu Ile Glu Thr Asn Gly Thr Phe
                340                 345                 350

Gly Ile Gln Lys Val Ser Val Ser Leu Gly Gln Thr Asn Leu Thr Val
            355                 360                 365

Glu Pro Gly Ala Ser Leu Gln Gln His Phe Ile Leu Arg Phe Arg Ala
370                 375                 380

Phe Gln Gln Ser Thr Ala Ala Ser Leu Thr Ser Pro Arg Ser Gly Asn
385                 390                 395                 400

Pro Gly Tyr Ile Val Gly Lys Pro Leu Leu Ala Leu Thr Asp Asp Ile
                405                 410                 415

Ser Tyr Ser Met Thr Leu Leu Gln Ser Gln Gly Asn Gly Ser Cys Ser
            420                 425                 430

Val Lys Arg His Glu Val Gln Phe Gly Val Asn Ala Ile Ser Gly Cys
        435                 440                 445

Lys Leu Arg Leu Lys Lys Ala Asp Cys Ser His Leu Gln Gln Glu Ile
        450                 455                 460

Tyr Gln Thr Leu His Gly Arg Pro Arg Pro Glu Tyr Val Ala Ile Phe
465                 470                 475                 480

Gly Asn Ala Asp Pro Ala Gln Lys Gly Gly Trp Thr Arg Ile Leu Asn
                485                 490                 495

Arg His Cys Ser Ile Ser Ala Ile Asn Cys Thr Ser Cys Cys Leu Ile
            500                 505                 510

Pro Val Ser Leu Glu Ile Gln Val Leu Trp Ala Tyr Val Gly Leu Leu
        515                 520                 525

Ser Asn Pro Gln Ala His Val Ser Gly Val Arg Phe Leu Tyr Gln Cys
530                 535                 540

Gln Ser Ile Gln Asp Ser Gln Val Thr Glu Val Ser Leu Thr Thr
545                 550                 555                 560

Leu Val Asn Phe Val Asp Ile Thr Gln Lys Pro Gln Pro Arg Gly
                565                 570                 575

Gln Pro Lys Met Asp Trp Lys Trp Pro Phe Asp Phe Pro Phe Lys
            580                 585                 590

Val Ala Phe Ser Arg Gly Val Phe Ser Gln Lys Cys Ser Val Ser Pro
            595                 600                 605

Ile Leu Ile Leu Cys Leu Leu Leu Gly Val Leu Asn Leu Glu Thr
            610                 615                 620

Met
625
```

<210> SEQ ID NO 11
<211> LENGTH: 429
<212> TYPE: PRT
<213> ORGANISM: Homo sapiens

<400> SEQUENCE: 11

```
Met Asp Ser Asn Gly Ile Arg Gln Phe Cys Val His Val Asn Asn Ser
1               5                   10                  15

Asn Leu Asn Tyr Phe Gln Lys Leu Gln Lys Val Asn Ala Thr Asn Phe
            20                  25                  30

Gln Ala Leu Ala Ala Glu Phe Gly Gly Glu Ser Phe Thr Ser Thr Phe
        35                  40                  45

Gln Thr Gln Ser Pro Pro Ser Phe Tyr Arg Ala Gly Asp Pro Ile Leu
    50                  55                  60

Thr Tyr Phe Pro Lys Trp Ser Val Ile Ser Leu Leu Arg Gln Pro Ala
65                  70                  75                  80

Gly Val Gly Ala Gly Gly Leu Cys Ala Glu Ser Asn Pro Ala Gly Phe
                85                  90                  95

Leu Glu Ser Lys Ser Thr Thr Cys Thr Arg Phe Phe Lys Asn Leu Ala
            100                 105                 110

Ser Ser Cys Thr Leu Asp Ser Ala Leu Asn Ala Ala Ser Tyr Tyr Asn
        115                 120                 125

Phe Thr Val Leu Lys Val Pro Arg Ser Met Thr Asp Pro Gln Asn Met
    130                 135                 140

Glu Val Thr Tyr Glu Ile Glu Thr Asn Gly Thr Phe Gly Ile Gln Lys
145                 150                 155                 160

Val Ser Val Ser Leu Gly Gln Thr Asn Leu Thr Val Glu Pro Gly Ala
                165                 170                 175

Ser Leu Gln Gln His Phe Ile Leu Arg Phe Arg Ala Phe Gln Gln Ser
            180                 185                 190

Thr Ala Ala Ser Leu Thr Ser Pro Arg Ser Gly Asn Pro Gly Tyr Ile
        195                 200                 205

Val Gly Lys Pro Leu Leu Ala Leu Thr Asp Asp Ile Ser Tyr Ser Met
    210                 215                 220

Thr Leu Leu Gln Ser Gln Gly Asn Gly Ser Cys Ser Val Lys Arg His
225                 230                 235                 240

Glu Val Gln Phe Gly Val Asn Ala Ile Ser Gly Cys Lys Leu Arg Leu
                245                 250                 255

Lys Lys Ala Asp Cys Ser His Leu Gln Gln Glu Ile Tyr Gln Thr Leu
            260                 265                 270

His Gly Arg Pro Arg Pro Glu Tyr Val Ala Ile Phe Gly Asn Ala Asp
        275                 280                 285

Pro Ala Gln Lys Gly Gly Trp Thr Arg Ile Leu Asn Arg His Cys Ser
    290                 295                 300

Ile Ser Ala Ile Asn Cys Thr Ser Cys Cys Leu Ile Pro Val Ser Leu
305                 310                 315                 320

Glu Ile Gln Val Leu Trp Ala Tyr Val Gly Leu Leu Ser Asn Pro Gln
                325                 330                 335

Ala His Val Ser Gly Val Arg Phe Leu Tyr Gln Cys Gln Ser Ile Gln
            340                 345                 350

Asp Ser Gln Gln Val Thr Glu Val Ser Leu Thr Thr Leu Val Asn Phe
        355                 360                 365

Val Asp Ile Thr Gln Lys Pro Gln Pro Arg Gly Gln Pro Lys Met
    370                 375                 380
```

```
Asp Trp Lys Trp Pro Phe Asp Phe Pro Phe Lys Val Ala Phe Ser
385                 390                 395                 400

Arg Gly Val Phe Ser Gln Lys Cys Ser Val Ser Pro Ile Leu Ile Leu
                405                 410                 415

Cys Leu Leu Leu Leu Gly Val Leu Asn Leu Glu Thr Met
                420                 425

<210> SEQ ID NO 12
<211> LENGTH: 443
<212> TYPE: PRT
<213> ORGANISM: Homo sapiens

<400> SEQUENCE: 12

Met Arg Thr Pro Gln Leu Ala Leu Leu Gln Val Phe Leu Val Phe
1               5                   10                  15

Pro Asp Gly Val Arg Pro Gln Pro Ser Ser Pro Ser Gly Ala Val
                20                  25                  30

Pro Thr Ser Leu Glu Leu Gln Arg Gly Thr Asp Gly Gly Thr Leu Gln
                35                  40                  45

Ser Pro Ser Glu Ala Thr Ala Thr Arg Pro Ala Val Pro Gly Leu Pro
50                  55                  60

Thr Val Val Pro Thr Leu Val Thr Pro Ser Ala Pro Gly Asn Arg Thr
65                  70                  75                  80

Val Asp Leu Phe Pro Val Leu Pro Ile Cys Val Cys Asp Leu Thr Pro
                85                  90                  95

Gly Ala Cys Asp Ile Asn Cys Cys Cys Asp Arg Asp Cys Tyr Leu Leu
                100                 105                 110

His Pro Arg Thr Val Phe Ser Phe Cys Leu Pro Gly Ser Val Arg Ser
                115                 120                 125

Ser Ser Trp Val Cys Val Asp Asn Ser Val Ile Phe Arg Ser Asn Ser
130                 135                 140

Pro Phe Pro Ser Arg Val Phe Met Asp Ser Asn Gly Ile Arg Gln Phe
145                 150                 155                 160

Cys Val His Val Asn Asn Ser Asn Leu Asn Tyr Phe Gln Lys Leu Gln
                165                 170                 175

Lys Val Asn Ala Thr Asn Phe Gln Ala Leu Ala Ala Glu Phe Gly Gly
                180                 185                 190

Glu Ser Phe Thr Ser Thr Phe Gln Thr Gln Ser Pro Pro Ser Phe Tyr
                195                 200                 205

Arg Ala Gly Asp Pro Ile Leu Thr Tyr Phe Pro Lys Trp Ser Val Ile
210                 215                 220

Ser Leu Leu Arg Gln Pro Ala Gly Val Gly Ala Gly Leu Cys Ala
225                 230                 235                 240

Glu Ser Asn Pro Ala Gly Phe Leu Glu Ser Lys Ser Thr Thr Cys Thr
                245                 250                 255

Arg Phe Phe Lys Asn Leu Ala Ser Cys Thr Leu Asp Ser Ala Leu
                260                 265                 270

Asn Ala Ala Ser Tyr Tyr Asn Phe Thr Val Leu Lys Val Pro Arg Ser
                275                 280                 285

Met Thr Asp Pro Gln Asn Met Glu Phe Gln Val Pro Val Ile Leu Thr
                290                 295                 300

Ser Gln Ala Asn Ala Pro Leu Leu Ala Gly Asn Thr Cys Gln Asn Val
305                 310                 315                 320

Val Ser Gln Val Thr Tyr Glu Ile Glu Thr Asn Gly Thr Phe Gly Ile
```

```
                    325                 330                 335
Gln Lys Val Ser Val Ser Leu Gly Gln Thr Asn Leu Thr Val Glu Pro
                340                 345                 350

Gly Ala Ser Leu Gln Gln His Phe Ile Leu Arg Phe Arg Ala Phe Gln
            355                 360                 365

Gln Ser Thr Ala Ala Ser Leu Thr Ser Pro Arg Ser Gly Asn Pro Gly
370                 375                 380

Tyr Ile Val Gly Lys Pro Leu Leu Ala Leu Thr Asp Asp Ile Ser Tyr
385                 390                 395                 400

Ser Val Ser Phe Leu Glu Leu Gly Gly Leu Leu Gln Pro Asn Glu Lys
                405                 410                 415

Ser Cys Lys Gly Phe Gln Thr Tyr Val Arg Leu Ala Lys Gly Glu Glu
            420                 425                 430

Phe Phe Val His Tyr Asn Glu Val Leu Ile Tyr
            435                 440

<210> SEQ ID NO 13
<211> LENGTH: 607
<212> TYPE: PRT
<213> ORGANISM: Homo sapiens

<400> SEQUENCE: 13

Met Arg Thr Pro Gln Leu Ala Leu Leu Gln Val Phe Phe Leu Val Phe
1               5                   10                  15

Pro Asp Gly Val Arg Pro Gln Pro Ser Ser Pro Ser Gly Ala Val
                20                  25                  30

Pro Thr Ser Leu Glu Leu Gln Arg Gly Thr Asp Gly Thr Leu Gln
            35                  40                  45

Ser Pro Ser Glu Ala Thr Ala Thr Arg Pro Ala Val Pro Gly Leu Pro
50                  55                  60

Thr Val Val Pro Thr Leu Val Thr Pro Ser Ala Pro Gly Asn Arg Thr
65                  70                  75                  80

Val Asp Leu Phe Pro Val Leu Pro Ile Cys Val Cys Asp Leu Thr Pro
                85                  90                  95

Gly Ala Cys Asp Ile Asn Cys Cys Cys Asp Arg Asp Cys Tyr Leu Leu
            100                 105                 110

His Pro Arg Thr Val Phe Ser Phe Cys Leu Pro Gly Ser Val Arg Ser
        115                 120                 125

Ser Ser Trp Val Cys Val Asp Asn Ser Val Ile Phe Arg Ser Asn Ser
130                 135                 140

Pro Phe Pro Ser Arg Val Phe Met Asp Ser Asn Gly Ile Arg Gln Phe
145                 150                 155                 160

Cys Val His Val Asn Asn Ser Asn Leu Asn Tyr Phe Gln Lys Leu Gln
                165                 170                 175

Lys Val Asn Ala Thr Asn Phe Gln Ala Leu Ala Ala Glu Phe Gly Gly
            180                 185                 190

Glu Ser Phe Thr Ser Thr Phe Gln Thr Gln Ser Pro Pro Ser Phe Tyr
        195                 200                 205

Arg Ala Gly Asp Pro Ile Leu Thr Tyr Phe Pro Lys Trp Ser Val Ile
    210                 215                 220

Ser Leu Leu Arg Gln Pro Ala Gly Val Gly Ala Gly Gly Leu Cys Ala
225                 230                 235                 240

Glu Ser Asn Pro Ala Gly Phe Leu Glu Ser Lys Ser Thr Thr Cys Thr
                245                 250                 255
```

```
Arg Phe Phe Lys Asn Leu Ala Ser Ser Cys Thr Leu Asp Ser Ala Leu
                260                 265                 270

Asn Ala Ala Ser Tyr Tyr Asn Phe Thr Val Leu Lys Val Pro Arg Ser
            275                 280                 285

Met Thr Asp Pro Gln Asn Met Glu Phe Gln Val Pro Val Ile Leu Thr
290                 295                 300

Ser Gln Ala Asn Ala Pro Leu Leu Ala Gly Asn Thr Cys Gln Asn Val
305                 310                 315                 320

Val Ser Gln Val Thr Tyr Glu Ile Glu Thr Asn Gly Thr Phe Gly Ile
                325                 330                 335

Gln Lys Val Ser Val Ser Leu Gly Gln Thr Asn Leu Thr Val Glu Pro
            340                 345                 350

Gly Ala Ser Leu Gln Gln His Phe Ile Leu Arg Phe Arg Ala Phe Gln
        355                 360                 365

Gln Ser Thr Ala Ala Ser Leu Thr Ser Pro Arg Ser Gly Asn Pro Gly
    370                 375                 380

Tyr Ile Val Gly Lys Pro Leu Ala Leu Thr Asp Asp Ile Ser Tyr
385                 390                 395                 400

Ser Met Thr Leu Leu Gln Ser Gln Gly Asn Gly Ser Cys Ser Val Lys
                405                 410                 415

Arg His Glu Val Gln Phe Gly Val Asn Ala Ile Ser Gly Cys Lys Leu
            420                 425                 430

Arg Leu Lys Lys Ala Asp Cys Ser His Leu Gln Gln Glu Ile Tyr Gln
        435                 440                 445

Thr Leu His Gly Arg Pro Arg Pro Glu Tyr Val Ala Ile Phe Gly Asn
    450                 455                 460

Ala Asp Pro Ala Gln Lys Gly Gly Trp Thr Arg Ile Leu Asn Arg His
465                 470                 475                 480

Cys Ser Ile Ser Ala Ile Asn Cys Thr Ser Cys Leu Ile Pro Val
                485                 490                 495

Ser Leu Glu Ile Gln Val Leu Trp Ala Tyr Val Gly Leu Leu Ser Asn
            500                 505                 510

Pro Gln Ala His Val Ser Gly Val Arg Phe Leu Tyr Gln Cys Gln Ser
        515                 520                 525

Ile Gln Asp Ser Gln Gln Val Thr Glu Val Ser Leu Thr Thr Leu Val
    530                 535                 540

Asn Phe Val Asp Ile Thr Gln Lys Pro Gln Pro Arg Gly Gln Pro
545                 550                 555                 560

Lys Met Asp Trp Lys Trp Pro Phe Asp Phe Pro Phe Lys Val Ala
                565                 570                 575

Phe Ser Arg Gly Val Phe Ser Gln Lys Cys Ser Val Ser Pro Ile Leu
            580                 585                 590

Ile Leu Cys Leu Leu Leu Gly Val Leu Asn Leu Glu Thr Met
        595                 600                 605

<210> SEQ ID NO 14
<211> LENGTH: 106
<212> TYPE: PRT
<213> ORGANISM: Homo sapiens

<400> SEQUENCE: 14

Met Ala Thr Pro Gly Pro Val Ile Pro Glu Val Pro Phe Glu Pro Ser
1               5                   10                  15

Lys Pro Pro Val Ile Glu Gly Leu Ser Pro Thr Val Tyr Arg Asn Pro
            20                  25                  30
```

```
Glu Ser Phe Lys Glu Lys Phe Val Arg Lys Thr Arg Glu Asn Pro Val
            35                  40                  45

Val Pro Ile Gly Cys Leu Ala Thr Ala Ala Ala Leu Thr Tyr Gly Leu
 50                  55                  60

Tyr Ser Phe His Arg Gly Asn Ser Gln Arg Ser Gln Leu Met Met Arg
 65                  70                  75                  80

Thr Arg Ile Ala Ala Gln Gly Phe Thr Val Ala Ala Ile Leu Leu Gly
                 85                  90                  95

Leu Ala Val Thr Ala Met Lys Ser Arg Pro
                100                 105
```

<210> SEQ ID NO 15
<211> LENGTH: 106
<212> TYPE: PRT
<213> ORGANISM: Homo sapiens

<400> SEQUENCE: 15

```
Met Ala Thr Leu Gly Phe Val Thr Pro Glu Ala Pro Phe Glu Ser Ser
 1               5                  10                  15

Lys Pro Pro Ile Phe Glu Gly Leu Ser Pro Thr Val Tyr Ser Asn Pro
                 20                  25                  30

Glu Gly Phe Lys Glu Lys Phe Leu Arg Lys Thr Arg Glu Asn Pro Val
            35                  40                  45

Val Pro Ile Gly Phe Leu Cys Thr Ala Ala Val Leu Thr Asn Gly Leu
 50                  55                  60

Tyr Cys Phe His Gln Gly Asn Ser Gln Cys Ser Arg Leu Met Met His
 65                  70                  75                  80

Thr Gln Ile Ala Ala Gln Gly Phe Thr Ile Ala Ala Ile Leu Leu Gly
                 85                  90                  95

Leu Ala Ala Thr Ala Met Lys Ser Pro Pro
                100                 105
```

<210> SEQ ID NO 16
<211> LENGTH: 132
<212> TYPE: PRT
<213> ORGANISM: Homo sapiens

<400> SEQUENCE: 16

```
Met Cys Ser Ala Gly Glu Leu Leu Arg Gly Gly Asp Gly Gly Glu Arg
 1               5                  10                  15

Asp Glu Asp Gly Asp Ala Leu Ala Glu Arg Glu Ala Ala Gly Thr Gly
                 20                  25                  30

Trp Asp Pro Gly Ala Ser Pro Arg Arg Arg Gly Gln Arg Pro Lys Glu
            35                  40                  45

Ser Glu Gln Asp Val Glu Asp Ser Gln Asn His Thr Gly Glu Pro Val
 50                  55                  60

Gly Asp Asp Tyr Lys Lys Met Gly Thr Leu Phe Gly Glu Leu Asn Lys
 65                  70                  75                  80

Asn Leu Ile Asn Met Gly Phe Thr Arg Met Tyr Phe Gly Glu Arg Ile
                 85                  90                  95

Val Glu Pro Val Ile Val Phe Phe Trp Val Met Leu Trp Phe Leu
                100                 105                 110

Gly Leu Gln Ala Leu Gly Leu Val Ala Val Leu Cys Leu Val Ile Ile
            115                 120                 125

Tyr Val Gln Gln
        130
```

<210> SEQ ID NO 17
<211> LENGTH: 1104
<212> TYPE: PRT
<213> ORGANISM: Homo sapiens

<400> SEQUENCE: 17

```
Met Glu Arg Ser Pro Gly Glu Gly Pro Ser Pro Ser Pro Met Asp Gln
1               5                   10                  15

Pro Ser Ala Pro Ser Asp Pro Thr Asp Gln Pro Pro Ala Ala His Ala
            20                  25                  30

Lys Pro Asp Pro Gly Ser Gly Gly Gln Pro Ala Gly Pro Gly Ala Ala
        35                  40                  45

Gly Glu Ala Leu Ala Val Leu Thr Ser Phe Gly Arg Arg Leu Leu Val
50                  55                  60

Leu Ile Pro Val Tyr Leu Ala Gly Ala Val Gly Leu Ser Val Gly Phe
65                  70                  75                  80

Val Leu Phe Gly Leu Ala Leu Tyr Leu Gly Trp Arg Arg Val Arg Asp
                85                  90                  95

Glu Lys Glu Arg Ser Leu Arg Ala Ala Arg Gln Leu Leu Asp Asp Glu
            100                 105                 110

Glu Gln Leu Thr Ala Lys Thr Leu Tyr Met Ser His Arg Glu Leu Pro
        115                 120                 125

Ala Trp Val Ser Phe Pro Asp Val Glu Lys Ala Glu Trp Leu Asn Lys
130                 135                 140

Ile Val Ala Gln Val Trp Pro Phe Leu Gly Gln Tyr Met Glu Lys Leu
145                 150                 155                 160

Leu Ala Glu Thr Val Ala Pro Ala Val Arg Gly Ser Asn Pro His Leu
                165                 170                 175

Gln Thr Phe Thr Phe Thr Arg Val Glu Leu Gly Glu Lys Pro Leu Arg
            180                 185                 190

Ile Ile Gly Val Lys Val His Pro Gly Gln Arg Lys Glu Gln Ile Leu
        195                 200                 205

Leu Asp Leu Asn Ile Ser Tyr Val Gly Asp Val Gln Ile Asp Val Glu
210                 215                 220

Val Lys Lys Tyr Phe Cys Lys Ala Gly Val Lys Gly Met Gln Leu His
225                 230                 235                 240

Gly Val Leu Arg Val Ile Leu Glu Pro Leu Ile Gly Asp Leu Pro Phe
                245                 250                 255

Val Gly Ala Val Ser Met Phe Phe Ile Arg Arg Pro Thr Leu Asp Ile
            260                 265                 270

Asn Trp Thr Gly Met Thr Asn Leu Leu Asp Ile Pro Gly Leu Ser Ser
        275                 280                 285

Leu Ser Asp Thr Met Ile Met Asp Ser Ile Ala Ala Phe Leu Val Leu
290                 295                 300

Pro Asn Arg Leu Leu Val Pro Leu Val Pro Asp Leu Gln Asp Val Ala
305                 310                 315                 320

Gln Leu Arg Ser Pro Leu Pro Arg Gly Ile Ile Arg Ile His Leu Leu
                325                 330                 335

Ala Ala Arg Gly Leu Ser Ser Lys Asp Lys Tyr Val Lys Gly Leu Ile
            340                 345                 350

Glu Gly Lys Ser Asp Pro Tyr Ala Leu Val Arg Leu Gly Thr Gln Thr
        355                 360                 365

Phe Cys Ser Arg Val Ile Asp Glu Glu Leu Asn Pro Gln Trp Gly Glu
```

-continued

```
            370                 375                 380
Thr Tyr Glu Val Met Val His Glu Val Pro Gly Gln Glu Ile Glu Val
385                 390                 395                 400

Glu Val Phe Asp Lys Asp Pro Asp Lys Asp Asp Phe Leu Gly Arg Met
                405                 410                 415

Lys Leu Asp Val Gly Lys Val Leu Gln Ala Ser Val Leu Asp Asp Trp
                420                 425                 430

Phe Pro Leu Gln Gly Gln Gly Gln Val His Leu Arg Leu Glu Trp
                435                 440                 445

Leu Ser Leu Leu Ser Asp Ala Glu Lys Leu Glu Gln Val Leu Gln Trp
450                 455                 460

Asn Trp Gly Val Ser Ser Arg Pro Asp Pro Ser Ala Ala Ile Leu
465                 470                 475                 480

Val Val Tyr Leu Asp Arg Ala Gln Asp Leu Pro Leu Lys Lys Gly Asn
                485                 490                 495

Lys Glu Pro Asn Pro Met Val Gln Leu Ser Ile Gln Asp Val Thr Gln
                500                 505                 510

Glu Ser Lys Ala Val Tyr Ser Thr Asn Cys Pro Val Trp Glu Glu Ala
                515                 520                 525

Phe Arg Phe Phe Leu Gln Asp Pro Gln Ser Gln Glu Leu Asp Val Gln
530                 535                 540

Val Lys Asp Asp Ser Arg Ala Leu Thr Leu Gly Ala Leu Thr Leu Pro
545                 550                 555                 560

Leu Ala Arg Leu Leu Thr Ala Pro Glu Leu Ile Leu Asp Gln Trp Phe
                565                 570                 575

Gln Leu Ser Ser Ser Gly Pro Asn Ser Arg Leu Tyr Met Lys Leu Val
                580                 585                 590

Met Arg Ile Leu Tyr Leu Asp Ser Ser Glu Ile Cys Phe Pro Thr Val
                595                 600                 605

Pro Gly Cys Pro Gly Ala Trp Asp Val Asp Ser Glu Asn Pro Gln Arg
                610                 615                 620

Gly Ser Ser Val Asp Ala Pro Pro Arg Pro Cys His Thr Thr Pro Asp
625                 630                 635                 640

Ser Gln Phe Gly Thr Glu His Val Leu Arg Ile His Val Leu Glu Ala
                645                 650                 655

Gln Asp Leu Ile Ala Lys Asp Arg Phe Leu Gly Gly Leu Val Lys Gly
                660                 665                 670

Lys Ser Asp Pro Tyr Val Lys Leu Lys Leu Ala Gly Arg Ser Phe Arg
                675                 680                 685

Ser His Val Val Arg Glu Asp Leu Asn Pro Arg Trp Asn Glu Val Phe
690                 695                 700

Glu Val Ile Val Thr Ser Val Pro Gly Gln Glu Leu Glu Val Glu Val
705                 710                 715                 720

Phe Asp Lys Asp Leu Asp Lys Asp Asp Phe Leu Gly Arg Cys Lys Val
                725                 730                 735

Arg Leu Thr Thr Val Leu Asn Ser Gly Phe Leu Asp Glu Trp Leu Thr
                740                 745                 750

Leu Glu Asp Val Pro Ser Gly Arg Leu His Leu Arg Leu Glu Arg Leu
                755                 760                 765

Thr Pro Arg Pro Thr Ala Ala Glu Leu Glu Glu Val Leu Gln Val Asn
                770                 775                 780

Ser Leu Ile Gln Thr Gln Lys Ser Ala Glu Leu Ala Ala Ala Leu Leu
785                 790                 795                 800
```

Ser Ile Tyr Met Glu Arg Ala Glu Asp Leu Pro Leu Arg Lys Gly Thr
            805                 810                 815

Lys His Leu Ser Pro Tyr Ala Thr Leu Thr Val Gly Asp Ser Ser His
        820                 825                 830

Lys Thr Lys Thr Ile Ser Gln Thr Ser Ala Pro Val Trp Asp Glu Ser
    835                 840                 845

Ala Ser Phe Leu Ile Arg Lys Pro His Thr Glu Ser Leu Glu Leu Gln
850                 855                 860

Val Arg Gly Glu Gly Thr Gly Val Leu Gly Ser Leu Ser Leu Pro Leu
865                 870                 875                 880

Ser Glu Leu Leu Val Ala Asp Gln Leu Cys Leu Asp Arg Trp Phe Thr
            885                 890                 895

Leu Ser Ser Gly Gln Gly Gln Val Leu Leu Arg Ala Gln Leu Gly Ile
        900                 905                 910

Leu Val Ser Gln His Ser Gly Val Glu Ala His Ser His Ser Tyr Ser
    915                 920                 925

His Ser Ser Ser Ser Leu Ser Glu Glu Pro Glu Leu Ser Gly Gly Pro
930                 935                 940

Pro His Ile Thr Ser Ser Ala Pro Glu Leu Arg Gln Arg Leu Thr His
945                 950                 955                 960

Val Asp Ser Pro Leu Glu Ala Pro Ala Gly Pro Leu Gly Gln Val Lys
            965                 970                 975

Leu Thr Leu Trp Tyr Tyr Ser Glu Glu Arg Lys Leu Val Ser Ile Val
        980                 985                 990

His Gly Cys Arg Ser Leu Arg Gln Asn Gly Arg Asp Pro Pro Asp Pro
    995                 1000                1005

Tyr Val Ser Leu Leu Leu Leu Pro Asp Lys Asn Arg Gly Thr Lys
    1010                1015                1020

Arg Arg Thr Ser Gln Lys Lys Arg Thr Leu Ser Pro Glu Phe Asn
    1025                1030                1035

Glu Arg Phe Glu Trp Glu Leu Pro Leu Asp Glu Ala Gln Arg Arg
    1040                1045                1050

Lys Leu Asp Val Ser Val Lys Ser Asn Ser Ser Phe Met Ser Arg
    1055                1060                1065

Glu Arg Glu Leu Leu Gly Lys Val Gln Leu Asp Leu Ala Glu Thr
    1070                1075                1080

Asp Leu Ser Gln Gly Val Ala Arg Trp Tyr Asp Leu Met Asp Asn
    1085                1090                1095

Lys Asp Lys Gly Ser Ser
    1100

<210> SEQ ID NO 18
<211> LENGTH: 1114
<212> TYPE: PRT
<213> ORGANISM: Homo sapiens

<400> SEQUENCE: 18

Met Glu Arg Ser Pro Gly Glu Gly Pro Ser Pro Ser Pro Met Asp Gln
1               5                   10                  15

Pro Ser Ala Pro Ser Asp Pro Thr Asp Gln Pro Ala Ala His Ala
            20                  25                  30

Lys Pro Asp Pro Gly Ser Gly Gly Gln Pro Ala Gly Pro Gly Ala Ala
        35                  40                  45

Gly Glu Ala Leu Ala Val Leu Thr Ser Phe Gly Arg Arg Leu Leu Val

```
            50                  55                  60
Leu Ile Pro Val Tyr Leu Ala Gly Ala Val Gly Leu Ser Val Gly Phe
 65                  70                  75                  80

Val Leu Phe Gly Leu Ala Leu Tyr Leu Gly Trp Arg Val Arg Asp
                 85                  90                  95

Glu Lys Glu Arg Ser Leu Arg Ala Ala Arg Gln Leu Leu Asp Asp Glu
                100                 105                 110

Glu Gln Leu Thr Ala Lys Thr Leu Tyr Met Ser His Arg Glu Leu Pro
            115                 120                 125

Ala Trp Val Ser Phe Pro Asp Val Glu Lys Ala Glu Trp Leu Asn Lys
130                 135                 140

Ile Val Ala Gln Val Trp Pro Phe Leu Gly Gln Tyr Met Glu Lys Leu
145                 150                 155                 160

Leu Ala Glu Thr Val Ala Pro Ala Val Arg Gly Ser Asn Pro His Leu
                165                 170                 175

Gln Thr Phe Thr Phe Thr Arg Val Glu Leu Gly Glu Lys Pro Leu Arg
            180                 185                 190

Ile Ile Gly Val Lys Val His Pro Gly Gln Arg Lys Glu Gln Ile Leu
            195                 200                 205

Leu Asp Leu Asn Ile Ser Tyr Val Gly Asp Val Gln Ile Asp Val Glu
210                 215                 220

Val Lys Lys Tyr Phe Cys Lys Ala Gly Val Lys Gly Met Gln Leu His
225                 230                 235                 240

Gly Val Leu Arg Val Ile Leu Glu Pro Leu Ile Gly Asp Leu Pro Phe
                245                 250                 255

Val Gly Ala Val Ser Met Phe Phe Ile Arg Arg Pro Thr Leu Asp Ile
                260                 265                 270

Asn Trp Thr Gly Met Thr Asn Leu Leu Asp Ile Pro Gly Leu Ser Ser
                275                 280                 285

Leu Ser Asp Thr Met Ile Met Asp Ser Ile Ala Ala Phe Leu Val Leu
            290                 295                 300

Pro Asn Arg Leu Leu Val Pro Leu Val Pro Asp Leu Gln Asp Val Ala
305                 310                 315                 320

Gln Leu Arg Ser Pro Leu Pro Arg Gly Ile Ile Arg Ile His Leu Leu
                325                 330                 335

Ala Ala Arg Gly Leu Ser Ser Lys Asp Lys Tyr Val Lys Gly Leu Ile
            340                 345                 350

Glu Gly Lys Ser Asp Pro Tyr Ala Leu Val Arg Leu Gly Thr Gln Thr
            355                 360                 365

Phe Cys Ser Arg Val Ile Asp Glu Glu Leu Asn Pro Gln Trp Gly Glu
370                 375                 380

Thr Tyr Glu Val Met Val His Glu Val Pro Gly Gln Glu Ile Glu Val
385                 390                 395                 400

Glu Val Phe Asp Lys Asp Pro Asp Lys Asp Asp Phe Leu Gly Arg Met
                405                 410                 415

Lys Leu Asp Val Gly Lys Val Leu Gln Ala Ser Val Leu Asp Asp Trp
                420                 425                 430

Phe Pro Leu Gln Gly Gly Gln Gly Gln Val His Leu Arg Leu Glu Trp
            435                 440                 445

Leu Ser Leu Leu Ser Asp Ala Glu Lys Leu Glu Gln Val Leu Gln Trp
450                 455                 460

Asn Trp Gly Val Ser Ser Arg Pro Asp Pro Pro Ser Ala Ala Ile Leu
465                 470                 475                 480
```

```
Val Val Tyr Leu Asp Arg Ala Gln Asp Leu Pro Met Val Thr Ser Glu
            485                 490                 495

Leu Tyr Pro Pro Gln Leu Lys Lys Gly Asn Lys Glu Pro Asn Pro Met
            500                 505                 510

Val Gln Leu Ser Ile Gln Asp Val Thr Gln Glu Ser Lys Ala Val Tyr
            515                 520                 525

Ser Thr Asn Cys Pro Val Trp Glu Glu Ala Phe Arg Phe Phe Leu Gln
            530                 535                 540

Asp Pro Gln Ser Gln Glu Leu Asp Val Gln Val Lys Asp Asp Ser Arg
545                 550                 555                 560

Ala Leu Thr Leu Gly Ala Leu Thr Leu Pro Leu Ala Arg Leu Leu Thr
            565                 570                 575

Ala Pro Glu Leu Ile Leu Asp Gln Trp Phe Gln Leu Ser Ser Ser Gly
            580                 585                 590

Pro Asn Ser Arg Leu Tyr Met Lys Leu Val Met Arg Ile Leu Tyr Leu
            595                 600                 605

Asp Ser Ser Glu Ile Cys Phe Pro Thr Val Pro Gly Cys Pro Gly Ala
            610                 615                 620

Trp Asp Val Asp Ser Glu Asn Pro Gln Arg Gly Ser Ser Val Asp Ala
625                 630                 635                 640

Pro Pro Arg Pro Cys His Thr Thr Pro Asp Ser Gln Phe Gly Thr Glu
            645                 650                 655

His Val Leu Arg Ile His Val Leu Glu Ala Gln Asp Leu Ile Ala Lys
            660                 665                 670

Asp Arg Phe Leu Gly Gly Leu Val Gly Lys Ser Asp Pro Tyr Val
            675                 680                 685

Lys Leu Lys Leu Ala Gly Arg Ser Phe Arg Ser His Val Val Arg Glu
            690                 695                 700

Asp Leu Asn Pro Arg Trp Asn Glu Val Phe Glu Val Ile Val Thr Ser
705                 710                 715                 720

Val Pro Gly Gln Glu Leu Glu Val Glu Val Phe Asp Lys Asp Leu Asp
            725                 730                 735

Lys Asp Asp Phe Leu Gly Arg Cys Lys Val Arg Leu Thr Thr Val Leu
            740                 745                 750

Asn Ser Gly Phe Leu Asp Glu Trp Leu Thr Leu Glu Asp Val Pro Ser
            755                 760                 765

Gly Arg Leu His Leu Arg Leu Glu Arg Leu Thr Pro Arg Pro Thr Ala
            770                 775                 780

Ala Glu Leu Glu Glu Val Leu Gln Val Asn Ser Leu Ile Gln Thr Gln
785                 790                 795                 800

Lys Ser Ala Glu Leu Ala Ala Ala Leu Leu Ser Ile Tyr Met Glu Arg
            805                 810                 815

Ala Glu Asp Leu Pro Leu Arg Lys Gly Thr Lys His Leu Ser Pro Tyr
            820                 825                 830

Ala Thr Leu Thr Val Gly Asp Ser Ser His Lys Thr Lys Thr Ile Ser
            835                 840                 845

Gln Thr Ser Ala Pro Val Trp Asp Glu Ser Ala Ser Phe Leu Ile Arg
            850                 855                 860

Lys Pro His Thr Glu Ser Leu Glu Leu Gln Val Arg Gly Glu Gly Thr
865                 870                 875                 880

Gly Val Leu Gly Ser Leu Ser Leu Pro Leu Ser Glu Leu Leu Val Ala
            885                 890                 895
```

```
Asp Gln Leu Cys Leu Asp Arg Trp Phe Thr Leu Ser Ser Gly Gln Gly
            900                 905                 910

Gln Val Leu Leu Arg Ala Gln Leu Gly Ile Leu Val Ser Gln His Ser
        915                 920                 925

Gly Val Glu Ala His Ser His Ser Tyr Ser His Ser Ser Ser Ser Leu
    930                 935                 940

Ser Glu Glu Pro Glu Leu Ser Gly Gly Pro Pro His Ile Thr Ser Ser
945                 950                 955                 960

Ala Pro Glu Leu Arg Gln Arg Leu Thr His Val Asp Ser Pro Leu Glu
                965                 970                 975

Ala Pro Ala Gly Pro Leu Gly Gln Val Lys Leu Thr Leu Trp Tyr Tyr
            980                 985                 990

Ser Glu Glu Arg Lys Leu Val Ser Ile Val His Gly Cys Arg Ser Leu
        995                 1000                1005

Arg Gln Asn Gly Arg Asp Pro Pro Asp Pro Tyr Val Ser Leu Leu
    1010                1015                1020

Leu Leu Pro Asp Lys Asn Arg Gly Thr Lys Arg Arg Thr Ser Gln
    1025                1030                1035

Lys Lys Arg Thr Leu Ser Pro Glu Phe Asn Glu Arg Phe Glu Trp
    1040                1045                1050

Glu Leu Pro Leu Asp Glu Ala Gln Arg Arg Lys Leu Asp Val Ser
    1055                1060                1065

Val Lys Ser Asn Ser Ser Phe Met Ser Arg Glu Arg Glu Leu Leu
    1070                1075                1080

Gly Lys Val Gln Leu Asp Leu Ala Glu Thr Asp Leu Ser Gln Gly
    1085                1090                1095

Val Ala Arg Trp Tyr Asp Leu Met Asp Asn Lys Asp Lys Gly Ser
    1100                1105                1110

Ser

<210> SEQ ID NO 19
<211> LENGTH: 1104
<212> TYPE: PRT
<213> ORGANISM: Homo sapiens

<400> SEQUENCE: 19

Met Glu Arg Ser Pro Gly Glu Gly Pro Ser Pro Ser Pro Met Asp Gln
1               5                   10                  15

Pro Ser Ala Pro Ser Asp Pro Thr Asp Gln Pro Pro Ala Ala His Ala
            20                  25                  30

Lys Pro Asp Pro Gly Ser Gly Gly Gln Pro Ala Gly Pro Gly Ala Ala
        35                  40                  45

Gly Glu Ala Leu Ala Val Leu Thr Ser Phe Gly Arg Arg Leu Leu Val
    50                  55                  60

Leu Ile Pro Val Tyr Leu Ala Gly Ala Val Gly Leu Ser Val Gly Phe
65                  70                  75                  80

Val Leu Phe Gly Leu Ala Leu Tyr Leu Gly Trp Arg Arg Val Arg Asp
            85                  90                  95

Glu Lys Glu Arg Ser Leu Arg Ala Ala Arg Gln Leu Leu Asp Asp Glu
            100                 105                 110

Glu Gln Leu Thr Ala Lys Thr Leu Tyr Met Ser His Arg Glu Leu Pro
        115                 120                 125

Ala Trp Val Ser Phe Pro Asp Val Glu Lys Ala Glu Trp Leu Asn Lys
    130                 135                 140
```

```
Ile Val Ala Gln Val Trp Pro Phe Leu Gly Gln Tyr Met Glu Lys Leu
145                 150                 155                 160

Leu Ala Glu Thr Val Ala Pro Ala Val Arg Gly Ser Asn Pro His Leu
            165                 170                 175

Gln Thr Phe Thr Phe Thr Arg Val Glu Leu Gly Glu Lys Pro Leu Arg
        180                 185                 190

Ile Ile Gly Val Lys Val His Pro Gly Gln Arg Lys Glu Gln Ile Leu
    195                 200                 205

Leu Asp Leu Asn Ile Ser Tyr Val Gly Asp Val Gln Ile Asp Val Glu
210                 215                 220

Val Lys Lys Tyr Phe Cys Lys Ala Gly Val Lys Gly Met Gln Leu His
225                 230                 235                 240

Gly Val Leu Arg Val Ile Leu Glu Pro Leu Ile Gly Asp Leu Pro Phe
            245                 250                 255

Val Gly Ala Val Ser Met Phe Phe Ile Arg Arg Pro Thr Leu Asp Ile
        260                 265                 270

Asn Trp Thr Gly Met Thr Asn Leu Leu Asp Ile Pro Gly Leu Ser Ser
    275                 280                 285

Leu Ser Asp Thr Met Ile Met Asp Ser Ile Ala Ala Phe Leu Val Leu
290                 295                 300

Pro Asn Arg Leu Leu Val Pro Leu Val Pro Asp Leu Gln Asp Val Ala
305                 310                 315                 320

Gln Leu Arg Ser Pro Leu Pro Arg Gly Ile Ile Arg Ile His Leu Leu
            325                 330                 335

Ala Ala Arg Gly Leu Ser Ser Lys Asp Lys Tyr Val Lys Gly Leu Ile
        340                 345                 350

Glu Gly Lys Ser Asp Pro Tyr Ala Leu Val Arg Leu Gly Thr Gln Thr
    355                 360                 365

Phe Cys Ser Arg Val Ile Asp Glu Glu Leu Asn Pro Gln Trp Gly Glu
370                 375                 380

Thr Tyr Glu Val Met Val His Glu Val Pro Gly Gln Glu Ile Glu Val
385                 390                 395                 400

Glu Val Phe Asp Lys Asp Pro Asp Lys Asp Asp Phe Leu Gly Arg Met
            405                 410                 415

Lys Leu Asp Val Gly Lys Val Leu Gln Ala Ser Val Leu Asp Asp Trp
        420                 425                 430

Phe Pro Leu Gln Gly Gly Gln Gly Gln Val His Leu Arg Leu Glu Trp
    435                 440                 445

Leu Ser Leu Leu Ser Asp Ala Glu Lys Leu Glu Gln Val Leu Gln Trp
450                 455                 460

Asn Trp Gly Val Ser Ser Arg Pro Asp Pro Ser Ala Ala Ile Leu
465                 470                 475                 480

Val Val Tyr Leu Asp Arg Ala Gln Asp Leu Pro Leu Lys Lys Gly Asn
            485                 490                 495

Lys Glu Pro Asn Pro Met Val Gln Leu Ser Ile Gln Asp Val Thr Gln
        500                 505                 510

Glu Ser Lys Ala Val Tyr Ser Thr Asn Cys Pro Val Trp Glu Glu Ala
    515                 520                 525

Phe Arg Phe Phe Leu Gln Asp Pro Gln Ser Gln Glu Leu Asp Val Gln
530                 535                 540

Val Lys Asp Asp Ser Arg Ala Leu Thr Leu Gly Ala Leu Thr Leu Pro
545                 550                 555                 560

Leu Ala Arg Leu Leu Thr Ala Pro Glu Leu Ile Leu Asp Gln Trp Phe
```

-continued

```
                565                 570                 575
    Gln Leu Ser Ser Ser Gly Pro Asn Ser Arg Leu Tyr Met Lys Leu Val
                580                 585                 590

Met Arg Ile Leu Tyr Leu Asp Ser Ser Glu Ile Cys Phe Pro Thr Val
                595                 600                 605

Pro Gly Cys Pro Gly Ala Trp Asp Val Asp Ser Glu Asn Pro Gln Arg
                610                 615                 620

Gly Ser Ser Val Asp Ala Pro Pro Arg Pro Cys His Thr Thr Pro Asp
    625                 630                 635                 640

Ser Gln Phe Gly Thr Glu His Val Leu Arg Ile His Val Leu Glu Ala
                    645                 650                 655

Gln Asp Leu Ile Ala Lys Asp Arg Phe Leu Gly Gly Leu Val Lys Gly
                660                 665                 670

Lys Ser Asp Pro Tyr Val Lys Leu Lys Leu Ala Gly Arg Ser Phe Arg
                675                 680                 685

Ser His Val Val Arg Glu Asp Leu Asn Pro Arg Trp Asn Glu Val Phe
                690                 695                 700

Glu Val Ile Val Thr Ser Val Pro Gly Gln Glu Leu Glu Val Glu Val
    705                 710                 715                 720

Phe Asp Lys Asp Leu Asp Lys Asp Phe Leu Gly Arg Cys Lys Val
                    725                 730                 735

Arg Leu Thr Thr Val Leu Asn Ser Gly Phe Leu Asp Glu Trp Leu Thr
                740                 745                 750

Leu Glu Asp Val Pro Ser Gly Arg Leu His Leu Arg Leu Glu Arg Leu
                755                 760                 765

Thr Pro Arg Pro Thr Ala Ala Glu Leu Glu Glu Val Leu Gln Val Asn
    770                 775                 780

Ser Leu Ile Gln Thr Gln Lys Ser Ala Glu Leu Ala Ala Ala Leu Leu
    785                 790                 795                 800

Ser Ile Tyr Met Glu Arg Ala Glu Asp Leu Pro Leu Arg Lys Gly Thr
                805                 810                 815

Lys His Leu Ser Pro Tyr Ala Thr Leu Thr Val Gly Asp Ser Ser His
                820                 825                 830

Lys Thr Lys Thr Ile Ser Gln Thr Ser Ala Pro Val Trp Asp Glu Ser
                835                 840                 845

Ala Ser Phe Leu Ile Arg Lys Pro His Thr Glu Ser Leu Glu Leu Gln
    850                 855                 860

Val Arg Gly Glu Gly Thr Gly Val Leu Gly Ser Leu Ser Leu Pro Leu
    865                 870                 875                 880

Ser Glu Leu Leu Val Ala Asp Gln Leu Cys Leu Asp Arg Trp Phe Thr
                    885                 890                 895

Leu Ser Ser Gly Gln Gly Gln Val Leu Leu Arg Ala Gln Leu Gly Ile
                900                 905                 910

Leu Val Ser Gln His Ser Gly Val Glu Ala His Ser His Ser Tyr Ser
                915                 920                 925

His Ser Ser Ser Ser Leu Ser Glu Glu Pro Glu Leu Ser Gly Gly Pro
                930                 935                 940

Pro His Ile Thr Ser Ser Ala Pro Glu Leu Arg Gln Arg Leu Thr His
    945                 950                 955                 960

Val Asp Ser Pro Leu Glu Ala Pro Ala Gly Pro Leu Gly Gln Val Lys
                    965                 970                 975

Leu Thr Leu Trp Tyr Tyr Ser Glu Glu Arg Lys Leu Val Ser Ile Val
                980                 985                 990
```

```
His Gly Cys Arg Ser Leu Arg Gln Asn Gly Arg Asp Pro Pro Asp Pro
        995                 1000                1005

Tyr Val Ser Leu Leu Leu Leu Pro Asp Lys Asn Arg Gly Thr Lys
   1010                1015                1020

Arg Arg Thr Ser Gln Lys Lys Arg Thr Leu Ser Pro Glu Phe Asn
   1025                1030                1035

Glu Arg Phe Glu Trp Glu Leu Pro Leu Asp Glu Ala Gln Arg Arg
   1040                1045                1050

Lys Leu Asp Val Ser Val Lys Ser Asn Ser Ser Phe Met Ser Arg
   1055                1060                1065

Glu Arg Glu Leu Leu Gly Lys Val Gln Leu Asp Leu Ala Glu Thr
   1070                1075                1080

Asp Leu Ser Gln Gly Val Ala Arg Trp Tyr Asp Leu Met Asp Asn
   1085                1090                1095

Lys Asp Lys Gly Ser Ser
   1100

<210> SEQ ID NO 20
<211> LENGTH: 1667
<212> TYPE: DNA
<213> ORGANISM: Homo sapiens

<400> SEQUENCE: 20
gcaacgcgct gtccatgtcg cgggcctcgc tgggactccc tgggagatga ggccgcgagg      60
tctcccgccg ctcctggtgg tgctcctggg ctgctgggcc tccgtgagcg cccagaccga    120
tgccaccccg gcggtgacga cagagggcct caactccacc gaggcagccc tggccacctt    180
cggaactttc ccgtcgacca ggcccccagg gactcccagg gctccagggc cctcctccgg    240
ccccaggcct accccagtca cggacgttgc tgttctctgt gtctgtgact atccccagc     300 acagtgtgac atcaactgct gctgtgatcc cgactgcagc tccgtggatt tcagtgtctt    360
ttctgcctgc tcagttccag ttgtcacggg cgacagccag ttttgtagtc aaaaagcagt    420
catctattca ttgaatttta cagcaaaccc acctcaaaga gtatttgaac ttgttgacca    480
gattaatcca tctatttct gcattcatat tacaaactat aaacctgcat tatcctttat    540
taatccagaa gtacctgatg aaaacaattt tgatacattg atgaaaacat ctgatggttt    600
tacattgaat gctgaatcat atgtttcctt cacaaccaaa ctggatattc ctactgctgc    660
taaatatgag tatggggttc ctctgcagac ttcagattcg tttctgagat tccttcgtc     720 cctgacatca tctctgtgca ctgataataa ccctgcagcg tttctggtga accaggctgt    780
taagtgcacc agaaaaataa atttagaaca gtgtgaagaa attgaagccc tcagcatggc    840 ttttttacagc agcccggaaa ttctgagggt acctgattca agaaaaaagg tccctatcac    900
tgttcagtcc atcgtcattc agtctctaaa taaaacgctc acccgacggg aggacactga    960
tgtgctgcag ccgactctcg tcaacgctgg acactttagc ctttgcgtga atgttgttct   1020
tgaggtaaag tacagcctca catacacaga tgcaggtgaa gtcaccaaag ctgatctctc   1080
attcgttctg gggacagtta gcagcgtagt ggtcccactg cagcaaaagt ttgaaattca   1140
ttttcttcag actgactgga gctctcccgt gtcagctcgt agcacagaag gtgaagagcc   1200
tgctgtgggg ccagggcttc ccagattacg tggccccttt tggaaattcc aggcccagg    1260 acatgctgga ctgggtgccc atccacttca tcacccagtc attcaacagg aaggattcct   1320
gccagctccc aggggctttg gttatagaag tgaagtggac taaatacgga tccctgctga   1380
```

| atccacaggc caaaatagtc aatgtaactg caaatctaat ttcatcctcc tttcctgagg | 1440 |
| ccaactcagg aaatgaaagg acgattctta tttccactgc ggttactttt gtggatgtgt | 1500 |
| ctgcacctgc agaggcaggc ttcagagctc caccagccat caatgccagg ctgcccttta | 1560 |
| acttcttctt cccgtttgtt tgacaatgct cagatgcatc agttccttaa tatacacgtg | 1620 |
| aaatttgaaa actgtacatt cggtgagatt aaattttata taaaact | 1667 |

<210> SEQ ID NO 21
<211> LENGTH: 1536
<212> TYPE: DNA
<213> ORGANISM: Homo sapiens

<400> SEQUENCE: 21

| atgatcacag ctcactgcag cctcgacctc ctaggctcag ttgctgttct ctgtgtctgt | 60 |
| gacttatccc agcacagtg tgacatcaac tgctgctgtg atcccgactg cagctccgtg | 120 |
| gatttcagtg tcttttctgc ctgctcagtt ccagttgtca cgggcgacag ccagttttgt | 180 |
| agtcaaaaag cagtcatcta ttcattgaat tttacagcaa accacctca aagagtattt | 240 |
| gaacttgttg accagattaa tccatctatt ttctgcattc atattacaaa ctataaacct | 300 |
| gcattatcct ttattaatcc agaagtacct gatgaaaaca ttttgatac attgatgaaa | 360 |
| acatctgatg gttttacatt gaatgctgaa tcatatgttt ccttcacaac caaactggat | 420 |
| attcctactg ctgctaaata tgagtatggg gttcctctgc agacttcaga ttcgtttctg | 480 |
| agatttcctt cgtccctgac atcatctctg tgcactgata taaccctgc agcgtttctg | 540 |
| gtgaaccagg ctgttaagtg caccagaaaa ataaatttag aacagtgtga agaaattgaa | 600 |
| gccctcagca tggcttttta cagcagcccg gaaattctga gggtacctga ttcaagaaaa | 660 |
| aaggtcccta tcactgttca gtccatcgtc attcagtctc taaataaaac gctcacccga | 720 |
| cgggaggaca ctgatgtgct gcagccgact ctcgtcaacg ctggacactt tagcctttgc | 780 |
| gtgaatgttg ttcttgaggt aaagtacagc ctcacataca cagatgcagg tgaagtcacc | 840 |
| aaagctgatc tctcattcgt tctggggaca gttagcagcg tagtggtccc actgcagcaa | 900 |
| aagtttgaaa ttcattttct tcaggaaaat acccagccag tccctctcag tggaaaccct | 960 |
| ggttatgtcg tggggctccc attagctgct ggattccagc ctcataagac tggagctctc | 1020 |
| ccgtgtcagc tcgtagcaca gaaggtgaag agcctgctgt ggggccaggg cttcccagat | 1080 |
| tacgtggccc cttttggaaa ttcccaggcc caggacatgc tggactgggt gcccatccac | 1140 |
| ttcatcaccc agtcattcaa caggaagcat tttgttttgc aggattcctg ccagctccca | 1200 |
| ggggctttgg ttatagaagt gaagtggact aaatacggat ccctgctgaa tccacaggcc | 1260 |
| aaaatagtca atgtaactgc aaatctaatt tcatcctcct ttcctgaggc caactcagga | 1320 |
| aatgaaagga cgattcttat ttccactgcg gttacttttg tggatgtgtc tgcacctgca | 1380 |
| gaggcaggct tcagagctcc accagccatc aatgccaggc tgccctttaa cttcttcttc | 1440 |
| ccgtttgttt gacaatgctc agatgcatca gttccttaat atacacgtga aatttgaaaa | 1500 |
| ctgtacattc ggtgagatta aattttatat acaact | 1536 |

<210> SEQ ID NO 22
<211> LENGTH: 1680
<212> TYPE: DNA
<213> ORGANISM: Homo sapiens

<400> SEQUENCE: 22

| atgtgccagc tcctggagtc cacagtgatc caacctcaag gggacagccc cgttgctgtt | 60 |

```
ctctgtgtct gtgacttatc cccagcacag tgtgacatca actgctgctg tgatcccgac        120
tgcagctccg tggatttcag tgtcttttct gcctgctcag ttccagttgt cacgggcgac        180
agccagtttt gtagtcaaaa agcagtcatc tattcattga attttacagc aaacccacct        240
caaagagtat ttgaacttgt tgaccagatt aatccatcta tttctgcat tcatattaca        300 aactataaac ctgcattatc ctttattaat ccagaagtac ctgatgaaaa caattttgat        360
acattgatga aaacatctga tggttttaca ttgaatgctg aatcatatgt ttccttcaca        420
accaaactgg atattcctac tgctgctaaa tatgagtatg ggttcctct gcagacttca        480 gattcgtttc tgagatttcc ttcgtccctg acatcatctc tgtgcactga taataaccct        540
gcagcgtttc tggtgaacca ggctgttaag tgcaccagaa aaataaattt agaacagtgt        600
gaagaaattg aagccctcag catggctttt tacagcagcc cggaaattct gagggtacct        660
gattcaagaa aaaggtccc tatcactgtt cagtccatcg tcattcagtc tctaaataaa        720
acgctcaccc gacgggagga cactgatgtg ctgcagccga ctctcgtcaa cgctggacac        780
tttagccttt gcgtgaatgt tgttcttgag gtaaagtaca gcctcacata cacagatgca        840
ggtgaagtca ccaaagctga tctctcattc gttctgggga cagttagcag cgtagtggtc        900
ccactgcagc aaaagtttga aattcatttt cttcaggaaa atacccagcc agtccctctc        960
agtggaaacc ctggttatgt cgtggggctc ccattagctg ctggattcca gcctcataag       1020
atgtctggga ttattcagac cacaaataga tatggacagc ttactattct tcatagcaca       1080
actgagcaag actgcttagc actggagggg gtccggaccc cagtattatt tggttacact       1140
atgcaatctg gctgtaaact aagactgact ggagctctcc cgtgtcagct cgtagcacag       1200
aaggtgaaga gcctgctgtg gggccagggc ttcccagatt acgtggcccc ttttggaaat       1260
tcccaggccc aggacatgct ggactgggtg cccatccact catcaccca gtcattcaac       1320 aggaaggatt cctgccagct cccaggggct ttggttatag aagtgaagtg gactaaaatac      1380 ggatccctgc tgaatccaca ggccaaaata gtcaatgtaa ctgcaaatct aatttcatcc       1440
tcctttcctg aggccaactc aggaaatgaa aggacgattc ttatttccac tgcggttact       1500
tttgtggatg tgtctgcacc tgcagaggca ggcttcagag ctccaccagc catcaatgcc       1560
aggctgccct ttaacttctt cttcccgttt gtttgacaat gctcagatgc atcagttcct       1620
taatatacac gtgaaatttg aaaactgtac attcggtgag attaaattttt atatacaact      1680
```

<210> SEQ ID NO 23
<211> LENGTH: 1885
<212> TYPE: DNA
<213> ORGANISM: Homo sapiens

<400> SEQUENCE: 23

```
cgctgggact ccctgggaga tgaggccgcg aggtctcccg ccgctcctgg tggtgctcct         60
gggctgctgg gcctccgtga cgcccagac cgatgccacc ccggcggtga cgacagaggg        120
cctcaactcc accgaggcag ccctggccac cttcggaact ttcccgtcga ccaggccccc        180
cgggactccc agggctccag ggccctcctc cggcccagg cctacccag tcacggacgt        240 tgctgttctc tgtgtctgtg acttatcccc agcacagtgt gacatcaact gctgctgtga       300
tcccgactgc agctccgtgg atttcagtgt cttttctgcc tgctcagttc agttgtcac       360 gggcgacagc cagttttgta gtcaaaaagc agtcatctat tcattgaatt ttacagcaaa       420
cccacctcaa agagtatttg aacttgttga ccagattaat ccatctattt tctgcattca       480
```

```
tattacaaac tataaacctg cattatcctt tattaatcca gaagtacctg atgaaaacaa    540
ttttgataca ttgatgaaaa catctgatgg ttttacattg aatgctgaat catatgtttc    600
cttcacaacc aaactggata ttcctactgc tgctaaatat gagtatgggg ttcctctgca    660
gacttcagat tcgtttctga gatttccttc gtccctgaca tcatctctgt gcactgataa    720
taaccctgca gcgtttctgg tgaaccaggc tgttaagtgc accagaaaaa taaatttaga    780
acagtgtgaa gaaattgaag ccctcagcat ggcttttttac agcagcccgg aaattctgag    840
ggtacctgat tcaagaaaaa aggtccctat cactgttcag tccatcgtca ttcagtctct    900
aaataaaacg ctcacccgac gggaggacac tgatgtgctg cagccgactc tcgtcaacgc    960
tggacacttt agcctttgcg tgaatgttgt tcttgaggta aagtacagcc tcacatacac   1020
agatgcaggt gaagtcacca agctgatct ctcattcgtt ctggggacag ttagcagcgt   1080
agtggtccca ctgcagcaaa agtttgaaat tcatttctt caggaaaata cccagccagt   1140
ccctctcagt ggaaacctg gttatgtcgt ggggctccca ttagctgctg gattccagcc   1200
tcataagggg tctgggatta ttcagaccac aaatagatat ggacagctta ctattcttca   1260
tagcacaact gagcaagact gcttagcact ggagggggtc cggaccccag tattatttgg   1320
ttacactatg caatctggct gtaaactaag actgactgga gctctcccgt gtcagctcgt   1380
agcacagaag gtgaagagcc tgctgtgggg ccagggcttc ccagattacg tggccccttt   1440
tggaaattcc caggcccagg acatgctgga ctgggtgccc atccacttca tcacccagtc   1500
attcaacagg aagcattttg ttttgcagga ttcctgccag ctcccagggg ctttggttat   1560
agaagtgaag tggactaaat acggatccct gctgaatcca caggccaaaa tagtcaatgt   1620
aactgcaaat ctaatttcat cctcctttcc tgaggccaac tcaggaaatg aaaggacgat   1680
tcttatttcc actgcggtta cttttgtgga tgtgtctgca cctgcagagg caggcttcag   1740
agctccacca gccatcaatg ccaggctgcc ctttaacttc ttcttcccgt tgtttgaca    1800 atgctcagat gcatcagttc cttaatatac acgtgaaatt tgaaaactgt acattcggtg   1860
agattaaatt ttatatacaa ctagc                                        1885

<210> SEQ ID NO 24
<211> LENGTH: 1879
<212> TYPE: DNA
<213> ORGANISM: Homo sapiens

<400> SEQUENCE: 24
gcgcctggct gtcgcggttg ccgggcaacg cgctgtccat gtcgcgggcc tcgctgggac     60
tccctgggag atgaggccgc gaggtctccc gccgctcctg gtggtgctcc tgggctgctg    120
ggcctccgtg agcgcccaga ccgatgccac cccggcggtg acgacagagg gcctcaactc    180
caccgaggca gccctggcca ccttcggaac tttccgtcg accaggcccc ccgggactcc    240
cagggctcca gggcccctcct ccggccccag gcctacccca gtcacggacg ttgctgttct    300
ctgtgtctgt gacttatccc cagcacagtg tgacatcaac tgctgctgtg atcccgactg    360
cagctccgtg gatttcagtg tcttttctgc ctgctcagtt ccagttgtca cgggcgacag    420
ccagttttgt agtcaaaaag cagtcatcta ttcattgaat tttacagcaa acccaccctca    480 aagagtattt gaacttgttg accagattaa tccatctatt ttctgcattc atattacaaa    540
ctataaacct gcattatcct ttattaatcc agaagtacct gatgaaaaca attttgatac    600
attgatgaaa acatctgatg gttttacatt gaatgctgaa tcatatgttt ccttcacaac    660
caaactggat attcctactg ctgctaaata tgagtatggg gttcctctgc agacttcaga    720
```

```
ttcgtttctg agatttcctt cgtccctgac atcatctctg tgcactgata ataaccctgc      780
aggccaggcg tactggttca cacctgtaat cccagcactc tgggaggccg aggcgagagg      840
atcacttgag gtacctgatt caagaaaaaa ggtccctatc actgttcagt ccatcgtcat      900
tcagtctcta aataaaacgc tcacccgacg ggaggacact gatgtgctgc agccgactct      960
cgtcaacgct ggacactttta gcctttgcgt gaatgttgtt cttgaggtaa agtacagcct     1020
cacatacaca gatgcaggtg aagtcaccaa agctgatctc tcattcgttc tggggacagt     1080
tagcagcgta gtggtcccac tgcagcaaaa gtttgaaatt cattttcttc aggaaaatac     1140
ccagccagtc cctctcagtg gaaaccctgg ttatgtcgtg gggctcccat agctgctgg      1200 attccagcct cataaggggt ctgggattat tcagaccaca aatagatatg gacagcttac     1260
tattcttcat agcacaactg agcaagactg cttagcactg gaggggggtcc ggaccccagt    1320 attatttggt tacactatgc aatctggctg taaactaaga ctgactggag ctctcccgtg     1380
tcagctcgta gcacagaagg tgaagagcct gctgtggggc cagggcttcc cagattacgt     1440 ggccccttt ggaaattccc aggcccagga catgctggac tgggtgccca tccacttcat      1500
cacccagtca ttcaacagga aggattcctg ccagctccca ggggctttgg ttatagaagt     1560
gaagtggact aaatacggat ccctgctgaa tccacaggcc aaaatagtca atgtaactgc     1620
aaatctaatt tcatcctcct ttcctgaggc caactcagga aatgaaagga cgattcttat     1680
ttccactgcg gttacttttg tggatgtgtc tgcacctgca gaggcaggct tcagagctcc     1740
accagccatc aatgccaggc tgccctttaa cttcttcttc ccgttttgtttt gacaatgctc    1800 agatgcatca gttccttaat atacacgtga aatttgaaaa ctgtacattc ggtgagatta     1860
aattttatat acaactagc                                                   1879

<210> SEQ ID NO 25
<211> LENGTH: 1932
<212> TYPE: DNA
<213> ORGANISM: Homo sapiens

<400> SEQUENCE: 25
cgtgatgccc cgcgcctggc tgtcgcggtt gccgggcaac gcgctgtcca tgtcgcgggc       60
ctcgctggga ctccctggga gatgaggccg cgaggtctcc cgccgctcct ggtggtgctc      120
ctgggctgct gggcctccgt gagcgcccag accgatgcca ccccggcggt gacgacagag      180
ggcctcaact ccaccgaggc agccctggcc accttcggaa ctttcccgtc gaccaggccc      240
cccgggactc ccagggctcc agggccctcc tccggcccca ggcctacccc agtcacggac      300
gttgctgttc tctgtgtctg tgacttatcc ccagcacagt gtgacatcaa ctgctgctgt      360
gatcccgact gcagctccgt ggatttcagt gtcttttctg cctgctcagt tccagttgtc      420
acgggcgaca gccagttttg tagtcaaaaa gcagtcatct attcattgaa ttttacagca      480
aacccacctc aaagagtatt tgaacttgtt gaccagatta atccatctat tttctgcatt      540
catattacaa actataaacc tgcattatcc tttattaatc cagaagtacc tgatgaaaac      600
aattttgata cattgatgaa aacatctgat ggttttacat tgaatgctga atcatatgtt      660
tccttcacaa ccaaactgga tattcctact gctgctaaat atgagtatgg ggttcctctg      720
cagacttcag attcgtttct gagatttcct tcgtccctga catcatctct gtgcactgat      780
aataaccctg cagcgtttct ggtgaaccag gctgttaagt gcaccagaaa aataaattta      840
gaacagtgtg aagaaattga agccctcagc atggcttttt acagcagccc ggaaattctg      900
```

| | |
|---|---|
| agggtacctg attcaagaaa aaaggtccct atcactgttc agtccatcgt cattcagtct | 960 |
| ctaaataaaa cgctcacccg acgggaggac actgatgtgc tgcagccgac tctcgtcaac | 1020 |
| gctggacact ttagcctttg cgtgaatgtt gttcttgagg taaagtacag cctcacatac | 1080 |
| acagatgcag gtgaagtcac caaagctgat ctctcattcg ttctggggac agttagcagc | 1140 |
| gtagtggtcc cactgcagca aaagtttgaa attcattttc ttcaggaaaa tacccagcca | 1200 |
| gtccctctca gtgaaaccc tggttatgtc gtggggctcc cattagctgc tggattccag | 1260 |
| cctcataagg ggtctgggat tattcagacc acaaatagat atggacagct tactattctt | 1320 |
| catagcacaa ctgagcaaga ctgcttagca ctggaggggg tccggacccc agtattattt | 1380 |
| ggttacacta tgcaatctgg ctgtaaacta agactgactg gagctctccc gtgtcagctc | 1440 |
| gtagcacaga aggtgaagag cctgctgtgg ggccagggct tcccagatta cgtggcccct | 1500 |
| tttggaaatt cccaggccca ggacatgctg gactgggtgc ccatccactt catcacccag | 1560 |
| tcattcaaca ggaaggattc ctgccagctc ccagggggctt tggttataga agtgaagtgg | 1620 |
| actaaatacg gatccctgct gaatccacag gccaaaatag tcaatgtaac tgcaaatcta | 1680 |
| atttcatcct cctttcctga ggccaactca ggaaatgaaa ggacgattct tatttccact | 1740 |
| gcggttactt ttgtggatgt gtctgcacct gcagaggcag gcttcagagc tccaccagcc | 1800 |
| atcaatgcca ggctgcccctt taacttcttc ttcccgtttg tttgacaatg ctcagatgca | 1860 |
| tcagttcctt aatatacacg tgaaatttga aaactgtaca ttcggtgaga ttaaattta | 1920 |
| tatacaacta gc | 1932 |

<210> SEQ ID NO 26
<211> LENGTH: 1917
<212> TYPE: DNA
<213> ORGANISM: Homo sapiens

<400> SEQUENCE: 26

| | |
|---|---|
| cttctcgcgg cttcgcaagc cccttcccgt gatgccccgc gcctggctgt cgcggttgcc | 60 |
| gggcaacgcg ctgtccatgt cgcgggcctc gctgggactc cctgggagat gaggccgcga | 120 |
| ggtctcccgc cgctcctggt ggtgctcctg ggctgctggg cctccgtgag cgcccagacc | 180 |
| gatgccaccc cggcggtgac gacagagggc ctcaactcca ccgaggcagc cctggccacc | 240 |
| ttcggaactt tcccgtcgac caggcccccc gggactccca gggctccagg gccctcctcc | 300 |
| ggccccaggc ctaccccagt cacggacgtt gctgttctct gtgtctgtga cttatcccca | 360 |
| gcacagtgtg acatcaactg ctgctgtgat cccgactgca gctccgtgga tttcagtgtc | 420 |
| ttttctgcct gctcagttcc agttgtcacg ggcgacagcc agttttgtag tcaaaaagca | 480 |
| gtcatctatt cattgaattt tacagcaaac ccacctcaaa gagtatttga acttgttgac | 540 |
| cagattaatc catctatttt ctgcattcat attacaaact ataaacctgc attatccttt | 600 |
| attaatccag aagtacctga tgaaaacaat tttgatacat tgatgaaaac atctgatggt | 660 |
| tttacattga atgctgaatc atatgtttcc ttcacaacca aactggatat tcctactgct | 720 |
| gctaaatatg agtatggggt tcctctgcag acttcagatt cgtttctgag atttccttcg | 780 |
| tccctgacat catctctgtg cactgataat aaccctgcag gccaggcgta ctggttcaca | 840 |
| cctgtaatcc cagcactctg ggaggccgag gcgagaggat cacttgaggt acctgattca | 900 |
| agaaaaaagg tccctatcac tgttcagtcc atcgtcattc agtctctaaa taaaacgctc | 960 |
| acccgacggg aggacactga tgtgctgcag ccgactctcg tcaacgctgg acactttagc | 1020 |
| ctttgcgtga atgttgttct tgaggtaaag tacagcctca catacacaga tgcaggtgaa | 1080 |

```
gtcaccaaag ctgatctctc attcgttctg gggacagtta gcagcgtagt ggtcccactg    1140
cagcaaaagt ttgaaattca ttttcttcag gaaaataccc agccagtccc tctcagtgga    1200
aaccctggtt atgtcgtggg gctcccatta gctgctggat ccagcctca taagatgtct     1260 gggattattc agaccacaaa tagatatgga cagcttacta ttcttcatag cacaactgag    1320
caagactgct tagcactgga gggggtccgg acccccagtat tatttggtta cactatgcaa   1380
tctggctgta aactaagact gactggagct ctcccgtgtc agctcgtagc acagaaggtg    1440
aagagcctgc tgtggggcca gggcttccca gattacgtgg ccccttttgg aaattcccag   1500
gcccaggaca tgctggactg ggtgcccatc cacttcatca cccagtcatt caacaggaag    1560
gattcctgcc agctcccagg ggctttggtt atagaagtga agtggactaa atacggatcc    1620
ctgctgaatc cacaggccaa aatagtcaat gtaactgcaa atctaatttc atcctccttt    1680
cctgaggcca actcaggaaa tgaaaggacg attcttattt ccactgcggt tacttttgtg    1740
gatgtgtctg cacctgcaga ggcaggcttc agagctccac cagccatcaa tgccaggctg    1800
ccctttaact tcttcttccc gtttgtttga caatgctcag atgcatcagt tccttaatat    1860
acacgtgaaa tttgaaaact gtacattcgg tgagattaaa ttttatatac aactagc      1917

<210> SEQ ID NO 27
<211> LENGTH: 1909
<212> TYPE: DNA
<213> ORGANISM: Homo sapiens

<400> SEQUENCE: 27
gcaacgcgct gtccatgtcg cgggcctcgc tgggactccc tgggagatga ggccgcgagg    60
tctcccgccg ctcctggtgg tgctcctggg ctgctgggcc tccgtgagcg cccagaccga    120 tgccacccg gcggtgacga cagagggcct caactccacc gaggcagccc tggccacctt    180
cggaactttc ccgtcgacca ggccccccgg gactccagg gctccagggc cctcctccgg    240
ccccaggcct accccagtca cggacgttgc tgttctctgt gtctgtgact tatccccagc   300
acagtgtgac atcaactgct gctgtgatcc cgactgcagc tccgtggatt tcagtgtctt    360
ttctgcctgc tcagttccag ttgtcacggg cgacagccag ttttgtagtc aaaaagcagt   420
catctattca ttgaatttta cagcaaaccc acctcaaaga gtatttgaac ttgttgacca   480
gattaatcca tctatttct gcattcatat acaaactat aaacctgcat tatcccttat    540
taatccagaa gtacctgatg aaaacaattt tgatacattg atgaaaacat ctgatggttt   600
tacattgaat gctgaatcat atgtttcctt cacaaccaaa ctggatattc ctactgctgc   660
taaatatgag tatgggggttc ctctgcagac ttcagattcg tttctgagat ttccttcgtc    720
cctgacatca tctctgtgca ctgataataa ccctgcagcg tttctggtga ccaggctgt   780 taagtgcacc agaaaaataa atttagaaca gtgtgaagaa attgaagccc tcagcatggc    840
tttttacagc agcccggaaa ttctgagggt acctgattca agaaaaaagg tccctatcac   900
tgttcagtcc atcgtcattc agtctctaaa taaaacgctc acccgacggg aggacactga    960
tgtgctgcag ccgactctcg tcaacgctgg acactttagc ctttgcgtga atgttgttct    1020
tgaggtaaag tacagcctca catacacaga tgcaggtgaa gtcaccaaag ctgatctctc   1080
attcgttctg gggacagtta gcagcgtagt ggtcccactg cagcaaaagt ttgaaattca    1140
ttttcttcag gaaaataccc agccagtccc tctcagtgga aaccctggtt atgtcgtggg    1200
gctcccatta gctgctggat ccagcctca taagatgtct gggattattc agaccacaaa    1260
```

```
tagatatgga cagcttacta ttcttcatag cacaactgag caagactgct tagcactgga    1320
gggggtccgg accccagtat tatttggtta cactatgcaa tctggctgta aactaagact    1380
gactggagct ctcccgtgtc agctcgtagc acagaaggtg aagagcctgc tgtggggcca    1440
gggcttccca gattacgtgg ccccttttgg aaattcccag gcccaggaca tgctggactg    1500
ggtgcccatc cacttcatca cccagtcatt aacaggaag cattttgttt tgcaggattc    1560
ctgccagctc caggggcttt tggttataga agtgaagtgg actaaatacg gatccctgct    1620
gaatccacag gccaaaatag tcaatgtaac tgcaaatcta atttcatcct cctttcctga    1680
ggccaactca ggaaatgaaa ggacgattct tatttccact gcggttactt ttgtggatgt    1740
gtctgcacct gcagaggcag gcttcagagc tccaccagcc atcaatgcca ggctgccctt    1800
taacttcttc ttcccgtttg tttgacaatg ctcagatgca tcagttcctt aatatacacg    1860
tgaaatttga aaactgtaca ttcggtgaga ttaaattta tatacaact                 1909

<210> SEQ ID NO 28
<211> LENGTH: 2908
<212> TYPE: DNA
<213> ORGANISM: Homo sapiens

<400> SEQUENCE: 28
agctccgggc gttcgcttgc aagatggcgg cggcgggca gtggctgctg cgttttcgtg       60
tctgagtcct tcctgggttc taatgagggc gcggttctgc tgtgcccggc ccgcgaggtc     120
taaggcatgg gcttccagcc tccggccgct cttcttttga ggcttttcct tctgcagggc     180
atcctgaggc ttctgtgggg ggacctggct ttcatccctc cttttatccg aatgtccggc     240
cctgcggtca gcgcgtccct ggtcggagac accgagggtg tgaccgtgtc cctggcagtg     300
ctgcaggacg aggcgggaat attgccaatt ccgacgtgtg gagtgctgaa caatgagacg     360
gaagactgga gcgtgactgt gatccccggt gcgaaggtgt tggaagtgac agtgaggtgg     420
aagagaggtc tggactggtg ttcctccaat gagacagatt ccttctcaga gtcccctgt     480 atcctccaga cccttctggt ttcagcatct cataattcat cctgttcagc acatctactc     540
attcaagtgc aaatttatgc caactcttct ctgacccata tgcctcaga gaacgtgact     600 gtcattccta accaggtgta tcagcccctt ggcccttgtc cttgtaattt aacagctgga    660
gcctgtgatg ttcgctgctg ctgtgaccag gaatgctcat caaatttaac aacgctgttc    720
agacggtcct gcttcaccgg cgtgtttgga ggagacgtca atcctccttt tgatcagctc    780
tgctctgctg gacgacgac acgtggtgtc ccgattggt tcccttttct gtgtgtgcag      840
tccccccttg ccaacacacc cttccttggt tacttctatc atggtgctgt ttcccccaaa    900
caggactctt cctttgaagt atatgtggat actgacgcaa aagactttgc agactttggt    960
tacaaacaag gagatcccat tatgactgta aagaaggcat attttactat tccgcaggtg   1020
tccctggctg gcagtgtat gcagaacgcc cagtggcat ttcttcacaa ttttgatgtt      1080
aaatgcgtta ctaatttgga actataccaa gaacgagatg gtattatcaa tgcgaagata   1140
aagaatgttg ccttaggagg catagttaca ccaaaagtga tctatgagga agcaactgac   1200
ctagacaaat tcatcaccaa tacagaaact ccttttaaata acggatcaac ccctagaatt   1260
gtgaatgtgg aagaacatta tattttcaaa tggaataata ataccatcag tgaaataaat   1320
gttaaaattt ttagggcaga gattaatgcc caccagaaag ggataatgac acagagattt   1380
gtagtaaaat ttttaagcta taatagtggt aatgaagaag aattatctgg aaatccaggt   1440
taccaacttg gcaagcctgt ccgagctcta aatatcaaca ggatgaataa tgtcacgact   1500
```

```
ttacatcttt ggcaatcggc tggaaggggt ctgtgtacat cagcaacttt caaacccatt   1560
ttatttggag aaaatgtact ctctggatgc ctgttagaag tcgggattaa tgaaaattgt   1620
actcagctca gggagaatgc tgttgaaaga cttgattcat taatacaagc gactcacgtt   1680
gcaatgagag gcaactccga ttacgctgat cttagtgatg gctggctcga ataatacgt    1740 gtagatgccc ctgatccagg tgcagacccg ctggctagca gtgtgaacgg catgtgcctg   1800
gatattcctg ctcacctgag catccgcatc ctcatctcgg atgctggcgc ggtggaaggg   1860
attactcagc aggagatact cggtgtagag acaaggttct cctcagtgaa ctggcagtac   1920
cagtgtgggc ttacctgtga gcacaaggcc gaccttctcc ctatcagtgc atccgtccag   1980
tttattaaaa ttcctgcaca gttaccccac ccctgacaa gattccagat caattataca    2040
gagtatgact gcaacagaaa tgaggtgtgt tggccgcagc ttctatatcc atggactcag   2100
tattatcaag gggagctgca ttctcagtgt gttgctaagg gcttactgtt gctgttgttc   2160
ctcacattgg ccttgttcct cagcaacccc tggaccagaa tatgcaaagc ctatagttag   2220
acaaccacct ggcttttatt ttttgagat ggagttttgc tcttgttgcc caggctgaag     2280
tgatctcggc tcaccacaac ctcctcctct gggttcaag cgattctcct gcctcagcct     2340
ccggagaact gggattacag gcatgcacca ccacgcccgg ctaattttgt attttagta    2400 gagacagggt tccaccgtat tggccaggct gctctcgaac tcctgacctc atgatccgcc   2460
catcttggcc tcccaaagtg ctgagattac aggcatgagc caccgcaccc ggcctttttt   2520
tttttttttt tttttttgag gcggggtctc tgtcacccag gctggagtgc agtgcacaat   2580
ctcggctcac tgcaatctct gcctcccaag caatcctccc acctcagcct ctggtgtagc   2640
tgggaccaca gatgctccac catgcctggc tgtattttg gtaaagacgg ggtttcgcct    2700
tgttgcccag ggtggtctgt aactcctgag ctcagatgat ctgcccacct cggcctccca   2760
aagtgctggg atcacagacg tgagccactg cgtccggtcc atctgacttc tcaaagactt   2820
tagaccttga cttcagtgat tgttgtagt cttgtatgct tctctataaa attttaataa    2880
atgaaatgtc ttattttttgt agaaaatt                                       2908
```

<210> SEQ ID NO 29
<211> LENGTH: 2067
<212> TYPE: DNA
<213> ORGANISM: Homo sapiens

<400> SEQUENCE: 29

```
atgcgattgg agaccgcgga ggcctacgtc ggacccggag gccctgaatg ccccatgcgc      60
accccacagc tcgcgctcct gcaagtgttc tttctggtgt ccccgatgg cgtccggcct     120 cagccctctt cctccccatc aggggcagtg cccacgtctt tggagctgca gcgagggacg     180
gatggcggaa ccctccagtc cccttcagag gcgactgcaa ctcgcccggc cgtgcctgga    240
ctccctacag tggtccctac tctcgtgact ccctcggccc ctgggaatag gactgtggac    300
ctcttcccag tcttaccgat ctgtgtctgt gacttgactc ctggagcctg cgatataaat    360
tgctgctgcg acagggactg ctatcttctc catccgagga cagttttctc cttctgcctt    420
ccaggcagcg taaggtcttc aagctgggtt tgtgtagaca actctgttat cttcaggagt    480
aattccccgt ttccttcaag agttttcatg gattctaatg gaatcaggca gttttgtgtc    540
catgtgaaca actcaaactt aaactatttc cagaagcttc aaaaggtcaa tgcaaccaac    600
ttccaggccc tggctgcaga gtttggaggc gaatcattca cttcaacatt ccaaactcaa    660
```

```
tcaccaccat cttttttacag ggctggggac cccattctta cttacttccc caagtggtct    720
gtaataagct tgctgagaca acctgcagga gttggagctg ggggactctg tgctgaaagc    780
aatcctgcag gtttcctaga gagtaaaagt acaacttgca ctcgtttttt caagaacctg    840
gctagtagct gtaccttgga ttcagccctc aatgctgcct cttactataa cttcacagtc    900
ttaaaggttc caagaagcat gactgatcca cagaatatgg agttccaggt tcctgtaata    960
cttacctcac aggctaatgc tcctctgttg gctggaaaca cttgtcagaa tgtagtttct   1020
caggtcacct atgagataga gaccaatggg acttttggaa tccagaaagt ttctgtcagt   1080
ttgggacaaa ccaacctgac tgttgagcca ggcgcttcct tacagcaaca cttcatcctt   1140
cgcttcaggg cttttcaaca gagcacagct gcttctctca ccagtcctag aagtgggaat   1200
cctggctata tagttgggaa gccactcttg gctctgactg atgataagg ttactcaatg    1260 accctcttac agagccaggg taatggaagt tgctctgtta aaagacatga agtgcagttt   1320
ggagtgaatg caatatctgg atgcaagctc aggttgaaga aggcagactg cagccacttg   1380
cagcaggaga tttatcagac tcttcatgga aggcccagac cagagtatgt tgccatcttt   1440
ggtaatgctg acccagccca gaaaggaggg tggaccagga tcctcaacag gcactgcagc   1500
atttcagcta taaactgtac ttcctgctgt ctcataccag tttccctgga gatccaggta   1560
ttgtgggcat atgtaggtct cctgtccaac ccgcaagctc atgtatcagg agttcgattc   1620
ctataccagt gccagtctat acaggattct cagcaagtta cagaagtatc tttgacaact   1680
cttgtgaact ttgtggacat tacccagaag ccacagcctc caaggggcca acccaaaatg   1740
gactggaaat ggccattcga cttctttccc ttcaaagtgg cattcagcag aggagtattc   1800
tctcaaaaat gctcagtctc tcccatcctt atcctgtgcc tcttactact ggagttctc    1860 aacctagaga ctatgtgaag aaaagaaaat aatcagattt cagttttccc tatgagaaac   1920
tctgaggcag ccacttatct tggctaaata gaacctcacc tgctcatgac cagagagcat   1980
ttaggataat agaggaccta actgaaggaa tccttgtata tgaaaggagt tattttagaa   2040
aagcaataaa aatattttat tcatcat                                       2067
```

<210> SEQ ID NO 30
<211> LENGTH: 1940
<212> TYPE: DNA
<213> ORGANISM: Homo sapiens

<400> SEQUENCE: 30

```
aatgccccat gcgcacccca cagctcgcgc tcctgcaagt gttctttctg gtgttccccg     60
atggcgtccg gcctcagccc tcttcctccc catcaggggc agtgcccacg tctttggagc    120
tgcagcgagg gacggatggc ggaaccctcc agtccccttc agaggcgact gcaactcgcc    180
cggccgtgcc tggactccct acagtggtcc ctactctcgt gactccctcg gcccctggga    240
ataggactgt ggacctcttc ccagtcttac cgatctgtgt ctgtgacttg actcctggag    300
cctgcgatat aaaattgctgc tgcgacaggg actgctatct tctccatccg aggacagttt    360
tctccttctg ccttccaggc agcgtaaggt cttcaagctg ggtttgtgta gacaactctg    420
ttatcttcag gagtaattcc ccgtttcctt caagagtttt catggattct aatggaatca    480
ggcagttttg tgtccatgtg aacaactcaa acttaaacta tttccagaag cttcaaaagg    540
tcaatgcaac caacttccag gccctggctg cagagtttgg aggcgaatca ttcacttcaa    600
cattccaaac tcaatcacca ccatcttttt acagggctgg ggaccccatt cttacttact    660
tccccaagtg gtctgtaata agcttgctga gacaacctgc aggagttgga gctgggggac    720
```

```
tctgtgctga aagcaatcct gcaggtttcc tagagagtaa aagtacaact tgcactcgtt      780
ttttcaagaa cctggctagt agctgtacct tggattcagc cctcaatgct gcctcttact      840
ataacttcac agtcttaaag gttccaagaa gcatgactga tccacagaat atggaggtca      900
cctatgagat agagaccaat gggacttttg aatccagaa agtttctgtc agtttgggac       960
aaaccaacct gactgttgag ccaggcgctt ccttacagca acacttcatc cttcgcttca     1020
gggcttttca acagagcaca gctgcttctc tcaccagtcc tagaagtggg aatcctggct     1080
atatagttgg gaagccactc ttggctctga ctgatgatat aagttactca atgaccctct     1140
tacagagcca gggtaatgga agttgctctg ttaaaagaca tgaagtgcag tttggagtga     1200
atgcaatatc tggatgcaag ctcaggttga agaaggcaga ctgcagccac ttgcagcagg     1260
agatttatca gactcttcat ggaaggccca gaccagagta tgttgccatc tttggtaatg     1320
ctgacccagc ccagaaagga gggtggacca ggatcctcaa caggcactgc agcatttcag     1380
ctataaactg tacttcctgc tgtctcatac cagtttccct ggagatccag gtattgtggg     1440
catatgtagg tctcctgtcc aacccgcaag ctcatgtatc aggagttcga ttcctatacc     1500
agtgccagtc tatacaggat tctcagcaag ttacagaagt atctttgaca actcttgtga     1560
actttgtgga cattacccag aagccacagc ctccaagggg ccaacccaaa atggactgga     1620
aatggccatt cgacttcttt cccttcaaag tggcattcag cagaggagta ttctctcaaa     1680
aatgctcagt ctctcccatc cttatcctgt gcctcttact acttggagtt ctcaacctag     1740
agactatgtg aagaaaagaa ataatcaga tttcagtttt ccctatgaga aactctgagg      1800
cagccactta tcttggctaa atagaacctc acctgctcat gaccagagag catttaggat     1860
aatagaggac ctaactgaag gaatccttgt atatgaaagg agttattta gaaaagcaat      1920 aaaaatattt tattcatcat                                                 1940

<210> SEQ ID NO 31
<211> LENGTH: 1464
<212> TYPE: DNA
<213> ORGANISM: Homo sapiens

<400> SEQUENCE: 31
atgcgcaccc cacagctcgc gctcctgcaa gtgttctttc tggtgttccc cgatggcgtc       60
cggcctcagc cctcttcctc cccatcaggg gcagtgccca cgtctttgga gctgcagcga      120
gggacggatg gcggaaccct ccagtcccct tcagaggcga ctgcaactcg cccggccgtg      180
cctggactcc ctacagtggt ccctactctc gtgactccct cggcccctgg aataggact       240 gtggacctct tcccagtctt accgatctgt gtctgtgact tgactcctgg agcctgcgat      300
ataaattgct gctgcgacag ggactgctat cttctccatc cgaggacagt tttctccttc      360
tgccttccag gcagcgtaag gtcttcaagc tgggtttgtg tagacaactc tgttatcttc      420
aggagtaatt ccccgtttcc ttcaagagtt ttcatggatt ctaatggaat caggcagttt      480
tgtgtccatg tgaacaactc aaacttaaac tatttccaga agcttcaaaa ggtcaatgca      540
accaacttcc aggccctggc tgcagagttt ggaggcgaat cattcacttc aacattccaa      600
actcaatcac caccatcttt ttacagggct ggggaccca ttcttactta cttccccaag       660
tggtctgtaa taagcttgct gagacaacct gcaggagttg gagctggggg actctgtgct      720
gaaagcaatc ctgcaggttt cctagagagt aaaagtacaa cttgcactcg tttttttcaag     780 aacctggcta gtagctgtac cttggattca gccctcaatg ctgcctctta ctataacttc     840
```

```
acagtcttaa aggttccaag aagcatgact gatccacaga atatggagtt ccaggttcct      900
gtaatactta cctcacaggc taatgctcct ctgttggctg aaacacttg tcagaatgta       960 gtttctcagg tcacctatga gatagagacc aatgggactt ttggaatcca gaaagtttct    1020
gtcagtttgg gacaaaccaa cctgactgtt gagccaggcg cttccttaca gcaacacttc    1080
atccttcgct tcagggcttt tcaacagagc acagctgctt ctctcaccag tcctagaagt    1140
gggaatcctg gctatatagt tgggaagcca ctcttggctc tgactgatga tataagttac    1200
tcagtatcct ttttagagct gggtggcctg ttgcagccta atgagaaaag ctgcaaaggc    1260
tttcaaactt atgttagact agccaaaggt gaggaatttt tgttcatta taatgaggta     1320 cttatatact aatatatggt taatcatttt tggaatctag ttgtctctct gtggttttct    1380
gaggaaaaaa atcacaaatt tgtgactcga acattatgat agtaatacaa ataaatagc     1440 attaaaggag aatgagaaca taaa                                           1464

<210> SEQ ID NO 32
<211> LENGTH: 2734
<212> TYPE: DNA
<213> ORGANISM: Homo sapiens

<400> SEQUENCE: 32
ggttgccagg caacggaggc acggcccggc ccgcgttaag gaggagggcg cagaccgaag       60
gacactgaaa gagctgtaac aaccccactt tcgattggtt gaagagctct cagccttctc     120
atgagccaat gagaagaggc acgcggatgg cgtcagacgc tatgcgactc ctcccaccca     180
cgctctggca atgcgattgg agaccgcgga ggcctacgtc ggacccggag ccctgaatg      240 ccccatgcgc accccacagc tcgcgctcct gcaagtgttc tttctggtgt tcccgatgg      300 cgtccggcct cagccctctt cctccccatc aggggcagtg cccacgtctt tggagctgca    360
gcgagggacg gatggcggaa ccctccagtc cccttcagag gcgactgcaa ctcgcccggc    420
cgtgcctgga ctcccctacag tggtccctac tctcgtgact ccctcggccc tgggaatag     480 gactgtggac ctcttcccag tcttaccgat ctgtgtctgt gacttgactc ctggagcctg    540
cgatataaat tgctgctgcg acagggactg ctatcttctc catccgagga cagttttctc    600
cttctgcctt ccaggcagcg taaggtcttc aagctgggtt tgtgtagaca actctgttat    660
cttcaggagt aattccccgt ttccttcaag agttttcatg gattctaatg gaatcaggca    720
gttttgtgtc catgtgaaca actcaaactt aaactatttc cagaagcttc aaaaggtcaa    780
tgcaaccaac ttccaggccc tggctgcaga gtttggaggc gaatcattca cttcaacatt    840
ccaaactcaa tcaccaccat cttttttacag ggctgggac cccattctta cttacttccc    900
caagtggtct gtaataagct tgctgagaca acctgcagga gttggagctg ggggactctg    960
tgctgaaagc aatcctgcag gtttcctaga gagtaaaagt acaacttgca ctcgtttttt    1020
caagaacctg gctagtagct gtaccttgga ttcagccctc aatgctgcct cttactataa    1080
cttcacagtc ttaaaggttc caagaagcat gactgatcca cagaatatgg agttccaggt    1140
tcctgtaata cttacctcac aggctaatgc tcctctgttg gctggaaaca cttgtcagaa    1200 tgtagttct caggtcacct atgagataga gaccaatggg acttttggaa tccagaaagt    1260
ttctgtcagt ttgggacaaa ccaacctgac tgttgagcca ggcgcttcct tacagcaaca    1320
cttcatcctt cgcttcaggg cttttcaaca gagcacagct gcttctctca ccagtcctag    1380
aagtgggaat cctggctata tagttgggaa gccactcttg ctctgactg atgatataag    1440 ttactcaatg accctcttac agagccaggg taatggaagt tgctctgtta aaagacatga    1500
```

| | |
|---|---|
| agtgcagttt ggagtgaatg caatatctgg atgcaagctc aggttgaaga aggcagactg | 1560 |
| cagccacttg cagcaggaga tttatcagac tcttcatgga aggcccagac cagagtatgt | 1620 |
| tgccatcttt ggtaatgctg acccagccca gaaaggaggg tggaccagga tcctcaacag | 1680 |
| gcactgcagc atttcagcta taaactgtac ttcctgctgt ctcataccag tttccctgga | 1740 |
| gatccaggta ttgtgggcat atgtaggtct cctgtccaac ccgcaagctc atgtatcagg | 1800 |
| agttcgattc ctataccagt gccagtctat acaggattct cagcaagtta cagaagtatc | 1860 |
| tttgacaact cttgtgaact ttgtggacat tacccagaag ccacagcctc caaggggcca | 1920 |
| acccaaaatg gactggaaat ggccattcga cttctttccc ttcaaagtgg cattcagcag | 1980 |
| aggagtattc tctcaaaaat gctcagtctc tcccatcctt atcctgtgcc tcttactact | 2040 |
| tggagttctc aacctagaga ctatgtgaag aaagaaaat aatcagattt cagttttccc | 2100 |
| tatgagaaac tctgaggcag ccacttatct tggctaaata gaacctcacc tgctcatgac | 2160 |
| cagagagcat ttaggataat agaggaccta actgaaggaa tccttgtata tgaaaggagt | 2220 |
| tattttagaa aagcaataaa aatatttat tcatcatagc tctctgcttt gggctctgca | 2280 |
| ggccaccaga tacacatgag gcccctactt ctcaagctgg gaaggccaag agccttcctt | 2340 |
| cagcctttct ggttatgtta cacctagctg aatgtttaca aggtctggat ccatcagccc | 2400 |
| tcaggcacag ttgggccaag cagaaagaga gaaacacttc tgctgtcacc ttgaatgaac | 2460 |
| tcaggaatag cttccctctg gactgtagag gagctaactg tttggaacag aaaactgctg | 2520 |
| gctgttgatt ttgtctggtt cctttgccaa catctgggca cacccttgc ccagacacga | 2580 |
| gtggggaaag cagttctttc tcctcagttt ccaaagtaaa tggggaatcc cagctttctt | 2640 |
| ttctactagc aaatgaccct accatttatt tctgcctttt tcttccgttc attgtgagga | 2700 |
| aaaataaaac tggttgagag ctttgttgta ctaa | 2734 |

<210> SEQ ID NO 33
<211> LENGTH: 631
<212> TYPE: DNA
<213> ORGANISM: Homo sapiens

<400> SEQUENCE: 33

| | |
|---|---|
| gaggctgagg tcggagtccc gattttctcc tgctgctgtg gcccggacat ggcgactccc | 60 |
| ggccctgtga ttccggaggt ccccttgaa ccatcgaagc tccagtcat tgagggctg | 120 |
| agccccactg tttacaggaa tccagagagt ttcaaggaaa agttcgttcg caagacccgc | 180 |
| gagaacccgg tggtacccat aggttgcctg gccacggcgg ccgccctcac ctacggcctc | 240 |
| tactccttcc accggggcaa cagccagcgc tctcagctca tgatgcgcac ccggatcgcc | 300 |
| gcccagggtt tcacggtcgc agccatcttg ctgggtctgg ctgtcactgc tatgaagtct | 360 |
| cgaccctaag cccagggtct ggccttgaaa gctccgcaga aatgattcca aacccaggg | 420 |
| agcaaccact ggccctaccg tgggacttac tccctcctct cctttgagag gcccatgtgt | 480 |
| cgctggggag gaagtgaccc tttgtgtaac tgtaaccgaa agttttttca aaaatcctag | 540 |
| atgctgttgt ttgaatgtta catacttcta tttgtgccac atctcccctc cactccctg | 600 |
| cttaataaac tctaaaaatc cacttgtatt t | 631 |

<210> SEQ ID NO 34
<211> LENGTH: 1085
<212> TYPE: DNA
<213> ORGANISM: Homo sapiens

<400> SEQUENCE: 34

```
ggaggactgt gaggaagcgg gggaaggaag taaatcgccg agtgacctaa ggaatcaggg      60
ggaggattag ggtctgctcc acagaaggct tacctctgaa agagtcgggg agggaatgcg     120
cagccactcg ctgcctttat cccgagaagc ccctaacacc cctcgccgtg gtctgtacat     180
ggtctgtacc tccggccgcg ctggctggta ggccagccac ctgggatggc agcctagttc     240
tcccgccacc ttaccctgcc ctgactctaa tctgcattta attcagtcct tcttccggga     300
gatttcggcg gagaatttct ttctcgcctt agctactgag gtcaaacctg aaataggctg     360
tagactccac cagctgggta agaatgggaa gaagatcaga aaacctaaac tttggttgat     420
ggactatttt gcccaggcaa aagcagggaa tctatgagga atatgaagac attcgtcggg     480
agaactctgt tggcactttc cactgttcca tctgtggcct aggcatggcg actctcggct     540
tgtgactcc ggaggccccc tttgaatcat cgaagccccc catctttgag gggcttagcc     600
ccactgttta cagcaatcca gagggtttca aggaaaagtt ccttcgcaag acccgcgaga     660
atccggtggt acccataggt ttcctgtgca cggcggccgt cctcaccaac ggcctctact     720
gcttccacca gggcaacagc caatgttcac ggcttatgat gcacaccag atcgccgccc      780
agggcttcac cattgcagcc atcttgctgg gtctagctgc caccgctatg aagtctccac     840
cctgagccca gggtcttgaa aactctgcag aaatcattcc aaaacccagg agcaaccact     900
ggccctacca tgggacttac tctctcctct cctttgagag gtccctgtgt cgttggggga     960
ggaagtgacc cttcctgtaa ccataactga aagattttt caaaaatccc agattctgtt    1020
gtttgaatgt tacatatttc tatttgtgcc acatcttccc tccactcccc tgcttaataa    1080
actct                                                                1085
```

<210> SEQ ID NO 35
<211> LENGTH: 2593
<212> TYPE: DNA
<213> ORGANISM: Homo sapiens

<400> SEQUENCE: 35

```
tggtgcgtcg cggcgtggtc ctccggcggc tgtccggggc ggtaggagtt ggctgcggga      60
tgtgctcagc cggggagctg ctgcggggcg gcgacggcgg ggaacgcgac gaggacgggg     120
acgcgctggc ggagcgggag gcggcaggga ccgggtggga tcccggggcg agcccgcggc     180
ggcgcggaca gcggccgaag gagagcgagc aggatgttga agactcacag aaccacactg     240
gtgagccggt tggagatgac tacaagaaaa tgggaacact ttttggtgaa ctgaacaaaa     300
accttatcaa catgggcttc acaaggatgt attttggaga acgaatagtg gaaccagtaa     360
tagtcatttt cttttgggtt atgctgtggt tccttggcct gcaagcccctt ggactagttg     420
ctgttctttg ccttgttatt atttatgtgc aacagtaaaa catggccgaa ttgaattgtt     480
tgacatttgg tagccatata tgtaattgaa gaagttatat atttcacttt ttgcaaccg      540
aaaaagtttg ccttgtttca aatcatgtgc tggctgtttt gtaagtaaat ttatacatgg     600
atgtcactta aaactaaact cttgatcata acagggttga atatatattt tgaatataca     660
ttagcttatt caaaactctt gtttcactac tgtgatctct gtctcctta tacacctcta      720
tccccatgcc aaatcttaag taacaccacc agaaagtgaa cagggaaaat aacaggacat     780
ggaattcaaa tcaagcaata tagttcttat aaagagttcc aataaaacat ttcagaagaa     840
aaagtatgaa acaagctaaa agtaagtttc acttagaaaa cttctcccca ctcacactcc     900
ccaccaaata atctcatatt atttgggaaa tatttggatt tcaattgtcc ctacccagcc     960
```

```
taaactaagg taaatgataa ttagcataca ctaccttaat attgtgatga aaatcagtaa    1020
agatagaacg ttttctaaag gtcaaaaata atatatttat tattactggg aaagctccc    1080 aggttaaata taactttttt aaaatgtaac atttggacct agacctactt taatatatca    1140
tttgaagttt cagacaattt tggtgctaat tactttttgt gagttttaa agtctcatag     1200 cctagttgac tgcaccctat ggtaatgcca tattttcttg tatctaacaa gttgcatatt    1260
ttttcctaga gagacatttt cagtgtattt tttttagaa atttataatt ttatagttct     1320
ttcataacac ttattctgag ttttgaaaca atgtatttcc tatcttgaca tggattttt    1380 cacaaaaaat ttgtatttta ctgttgtttt caggaaaaaa atcagatcat ttttctttga    1440
tatctatatc agaaaggtac aatattaaca gtataaaacc aaatgcttaa atttggaact    1500
tagccaattt tgataatctt tttctaaggc taaagtcaca tcagtaattg ctagccatg     1560 ttattaaggt gtcttaattc agcattttca ggttttatat tgaaatacgc atttctttaa    1620
atattctttg aaaatggaga atggcttag tgatattttg ggttttgtta gagaacctaa     1680
aatctttaca ctttcatctc aaagattata aaggaaaggg gggtagttaa gatttagaat    1740
tcaagttaaa tttcagaaat tggggcagtc aggcatttgt atctttggta gggcaacaag    1800
taaaacatgt agagtgcttg ctatcccact tcataaagct tttacccaat cttatttcta    1860
aacctctgtg cattcttagt gtcttctcat tctgaaacag aaaataagga aaacattta     1920 acttagtttt ctaaaatcag ataatcctaa acaaaaatgt tagtcagggt cactaaaaag    1980
tattgcacat ttatataaat acagtccttt taaaatttga cttttaaaaa acaaagact     2040 ttgtacgata ttgtgttttt attgcttttg caatattttt atagtagcct ttatgaactc    2100
agtataagtg caagttgttt gaaaaggtgt tttattagt gcacaataga attgtgaggt     2160
tttcaataga tgtcatgaga ttttgtatat ctacataaaa tatcagtaca tttttttcta    2220
atgctactgg aaattttact tttcctttgc aacacataaa tgatatgatg tacaaaataa    2280
cagctctggt tccaccagta cctaatgttg aaaacatttt taaagtaatt tttaatacta    2340
actatttagt atactgtcag tactgtacat ctgcacactg gtgttaatag ggtatatatt    2400
aaattatata agaaataag atattttgct gttattcttt ctacatatat tattggtcag    2460
tacatcaaat aatatttggc tttgatatgg gaaaaaacaa actttgccta tgtaatggaa    2520
ataaaatatt ttcttttatg aaatatatta gaatgcagat tatactaata tcctgaaata    2580
aaactggtaa ttt                                                       2593
```

<210> SEQ ID NO 36
<211> LENGTH: 3697
<212> TYPE: DNA
<213> ORGANISM: Homo sapiens

<400> SEQUENCE: 36

```
aggcaacctc cagccagtcc ctgggtcggg cggatcctcc cagaggtggc acaatggagc      60
gatctccagg agagggcccc agccccagcc ccatggacca gccctctgct ccctccgacc     120
ccactgacca gccccccgct gctcacgcaa agccagaccc aggttctggg ggccaacctg     180
ctggccctgg cgcggcgggt gaggccctgg cggtgctgac ttcattcggg aggcggttgc     240
tggtgctgat acctgtgtat ttggccgggg cagtgggact cagcgtgggt ttcgtgctct     300
tcggcctcgc cctctacctg gctggcgcc gggtccgcga cgagaaagaa cggagccttc     360
gagcagcgag gcagctactg gacgacgagg agcagctcac tgcgaaaact ctctatatga    420
```

```
gtcatcgaga gctacctgcc tgggtcagct tcccagacgt ggaaaaggct gaatggctca      480
ataagattgt ggcccaggtc tggcccttcc tgggccagta tatggagaag cttctggctg      540
aaactgtggc tccggctgtt aggggatcta acccccatct gcaaacattt acatttacac      600
gagtggaact gggtgaaaag ccattgcgca tcattggagt caaggttcac ccaggtcaga      660
gaaaagagca gatcctgctg gacttgaaca tcagctatgt aggtgatgtg cagattgatg      720
tggaagtgaa gaaatatttt tgcaaagcag gagtcaaggg catgcagcta catggcgttt      780
tgcgggtgat actggagcca ctcattgggg accttccctt cgtggggct gtgtcaatgt       840 tcttcatccg acgcccgacc ctagacatca actggacagg gatgaccaac ctgctggata      900
tcccaggact tagctcactc tctgacacca tgatcatgga ctccattgct gccttcctcg      960
tgttgcccaa ccgattactg gtgccccttg tgcctgacct tcaagatgtg gctcagttgc     1020
gttcccctct gcccaggggc attattcgaa ttcacctgct ggctgctcga gggctgagtt     1080
ccaaggacaa atatgtgaag ggcctgattg agggcaagtc agacccatat gcacttgtgc     1140
gtttgggtac ccagacattc tgcagtcgtg tcattgatga agaactcaac ccacagtggg     1200
gagagactta tgaggtgatg gtacacgagg tcccagggca ggagattgaa gtggaggtgt     1260
tcgacaagga tccagataaa gatgactttc tgggcagaat gaagctggat gtaggggaagg    1320 tgttacaggc tagcgttctg gatgattggt ccctctaca aggtgggcaa ggccaagttc      1380
acttgaggct agaatggctg tcactttgt cagatgcaga gaaactggag caggttctac      1440
agtggaattg gggagtctcc tctcgaccag atccccgtc agctgccatc ttagttgtct       1500
acctggatcg ggcccaggat cttcctctga agaagggaa caaggaaccc aaccctatgg      1560
tacaactgtc aattcaggat gtgactcagg agagcaaggc tgtctacagt accaactgcc     1620
cagtgtggga ggaagcgttc cggttcttcc tacaagaccc tcaaagccag gagctcgatg     1680
tgcaagtgaa ggatgattcc agggccctga ctttaggagc actgacgctg cctctggccc     1740
gcctgctgac tgccccagaa ctcatcctgg accagtggtt ccagctcagc agctctggtc      1800
caaactccag actctatatg aaactagtca tgaggatcct gtacttggat tcatcagaaa     1860
tatgcttccc cacggtgcct ggttgtcctg gtgcttggga cgtggacagt gagaatcccc     1920
agagaggcag cagtgtggat gccccacctc gaccctgtca cacgactcct gatagccagt     1980
ttgggactga gcatgtgctt cggatccatg tattagaggc ccaggacctg attgccaaag     2040
accgtttctt gggggggactg gtgaagggca agtcagaccc ctatgtcaaa ctaaagttgg     2100
caggacgaag cttccggagc catgttgttc gggaagatct caatcccgc tggaatgagg       2160 tttttgaggt gatcgtcaca tcagttccag gccaagagct agaggttgaa gtcttgaca     2220 aggacttgga caaggatgat tttctgggca ggtgtaaagt gcgtctcacc acagtcttaa      2280
acagtggctt ccttgatgag tggctgaccc tggaggatgt cccatctggc cgcctgcact     2340
tgcgcctgga gcgtctcacc cccgtccca ctgctgctga gttagaggag gtgctgcagg      2400
tgaatagttt gatccagact cagaagagtg cggagctggc tgcggccctg ctatccatct      2460
atatggagcg ggcagaggac ctcccgctgc gaaaaggcac caagcacctc agcccttatg     2520
ctactctcac tgtgggagat agttctcata aaaccaagac tatttcgcaa acttcagccc     2580
ctgtctggga tgagagtgcc tccttctca tcaggaaacc acacactgag agcctagagt      2640
tgcaggttcg gggtgagggc actggcgtgc tgggctcatt atccctgccc ctctcagagc     2700
tcctcgtggc tgaccagctc tgcttggacc gctggttac actcagcagt ggtcagggc      2760 aggtgctact gagagcacag ctagggatcc tggtgtccca gcactcggga gtggaagctc     2820
```

-continued

```
atagccacag ctacagccac agctcctcat cgctgagtga agaaccagag ctctcggggg    2880
gaccccctca catcacctcc tcagcccag agctccggca gcgcctaaca catgttgaca    2940
gtccccttga ggctccagcc gggcctctgg gccaggtgaa actgactctg tggtactaca    3000
gtgaagaacg aaagctggtc agcattgttc atggttgccg gtcccttcga cagaatggac    3060
gtgatcctcc tgatccctat gtgtcactgt tgctactgcc agacaagaac cgaggcacca    3120
agaggaggac ctcacagaag aagaggaccc tgagtcctga atttaatgaa cggtttgagt    3180
gggaactccc cctggatgag gcccagagac gaaagctgga tgtctctgtc aagtctaatt    3240
cctccttcat gtcaagagag cgtgagctgc tggggaaggt gcagctggac ctagctgaga    3300
cagacctttc ccagggtgta gcccggtggt atgacctgat ggacaacaag gacaagggca    3360
gctcctagga gctggcgagt cccagcctga ctgctctgtc ttcctgcctt cgtctcgctc    3420
catcaccgcc tcaatgtgat gagcctaaag ctagggtcca agggcagagc ctgtgccctt    3480
cagcccttc acctaacagg cccatattcg ggcctttgcc tgaccaaaga gaagaaccgt     3540
atgttccctt tactgcacgg cctttatcct tctgggcccc tggggcgggg acctgagctg    3600
gctgtttcct gctttgcctg cacattgttc tcccttcctc ccaactcctc agggccttct    3660
gtatctgtgc ctggatctta cattaaacat catactc                              3697
```

<210> SEQ ID NO 37
<211> LENGTH: 3727
<212> TYPE: DNA
<213> ORGANISM: Homo sapiens

<400> SEQUENCE: 37

```
aggcaacctc cagccagtcc ctgggtcggg cggatcctcc cagaggtggc acaatggagc      60
gatctccagg agagggcccc agcccagcc ccatggacca gccctctgct ccctccgacc      120
ccactgacca gccccccgct gctcacgcaa agccagaccc aggttctggg ggccaacctg     180
ctggccctgg cgcggcgggt gaggccctgg cggtgctgac ttcattcggg aggcggttgc     240
tggtgctgat acctgtgtat ttggccgggg cagtgggact cagcgtgggt ttcgtgctct     300
tcggcctcgc cctctacctg ggctggcgcc gggtccgcga cgagaaagaa cggagccttc     360
gagcagcgag gcagctactg gacgacgagg agcagctcac tgcgaaaact ctctatatga     420
gtcatcgaga gctacctgcc tgggtcagct cccagacgt ggaaaggct gaatggctca      480
ataagattgt ggcccaggtc tggccccttcc tgggccagta tatggagaag cttctggctg    540
aaactgtggc tccggctgtt aggggatcta acccccatct gcaaacatt acatttacac     600
gagtggaact gggtgaaaag ccattgcgca tcattggagt caaggttcac ccaggtcaga    660
gaaaagagca gatcctgctg gacttgaaca tcagctatg aggtgatgtg cagattgatg     720
tggaagtgaa gaaatatttt tgcaaagcag gagtcaaggg catgcagcta catggcgttt    780
tgcgggtgat actggagcca ctcattgggg accttccctt cgtgggggct gtgtcaatgt    840
tcttcatccg acgcccgacc ctagacatca actggacagg gatgaccaac ctgctggata    900
tcccaggact tagctcactc tctgacacca tgatcatgga ctccattgct gccttcctcg    960
tgttgcccaa ccgattactg gtgccccttg tgcctgacct tcaagatgtg gctcagttgc    1020
gttcccctct gcccaggggc attattcgaa ttcacctgct ggctgctcga gggctgagtt    1080
ccaaggacaa atatgtgaag ggcctgatta gggcaagtc agaccccatat gcacttgtgc   1140
gtttgggtac ccagacattc tgcagtcgtg tcattgatga agaactcaac ccacagtggg    1200
```

```
gagagactta tgaggtgatg gtacacgagg tcccagggca ggagattgaa gtggaggtgt    1260
tcgacaagga tccagataaa gatgactttc tgggcagaat gaagctggat gtagggaagg    1320
tgttacaggc tagcgttctg gatgattggt tccctctaca aggtgggcaa ggccaagttc    1380
acttgaggct agaatggctg tcacttttgt cagatgcaga gaaactggag caggttctac    1440
agtggaattg gggagtctcc tctcgaccag atccccgtc agctgccatc ttagttgtct     1500
acctggatcg ggcccaggat cttcctatgg tgacctctga attgtaccca ccacagctga    1560
agaaggggaa caaggaaccc aaccctatgg tacaactgtc aattcaggat gtgactcagg    1620
agagcaaggc tgtctacagt accaactgcc cagtgtggga ggaagcgttc cggttcttcc    1680
tacaagaccc tcaaagccag gagctcgatg tgcaagtgaa ggatgattcc agggccctga    1740
ctttaggagc actgacgctg cctctggccc gcctgctgac tgccccagaa ctcatcctgg    1800
accagtggtt ccagctcagc agctctggtc caaactccag actctatatg aaactagtca    1860
tgaggatcct gtacttggat tcatcagaaa tatgcttccc cacggtgcct ggttgtcctg    1920
gtgcttggga cgtggacagt gagaatcccc agagaggcag cagtgtggat gccccacctc    1980
gaccctgtca cacgactcct gatagccagt ttgggactga gcatgtgctt cggatccatg    2040
tattagaggc ccaggacctg attgccaaag accgttcctt gggggactg gtgaagggca     2100 agtcagaccc ctatgtcaaa ctaaagttgg caggacgaag cttccggagc catgttgttc    2160
gggaagatct caatccccgc tggaatgagg tttttgaggt gatcgtcaca tcagttccag    2220
gccaagagct agaggttgaa gtctttgaca aggacttgga caaggatgat tttctgggca    2280
ggtgtaaagt gcgtctcacc acagtcttaa acagtggctt ccttgatgag tggctgaccc    2340
tggaggatgt cccatctggc cgcctgcact tgcgcctgga gcgtctcacc ccccgtccca    2400
ctgctgctga gttagaggag gtgctgcagg tgaatagttt gatccagact cagaagagtg    2460
cggagctggc tgcggccctg ctatccatct atatggagcg ggcagaggac ctcccgctgc    2520
gaaaaggcac caagcacctc agcccttatg ctactctcac tgtgggagat agttctcata    2580
aaaccaagac tatttcgcaa acttcagccc ctgtctggga tgagagtgcc tcctttctca    2640
tcaggaaacc acacactgag agcctagagt tgcaggttcg gggtgagggc actggcgtgc    2700
tgggctcatt atccctgccc ctctcagagc tcctcgtggc tgaccagctc tgcttggacc    2760
gctggtttac actcagcagt ggtcaggggc aggtgctact gagagcacag ctagggatcc    2820
tggtgtccca gcactcggga gtggaagctc atagccacag ctacagccac agctcctcat    2880
cgctgagtga agaaccagag ctctcggggg gaccccctca catcacctcc tcagccccag    2940
agctccggca gcgcctaaca catgttgaca gtccccttga ggctccagcc gggcctctgg    3000
gccaggtgaa actgactctg tggtactaca gtgaagaacg aaagctggtc agcattgttc    3060
atggttgccg gtcccttcga cagaatggac gtgatcctcc tgatccctat gtgtcactgt    3120
tgctactgcc agacaagaac cgaggcacca agaggaggac ctcacagaag aagaggaccc    3180
tgagtcctga atttaatgaa cggtttgagt gggaactccc cctggatgag gcccagagac    3240
gaaagctgga tgtctctgtc aagtctaatt cctccttcat gtcaagagag cgtgagctgc    3300
tggggaaggt gcagctggac ctagctgaga cagacctttc ccagggtgta gcccggtggt    3360
atgacctgat ggacaacaag gacaagggca gctcctagga gctggcgagt cccagcctga    3420
ctgctctgtc ttcctgcctt cgtctcgctc catcaccgcc tcaatgtgat gagcctaaag    3480
ctagggtcca agggcagagc ctgtgccctt cagccctttc acctaacagg cccatattcg    3540
ggcctttgcc tgaccaaaga gaagaaccgt atgttccctt tactgcacgg ccttttatcct   3600
```

```
tctgggcccc tggggcgggg acctgagctg gctgtttcct gctttgcctg cacattgttc      3660
tcccttcctc ccaactcctc agggccttct gtatctgtgc ctggatctta cattaaacat      3720
catactc                                                                3727
```

<210> SEQ ID NO 38
<211> LENGTH: 4171
<212> TYPE: DNA
<213> ORGANISM: Homo sapiens

<400> SEQUENCE: 38

```
caacctccag ccagtccctg ggtcgggcgg atcctcccag aggtggcaca atggagcgat        60
ctccaggaga gggccccagc cccagcccca tggaccagcc ctctgctccc tccgacccca       120
ctgaccagcc ccccgctgct cacgcaaagc cagacccagg ttctgggggc caacctgctg       180
gccctggcgc ggcgggtgag gccctggcgg tgctgacttc attcgggagg cggttgctgg       240
tgctgatacc tgtgtatttg gccggggcag tgggactcag cgtgggtttc gtgctcttcg       300
gcctcgccct ctacctgggc tggcgccggg tccgcgacga aaagaacgg agccttcgag        360 cagcgaggca gctactggac gacgaggagc agctcactgc gaaaactctc tatatgagtc       420
atcgagagct acctgcctgg gtcagcttcc cagacgtgga aaaggctgaa tggctcaata       480
agattgtggc ccaggtctgg cccttcctgg gccagtatat ggagaagctt ctggctgaaa       540
ctgtggctcc ggctgttagg ggatctaacc cccatctgca aacatttaca tttacacgag       600
tggaactggg tgaaaagcca ttgcgcatca ttggagtcaa ggttcaccca ggtcagagaa       660
aagagcagat cctgctggac ttgaacatca gctatgtagg tgatgtgcag attgatgtgg       720
aagtgaagaa atattttgc aaagcaggag tcaagggcat gcagctacat ggcgttttgc       780
gggtgatact ggagccactc attggggacc ttcccttcgt ggggctgtg tcaatgttct       840 tcatccgacg cccgacccta gacatcaact ggacagggat gaccaacctg ctggatatcc       900
caggacttag ctcactctct gacaccatga tcatggactc cattgctgcc ttcctcgtgt       960
tgcccaaccg attactggtg cccccttgtg ctgaccttca agatgtggct cagttgcgtt      1020
cccctctgcc cagggggcatt attcgaattc acctgctggc tgctcgaggg ctgagttcca      1080
aggacaaata tgtgaagggc ctgattgagg gcaagtcaga cccatatgca cttgtgcgtt      1140
tgggtaccca gacattctgc agtcgtgtca ttgatgaaga actcaaccca cagtggggag      1200
agacttatga ggtgatggta cacgaggtcc agggcagga gattgaagtg gaggtgttcg       1260
acaaggatcc agataaagat gactttctgg gcagaatgaa gctggatgta gggaaggtgt      1320
tacaggctag cgttctggat gattggttcc ctctacaagg tgggcaaggc caagttcact      1380
tgaggctaga atggctgtca cttttgtcag atgcagagaa actggagcag gttctacagt      1440
ggaattgggg agtctcctct cgaccagatc ccccgtcagc tgccatctta gttgtctacc      1500
tggatcgggc ccaggatctt cctctgaaga agggaacaa ggaacccaac cctatggtac       1560
aactgtcaat tcaggatgtg actcaggaga gcaaggctgt ctacagtacc aactgcccag      1620
tgtgggagga agcgttccgg ttcttcctac aagaccctca aagccaggag ctcgatgtgc      1680
aagtgaagga tgattccagg gccctgactt taggagcact gacgctgcct ctggcccgcc      1740
tgctgactgc cccagaactc atcctggacc agtggttcca gctcagcagc tctggtccaa      1800
actccagact ctatatgaaa ctagtcatga ggatcctgta cttggattca tcagaaatat      1860
gcttccccac ggtgcctggt tgtcctggtg cttgggacgt ggacagtgag aatccccaga      1920
```

-continued

```
gaggcagcag tgtggatgcc ccacctcgac cctgtcacac gactcctgat agccagtttg    1980
ggactgagca tgtgcttcgg atccatgtat tagaggccca ggacctgatt gccaaagacc    2040
gtttcttggg gggactggtg aagggcaagt cagaccccta tgtcaaacta aagttggcag    2100
gacgaagctt ccggagccat gttgttcggg aagatctcaa tccccgctgg aatgaggttt    2160
ttgaggtgat cgtcacatca gttccaggcc aagagctaga ggttgaagtc tttgacaagg    2220
acttggacaa ggatgatttt ctgggcaggt gtaaagtgcg tctcaccaca gtcttaaaca    2280
gtggcttcct tgatgagtgg ctgaccctgg aggatgtccc atctggccgc ctgcacttgc    2340
gcctggagcg tctcaccccc cgtcccactg ctgctgagtt agaggaggtg ctgcaggtga    2400
atagtttgat ccagactcag aagagtgcgg agctggctgc ggccctgcta tccatctata    2460
tggagcgggc agaggacctc ccgctgcgaa aaggcaccaa gcacctcagc ccttatgcta    2520
ctctcactgt gggagatagt tctcataaaa ccaagactat ttcgcaaact tcagcccctg    2580
tctgggatga gagtgcctcc tttctcatca ggaaaccaca cactgagagc ctagagttgc    2640
aggttcgggg tgagggcact ggcgtgctgg gctcattatc cctgcccctc tcagagctcc    2700
tcgtggctga ccagtctctgc ttggaccgct ggtttacact cagcagtggt caggggcagg    2760
tgctactgag agcacagcta gggatcctgg tgtcccagca ctcgggagtg gaagctcata    2820
gccacagcta cagccacagc tcctcatcgc tgagtgaaga accagagctc tcgggggggac    2880 cccctcacat cacctcctca gccccagagc tccggcagcg cctaacacat gttgacagtc    2940
cccttgaggc tccagccggg cctctgggcc aggtgaaact gactctgtgg tactacagtg    3000
aagaacgaaa gctggtcagc attgttcatg gttgccggtc ccttcgacag aatgacgtg    3060 atcctcctga tccctatgtg tcactgttgc tactgccaga caagaaccga ggcaccaaga    3120
ggaggacctc acagaagaag aggacccctga gtcctgaatt taatgaacgg tttgagtggg    3180 aactcccccct ggatgaggcc cagagacgaa agctggatgt ctctgtcaag tctaattcct    3240
ccttcatgtc aagagagcgt gagctgctgg ggaaggtgca gctggaccta gctgagacag    3300
acctttccca gggtgtagcc cggtggtatg acctgatgga caacaaggac aagggcagct    3360
cctaggagct ggcgagtccc agcctgactg ctctgtcttc ctgccttcgt ctcgctccat    3420
caccgcctca atgtgatgag cctaaagcta gggtccaagg gcagagcctg tgcccttcag    3480
ccctttcacc taacaggccc atattcgggc ctttgcctga ccaaagagaa gaaccgtatg    3540
ttccctttac tgcacggcct ttatccttct gggcccctgg ggcggggacc tgagctggct    3600
gtttcctgct ttgcctgcac attgttctcc cttcctccca actcctcagg gccttctgta    3660
tctgtgcctg gccagtggca gcactagcag tggtattagc ttatgccaaa tacagctttg    3720
gaaggatctt ttttctttta actagatggt caccttcttc cctaccacac atgggtggga    3780
aggtggacag gctaacctct ccagctgtga gcctcttaga ctactgcatg tagcaaatgt    3840
tcagcagctc aggcccccat gtccagttct gtccccactg tcctcaaccc tgtcctgaaa    3900
attctactgc tttgatggct ggggccagtc tcttgtcact ttggaaactg aggacgcgtg    3960
gattctactc aagcctccaa gtagtggcat atcagtcttg gagctcctag ctggtgatac    4020
ggagagggct ttgaggact tgggacagca gggccaattt ttttgcccaa gtgcctaggc    4080
tgctaactca ctgactagaa cttaatctgg tactttacag ttttgcacca actctgccaa    4140
gccactggat cttacattaa acatcatact c                                   4171

<210> SEQ ID NO 39
<211> LENGTH: 21
```

<212> TYPE: DNA
<213> ORGANISM: Homo sapiens

<400> SEQUENCE: 39
ttgaacttgt tgaccagatt a         21

<210> SEQ ID NO 40
<211> LENGTH: 21
<212> TYPE: DNA
<213> ORGANISM: Homo sapiens

<400> SEQUENCE: 40
ttgcgtgaat gttgttcttg a         21

<210> SEQ ID NO 41
<211> LENGTH: 21
<212> TYPE: DNA
<213> ORGANISM: Homo sapiens

<400> SEQUENCE: 41
tgcatccgtc cagtttatta a         21

<210> SEQ ID NO 42
<211> LENGTH: 21
<212> TYPE: DNA
<213> ORGANISM: Homo sapiens

<400> SEQUENCE: 42
aagcctatag ttagacaacc a         21

<210> SEQ ID NO 43
<211> LENGTH: 21
<212> TYPE: DNA
<213> ORGANISM: Homo sapiens

<400> SEQUENCE: 43
tggctcgaaa taatacgtgt a         21

<210> SEQ ID NO 44
<211> LENGTH: 21
<212> TYPE: DNA
<213> ORGANISM: Homo sapiens

<400> SEQUENCE: 44
ttggaactat accaagaacg a         21

<210> SEQ ID NO 45
<211> LENGTH: 21
<212> TYPE: DNA
<213> ORGANISM: Homo sapiens

<400> SEQUENCE: 45
ttggctctga ctgatgatat a         21

<210> SEQ ID NO 46
<211> LENGTH: 21
<212> TYPE: DNA
<213> ORGANISM: Homo sapiens

<400> SEQUENCE: 46
aacccgcaag ctcatgtatc a         21

<210> SEQ ID NO 47

```
<211> LENGTH: 21
<212> TYPE: DNA
<213> ORGANISM: Homo sapiens

<400> SEQUENCE: 47
caggattctc agcaagttac a                                              21

<210> SEQ ID NO 48
<211> LENGTH: 21
<212> TYPE: DNA
<213> ORGANISM: Homo sapiens

<400> SEQUENCE: 48
cacggcggcc gccctcacct a                                              21

<210> SEQ ID NO 49
<211> LENGTH: 21
<212> TYPE: DNA
<213> ORGANISM: Homo sapiens

<400> SEQUENCE: 49
ctccgcagaa atgattccaa a                                              21

<210> SEQ ID NO 50
<211> LENGTH: 21
<212> TYPE: DNA
<213> ORGANISM: Homo sapiens

<400> SEQUENCE: 50
atcctagatg ctgttgtttg a                                              21

<210> SEQ ID NO 51
<211> LENGTH: 21
<212> TYPE: DNA
<213> ORGANISM: Homo sapiens

<400> SEQUENCE: 51
ttggacctag acctacttta a                                              21

<210> SEQ ID NO 52
<211> LENGTH: 21
<212> TYPE: DNA
<213> ORGANISM: Homo sapiens

<400> SEQUENCE: 52
cccagcctaa actaaggtaa a                                              21

<210> SEQ ID NO 53
<211> LENGTH: 21
<212> TYPE: DNA
<213> ORGANISM: Homo sapiens

<400> SEQUENCE: 53
aacgaatagt ggaaccagta a                                              21

<210> SEQ ID NO 54
<211> LENGTH: 21
<212> TYPE: DNA
<213> ORGANISM: Homo sapiens

<400> SEQUENCE: 54
gtgggagata gttctcataa a                                              21
```

```
<210> SEQ ID NO 55
<211> LENGTH: 21
<212> TYPE: DNA
<213> ORGANISM: Homo sapiens

<400> SEQUENCE: 55
acgcccgacc ctagacatca a                                              21
```